(12) United States Patent
Cheng et al.

(10) Patent No.: US 10,053,494 B2
(45) Date of Patent: Aug. 21, 2018

(54) CHEMICALLY ACTIVATED NANOCAPSID FUNCTIONALIZED FOR CANCER TARGETING

(71) Applicant: The Regents of the University of California, Oakland, CA (US)

(72) Inventors: R. Holland Cheng, Davis, CA (US); Li Xing, Davis, CA (US); Chun Chieh Chen, Oakland, CA (US); Marie Stark, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/312,582

(22) PCT Filed: May 18, 2015

(86) PCT No.: PCT/US2015/031439
§ 371 (c)(1),
(2) Date: Nov. 18, 2016

(87) PCT Pub. No.: WO2015/179321
PCT Pub. Date: Nov. 26, 2015

(65) Prior Publication Data
US 2017/0107261 A1     Apr. 20, 2017

Related U.S. Application Data

(60) Provisional application No. 62/000,465, filed on May 19, 2014.

(51) Int. Cl.
*C07K 14/00* (2006.01)
*C07K 14/005* (2006.01)
*A61K 9/51* (2006.01)

(52) U.S. Cl.
CPC .......... *C07K 14/005* (2013.01); *A61K 9/5169* (2013.01); *C12N 2770/28122* (2013.01); *C12N 2770/28123* (2013.01); *C12N 2770/28142* (2013.01)

(58) Field of Classification Search
None
See application file for complete search history.

(56) References Cited

U.S. PATENT DOCUMENTS

| | | | |
|---|---|---|---|
| 6,432,408 B1 * | 8/2002 | Meng | C07K 14/005 424/185.1 |
| 2012/0064169 A1 | 3/2012 | Cheng et al. | |

FOREIGN PATENT DOCUMENTS

| | | |
|---|---|---|
| WO | 2002053712 A2 | 7/2002 |
| WO | 2002053712 A3 | 7/2002 |

OTHER PUBLICATIONS

Guu et al. Structure of the hepatitis E virus-like particle suggests mechanisms for virus assembly and receptor binding. PNAS. vol. 106 No. 31, pp. 12992-12997. (Year: 2009).*
Baker et al., Protein Structure Predication and Structural Genomics, Science (2001) vol. 294, No. 5540, pp. 93-96.*
Attwood, T. The Babel of Bioinformatics, Science (2000) vol. 290, No. 5491, pp. 471-473.*
International Search Report in PCT/US2015/031439 dated Nov. 24, 2015, 7 pages.
Jariyapong et al., "Chimeric hepatitis E virus-like particle as a carrier for oral-delivery," Vaccine 2013, 31(2) 417-24.
Szuchmacher Blum, et al., "Cowpea mosaic virus as scaffold for 3-D patterning of gold nanoparticles," Nano Letters 2004, 4( )5): 867,870.
Yildiz, et al., "Engineering of brome mosaic virus for biomedical applications," RSC Adv., 2012, 2(9):3670-3677.
Extended European Search Report in EP15796952.8 dated Nov. 13, 2017.
Chen et al., "Chemically Activatable Viral Capsid Functionalized for Cancer Targeting," Nanomedicine 11, No. 4 (2016): 377-390.
Xing, et al. "Structure of hepatitis E virion-sized particle reveals an RNA-dependent viral assembly pathway." Journal of Biological Chemistry 285, No. 43 (2010): 33175-33183.

* cited by examiner

*Primary Examiner* — Michelle S Horning
(74) *Attorney, Agent, or Firm* — Kilpatrick Townsend & Stockton LLP

(57) ABSTRACT

Modified capsid proteins containing at least a portion of hepatitis E virus (HEV) open reading frame 2 (ORF2) having one or more cysteine residues in a surface variable loop or the C-terminus of HEV ORF2, or a portion thereof, are provided. The modified capsid proteins can be used to form hepatitis E virus (HEV) virus like particles (VLPs) having cysteine functional groups exposed on the outer-surface. The exposed cysteine functional groups can be modified via their thiol reactive group. For example, a bioactive agent, such as a cell-targeting ligand, can be conjugated to the one or more cysteines for targeted delivery of chemically activated nanocapsids.

17 Claims, 17 Drawing Sheets

Figure 1:
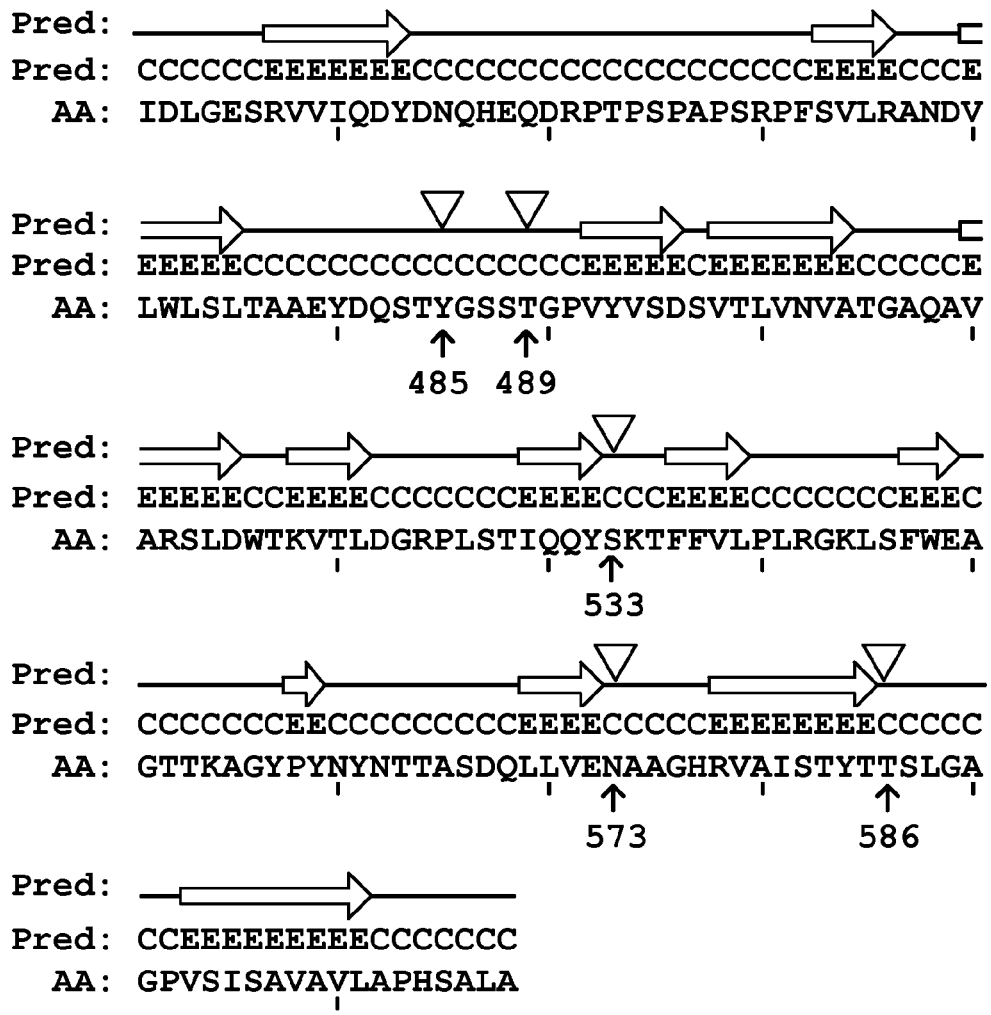
Figure 1:
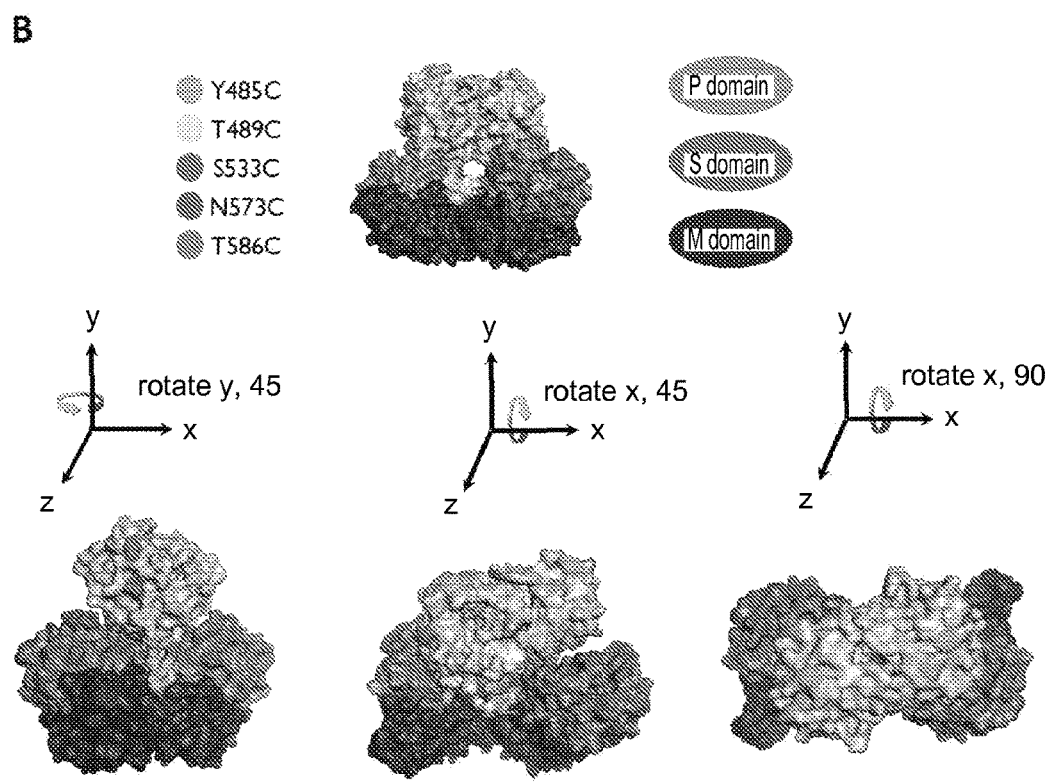

|   | Parental sequence | Forward and Reverse Primer With Cysteine Mutation |
|---|---|---|
| a | 5' GAC CAG TCC ACT TAT GGC TCT TCG ACT GGC 3'<br><br>3' CTG GTC AGG TGA ATA CCG AGA AGC TGA CCG 5' | 5'GAC CAG TCC ACT TGC GGC TCT TCG ACT GGC 3'<br><br>3'CTG GTC AGG TGA ACG CCG AGA AGC TGA CCG 5 |
| b | 5' CT TAT GGC TCT TCG ACT GGC CCA GTT TAT G 3'<br><br>3'GA ATA CCG AGA AGC TGA CCG GGT CAA ATA C 5' | 5' CT TAT GGC TCT TCG TGC GGC CCA GTT TAT G 3'<br><br>3'GA ATA CCG AGA AGC ACG CCG GGT CAA ATA C 5' |
| c | 5' CC ATC CAG CAG TAC TCG AAG ACC TTC TTT 3'<br><br>3' GG TAG GTC GTC ATG AGC TTC TGG AAG AAA 5' | + 5' CC ATC CAG CAG TAC TGC AAG ACC TTC TTT 3'<br><br>- 3' GG TAG GTC GTC ATG ACG TTC TGG AAG AAA 5' |
| d | 5' CAA CTG CTT GTC GAG AAT GCC GGG CAC CGG GTC 3'<br><br>3' GTT GAC GAA CAG CTC TTA CGG CCC GTG GCC CAG 5' | 5' CAA CTG CTT GTC GAG TGC GCC GGG CAC CGG GTC3'<br><br>3' GTT GAC GAA CAG CTC ACG CGG CCC GTG GCC CAG5' |
| e | 5' TCC ACT TAC ACC ACT AGC CTG GGT GCT GG 3'<br><br>3'AGG TGA ATG TGG TGA TCG GAC CCA CGA CC 5' | 5' TCC ACT TAC ACC TGC AGC CTG GGT GCT GG 3'<br><br>3'AGG TGA ATG TGG GCA TCG GAC CCA CGA CC 5' |

*FIG. 8*

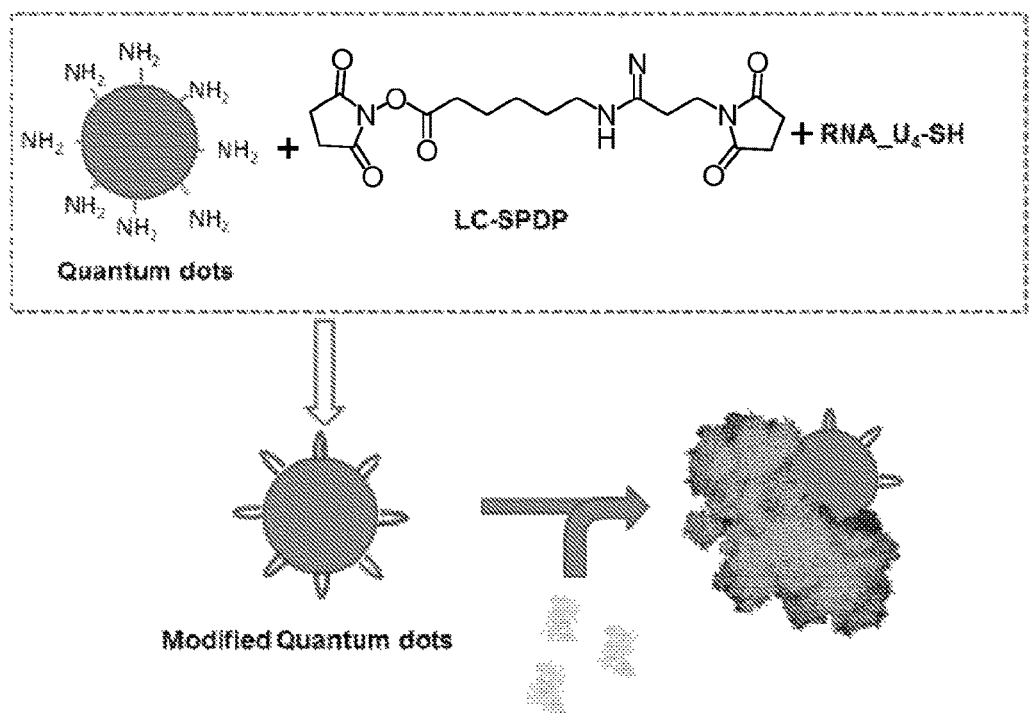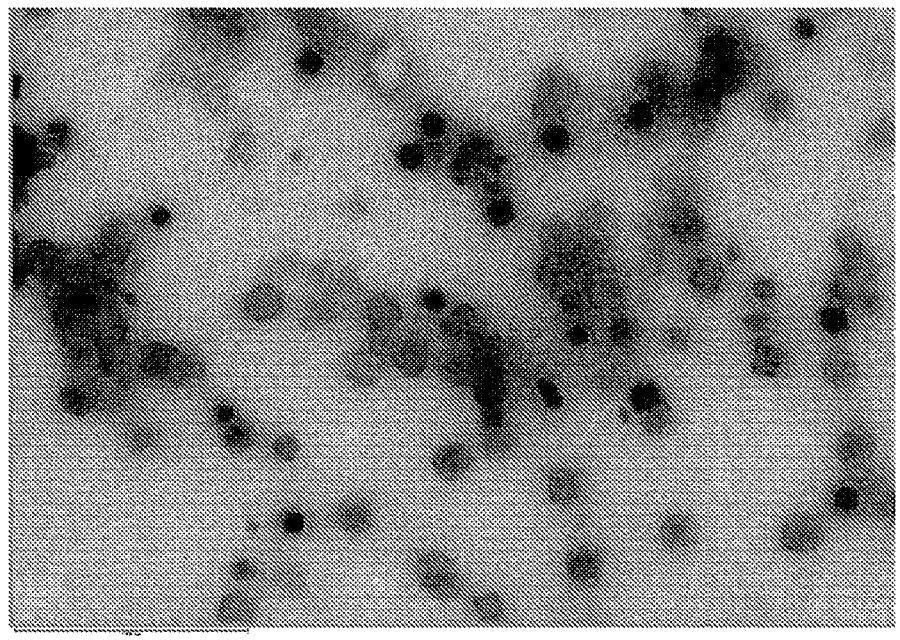
*FIG. 12*

CHEMICALLY ACTIVATED NANOCAPSID FUNCTIONALIZED FOR CANCER TARGETING

CROSS-REFERENCE TO RELATED APPLICATION

This application is a U.S. National Phase Application of PCT/US2015/031439 filed May 18, 2015 which claims the benefit of U.S. Provisional Application No. 62/000,465, filed on May 19, 2014, the contents of each are hereby incorporated by reference in the entirety for all purposes.

STATEMENT AS TO RIGHTS TO INVENTIONS MADE UNDER FEDERALLY SPONSORED RESEARCH AND DEVELOPMENT

This invention was made with government support under contract AI095382 awarded by the National Institutes of Health. The government has certain rights in the invention.

REFERENCE TO SUBMISSION OF A SEQUENCE LISTING AS A TEXT FILE

The Sequence Listing written in file SEQ-1031243.txt created on Nov. 18, 2016, 64.3 bytes, machine format IBM-PC, MS-Windows operating system, is hereby incorporated by reference in its entirety for all purposes.

BACKGROUND OF THE INVENTION

Virus-like particles (VLPs) can serve as nanocarriers for targeted delivery of diagnostics and therapeutics regimes, such as DNA/RNA and a variety of chemotherapeutics. Hepatitis E virus (HEV) is an enteric-transmitted virus that causes acute liver inflammation in humans. HEV virus-like particles (HEV VLPs) are capsid protein icosahedral cages that can be produced by expression of the major capsid protein HEV Open Reading Frame 2 (ORF2) in a eukaryotic expression system. HEV VLPs are stable in acid and proteolytic environments, a feature that is required for the natural transmission route of HEV. Thus, HEV VLPs represent a promising nano-carrier that can be exploited, e.g., for chemotherapeutic delivery, vaccination, and/or imaging.

However, in order to fulfill their promise as nano-carriers, there remains a need to develop HEV VLPs that retain their stability in acid and proteolytic environments, as well as exhibit altered VLP-surface functionality. For example, there remains a need to develop HEV VLPs that can be directed to target cells or tissue-types through surface exposed targeting moieties. The present invention fulfills this and other related needs.

BRIEF SUMMARY OF THE INVENTION

The present invention provides a cysteine modified HEV VLP scaffold for altering HEV VLP surface functionality.

In a first aspect, the present invention provides a modified capsid protein comprising a portion of hepatitis E virus (HEV) open Reading Frame 2 (ORF2) protein that is able to form an acid and proteolytically stable HEV virus like particle (VLP), wherein: the portion of HEV ORF2 comprises a P-domain of the HEV ORF2 protein; the P-domain comprises at least one surface variable loop and a C-terminus; the P-domain comprises a cysteine in the at least one surface variable loop or at the C-terminus; and the HEV ORF2 portion retains its ability to form an acid and proteolytically stable HEV VLP when the surface variable loop or C-terminal cysteine is chemically derivatized.

In some embodiments, the HEV ORF2 portion retains its ability to form an acid and proteolytically stable HEV VLP when the surface variable loop or C-terminal cysteine is alkylated, acylated, arylated, succinylated, oxidized, or conjugated to a detectable label or bioactive agent. In some embodiments, the modified capsid protein comprises an amino acid sequence at least 90%, 95%, or 99% identical, or identical, to residues 112-608 of the HEV ORF 2 protein of SEQ ID NO:1, 2, 3, 4, 5, or 6. In some embodiments, the at least one P-domain surface variable loop or C-terminal cysteine is conjugated to a detectable label. In some embodiments, the detectable label comprises a fluorophore, a superparamagnetic an MRI contrast agent, a positron emitting isotope, or a cluster of elements of group 3 through 18 having an atomic number greater than 20. In some embodiments, the cluster of elements of group 3 through 18 having an atomic number greater than 20 comprises a gold nanocluster.

In some embodiments, the at least one P-domain surface variable loop or C-terminal cysteine is conjugated to a bioactive agent. In some embodiments, the bioactive agent is a heterologous peptide. In some embodiments, the heterologous peptide is a cell targeting ligand. In some embodiments, the cell targeting ligand is a cancer cell targeting ligand. In some embodiments, the cancer cell targeting ligand is LXY30. In some embodiments, the cancer cell targeting ligand is an antibody that binds an antigen expressed on the surface of a cancer cell. In some embodiments, the modified capsid protein further comprises a second cysteine in a P-domain surface variable loop or at the C-terminus of the P-domain. In some embodiments, the second cysteine is conjugated to a chemotherapeutic.

In some embodiments, the second cysteine is conjugated to a detectable label. In some embodiments, the detectable label conjugated to the second cysteine comprises a fluorophore, a superparamagnetic label, an MRI contrast agent, a positron emitting isotope, or a cluster of elements of group 3 through 18 having an atomic number greater than 20. In some embodiments, the detectable label conjugated to the second cysteine comprising the cluster of elements of group 3 through 18 having an atomic number greater than 20 comprises a gold nanocluster.

In some embodiments, the at least one P-domain surface variable loop cysteine is alkylated, acylated, arylated, succinylated, or oxidized. In some embodiments, the at least one P-domain surface variable loop cysteine of HEV ORF2 replaces Y485, T489, S533, N573, or T586 of HEV ORF2 or the C-terminal cysteine replaces residue 608 of HEV ORF2. In some embodiments, the modified capsid protein is a component of an acid and proteolytically stable HEV VLP.

In some embodiments, the acid and proteolytically stable HEV VLP encapsulates a bioactive agent. In some embodiments, the encapsulated bioactive agent is a heterologous nucleic acid, a heterologous peptide, a detectable label, a non-proteinogenic amino acid, an oligosaccharide, a synthetic macromolecule, or a chemotherapeutic. In some embodiments, the encapsulated detectable label comprises a fluorophore, a superparamagnetic label, an MRI contrast agent, a positron emitting isotope, or a cluster of elements of group 3 through 18 having an atomic number greater than 20. In some embodiments, the encapsulated detectable label comprising the cluster of elements of group 3 through 18 having an atomic number greater than 20 comprises a gold nanocluster.

In a second aspect, the present invention provides a composition comprising the modified capsid protein of any one of the foregoing aspects or embodiments and a pharmaceutically acceptable excipient. In some embodiments, the composition comprises an HEV VLP having at least one cysteine within an HEV ORF2 P-domain surface variable loop or C-terminus that is chemically conjugated to a cell targeting ligand, a bioactive agent, or a detectable label. The chemical conjugation can result in a heterologous arrangement between the cysteine and the cell targeting ligand, bioactive agent, or detectable label.

In a third aspect, the present invention provides a nucleic acid (e.g., isolated nucleic acid) comprising a polynucleotide sequence encoding any one of the foregoing modified capsid proteins. In a fourth aspect, the present invention provides an expression cassette comprising a promoter (e.g., heterologous promoter) operably linked to a polynucleotide sequence encoding any one of the foregoing modified capsid proteins. In a fourth aspect, the present invention provides a cell isolated cell or host cell) comprising the foregoing nucleic acid or the foregoing expression cassette. In a fifth aspect, the present invention provides a cell (e.g., isolated cell or host cell) comprising any one of the foregoing modified capsid proteins. In a sixth aspect, the present invention provides au organism comprising any one of the foregoing modified capsid proteins.

In a seventh aspect, the present invention provides a method of producing a modified capsid protein comprising cultivating any one of the foregoing cells, isolated cells, or host cells under conditions suitable to permit expression of the modified capsid protein. In some embodiments, the method further comprises purifying the capsid protein. In some embodiments, the method further comprises derivatizing the at least one P-domain surface variable loop or C-terminal cysteine. In some embodiments, the derivatizing comprises acylating, alkylating, arylating, succinylating, or oxidizing the P-domain surface variable loop or C-terminal cysteine. In some embodiments, the derivatizing comprises conjugating a bioactive agent to the at least one P-domain surface variable loop or C-terminal cysteine.

In an eighth aspect, the present invention provides a method of directing an HEV VLP to a target cell comprising contacting a cell with the HEV-VLP, wherein the HEV VLP comprises any one of the foregoing modified capsid proteins, wherein the HEV VLP further comprises a cell targeting moiety having affinity for the target cell conjugated to the at least one P-domain surface variable loop or C-terminal cysteine. In some embodiments, the HEV VLP further comprises a detectable label, and the method further comprises detecting the detectable label. In some embodiments, the detecting the detectable label comprises detecting a fluorophore, superparamagnetic label, an MRI contrast agent, a positron emitting isotope, or a cluster of elements of group 3 through 18 having an atomic number greater than 20. In some embodiments, the detecting the cluster of elements of group 3 through 18 having an atomic number greater than 20 comprises detecting a gold nanocluster.

In some embodiments, the cell targeting moiety having affinity for the target cell conjugated to the at least one P-domain surface variable loop or C-terminal cysteine is a heterologous peptide comprising a cancer cell targeting ligand, and the target cell is a cancer cell. In some embodiments, the HEV VLP or a component thereof enters the cancer cell. In some embodiments, the HEV VLP encapsulates a bioactive agent, and the method comprises delivering the bioactive agent to the intracellular region of the cell. In some embodiments, the encapsulated bioactive agent is a heterologous nucleic acid, a heterologous peptide, a detectable label, a non-proteinogenic amino acid, an oligosaccharide, a synthetic macromolecule, or a chemotherapeutic. In some embodiments, the encapsulated detectable label comprises a fluorophore, a superparamagnetic label, an MRI contrast agent, a positron emitting isotope, or a cluster of elements of group 3 through 18 having an atomic number greater than 20. In some embodiments, the encapsulated cluster of elements of group 3 through 18 having an atomic number greater than 20 comprises an encapsulated gold nanocluster.

BRIEF DESCRIPTION OF THE DRAWINGS

FIG. 1: (A) Depicts the location of surface accessible flexible coil regions (P-domain surface variable loops) of HEV ORF 2, and residues Y485, T489, S533, N573, and T586, which lie within such flexible coil regions and were selected for cysteine mutation. (SEQ ID NO:13) (B) All the selected residues for cysteine mutation were located at the surface of the P-domain, with residue Y485, T489, T586 on the outmost surface, and residues S533 and N573 at side facing the VLP 5-fold axis.

FIG. 2: Characterization of chimeric HEV VLP carrying a cysteine replacement mutation. (A) The cysteine mutation at N573 appeared to allow efficient biotinylation of the chimeric VLP as compared to the other mutation sites, i.e., Y485, T489, S533, and T586, although those mutations exhibited similar biotinylation after VLP disassembly. (B) Both the wild type VLP and the chimeric VLP had similar binding affinity to monoclonal antibody HEP40-4B, while chimeric VLP exhibited decreased reactivity to monoclonal antibody HEP230.

FIG. 3: (A) The three-dimensional density map of HEV wt-VLP in complex with Fab fragments of HEP230 is displayed as isosurface along a 5-fold axis, showing extra density (arrow) in the gap of two 5-fold related protruding dimers. (B) The density agreed with the footprint of the Fab molecule. (C) Residue N573 (sphere mode) is located next to the binding site of HEP230 that (D) allows only one Fab molecule binding per 5-fold region.

FIG. 4: The schematic of the two-steps chemical conjugation process including a thiol selective reaction and a Copper Catalyzed Azide-Alkyne Cycloaddition (CuAAC) or “click chemistry” reaction to form LXY30-VLPs. Two methods have been tested in this research. Method 1: (A) The Copper Catalyzed Azide-Alkyne Cycloaddition (CuAAC) reaction between Mal-Azide and Alkyne-LXY30 to form maleimide linked LXY30 (Mal-LXY30) was done first. (B) Mal-LXY30 was then added to react with Cys of N573C-VLPs. The LXY30 and Cy5.5 decorated N573C-VLP (LXY30-VCP-Cy5.5) remained intact after all these chemical conjugation processes. Method 2: (A) The conjugation process starting by labeling maleimide linked azide (Mal-Azide) at Cys sites of N573C-VLPs through Thiol selective-reaction to build azide linked VLPs (Azide-VLPs), followed by adding LXY30-Alkyne, ascorbic acid and $CuSO_4$ to form LXY30 linked VLPs (LXY30-VLPs). (C) Damaged or dis-assembled LXY30-LVPs resulting from the conjugation process, due to the presence of reactive agents including azide, ascorbic acid and $CuSO_4$, can be separated from intact VLPs by, e.g., centrifugation, size exclusion chromatography, and the like.

FIG. 5: In vitro fluorescence data of VLP-Cy5.5 and LXY30-VLP-Cy5.5 binding to MDA-MB-231 breast cancer cells. (A) The flow cytometry data of VLP-Cy5.5 or LXY30-VLP-Cy5.5 incubated with MDA-MB-231 breast cancer cells. (B) NIR fluorescence images of LXY30-Cy5.5-VLP targeting to MDA-MB-231 cells. The signal of nuclei, which were stained by Hoechst 33342 (blue), and the signal of Cy5.5 (red) were acquired using Zeiss confocal fluorescence microscopy.

Figure 6:
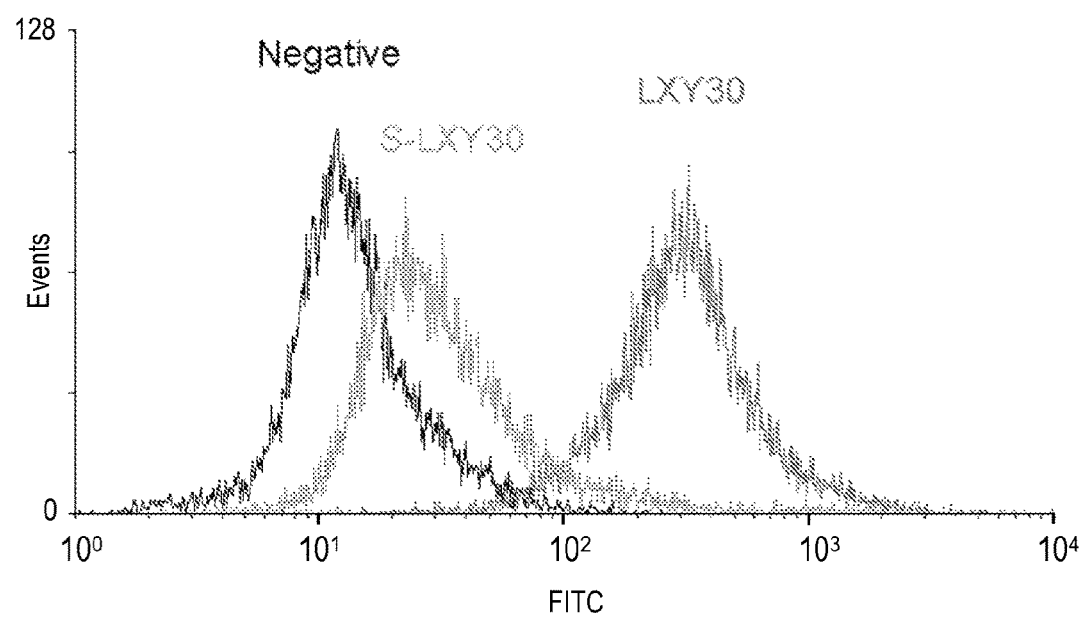
Figure 6:
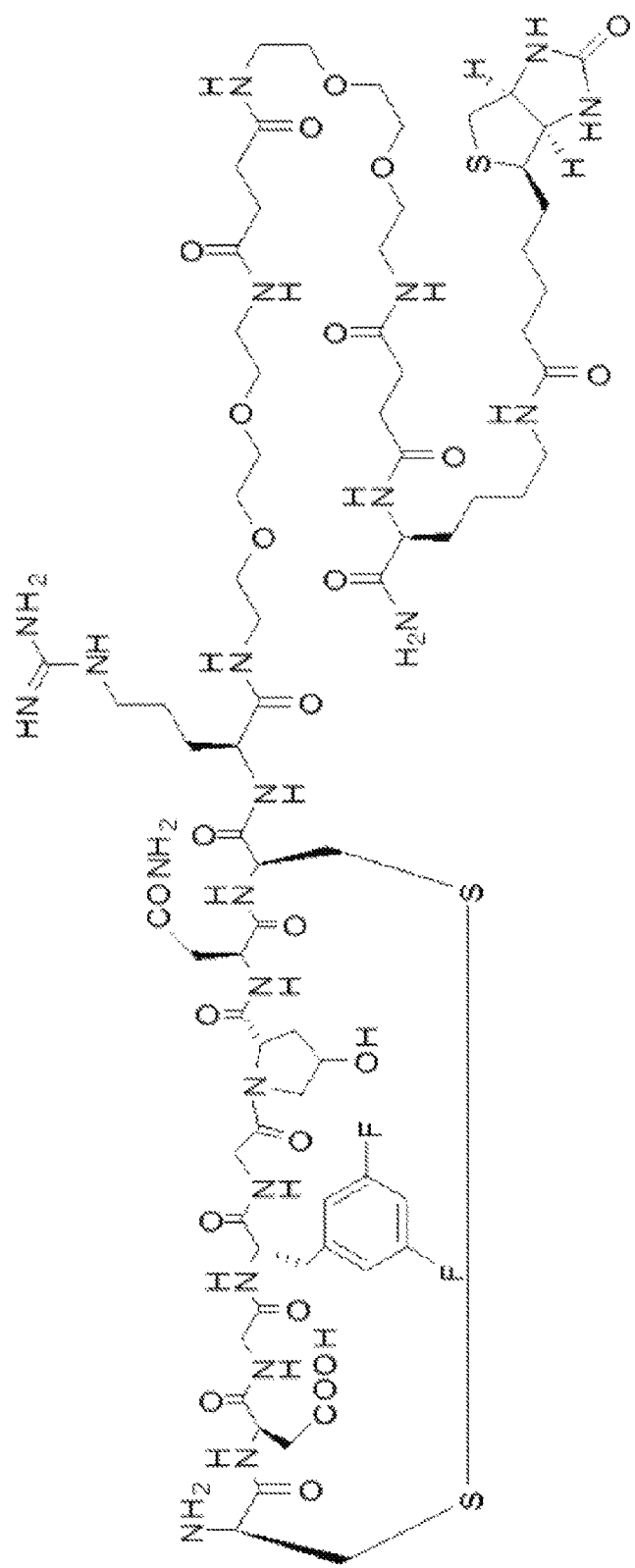

FIG. 6: The LXY30 chemical structure and its binding to U-87MG cells. Both scrambled LXY30 and LXY30 were directly conjugated to FITC, incubated with U-87MG cells, and detected by flow cytometry. Compared with the negative control, LXY30 showed obvious binding to U-87MG cells, which highly express alpha3-beta1-integrin. The scrambled LXY30 showed minimum uptake due to non-specific staining from the fluorophore FITC.

Figure 7:
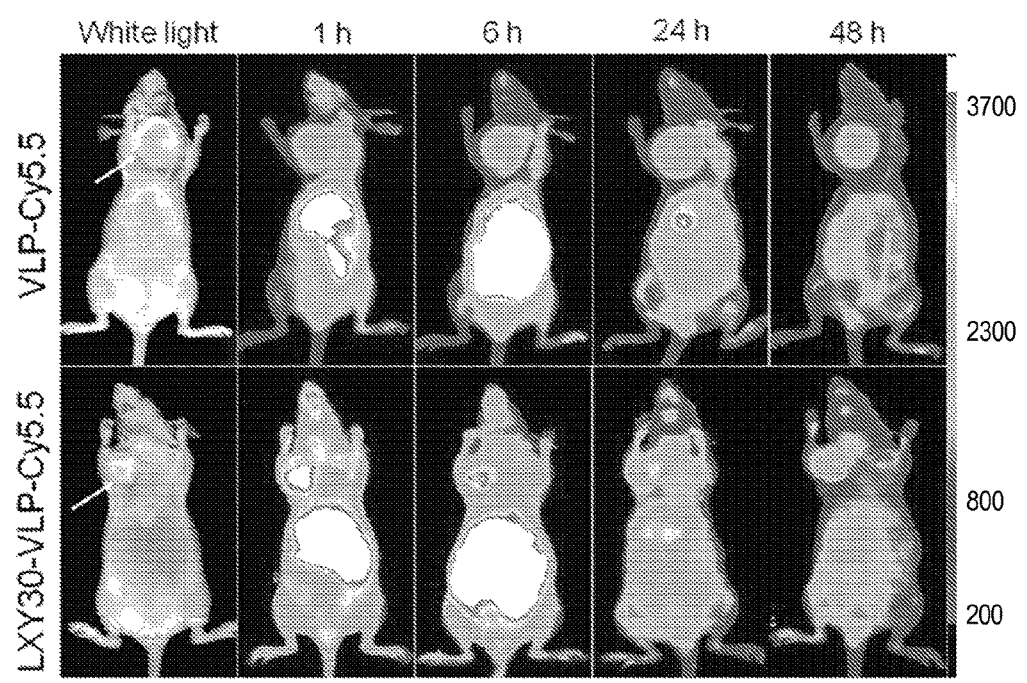

FIG. 7: In vivo NIR fluorescence images of real-time tumor targeting characteristics of VLP-Cy5.5 and LXY30-VLP-Cy5.5 nanoparticles on nude mice implanted with xenografts. The MDA-MB-231 breast cancer tumor bearing mice were injected i.v. with the equivalent amount of VLP-Cy5.5 or LXY30-VLP-Cy5.5. Arrow bars denote tumor sites. Optical imaging was obtained using a Kodak multimodal imaging system IS2000MM equipped with an excitation bandpass filter at 625 nm and an emission at 700 nm.

FIG. 8: Depicts primers designed to introduce cysteine mutations in P-domain surface variable loops of HEV ORF 2. Parental sequences with the replaced amino acid sequence bolded. Forward 5'-3' and Reverse 3'-5' primers were designed with a cysteine coding sequence to the replace parental amino acid. a-e represent Y485C (parental—SEQ ID NOs:14-15; cysteine mutation—SEQ ID NOs:16-17), T489C (parental—SEQ ID NOs:18-19; cysteine mutation—SEQ ID NOs:20-21), S533C (parental—SEQ ID NOs:22-23; cysteine mutation—SEQ ID NOs:24-25), N573C (parental—SEQ ID NOs:26-27; cysteine mutation—SEQ ID NOs:28-29), and T586C (parental—SEQ ID NOs:30-31; cysteine mutation—SEQ ID NOs:32-33), respectively.

FIG. 9: Depicts the location of the surface variable loops and C-terminal residues of the P-domain of the HEV ORF2 capsid protein. (A) Depicts a schematic diagram of P-domain surface variable loops of HEV ORF 2 capsid protein. (B) Depicts the location of the P-domain surface variable loop residues and C-terminal residue on an HEV VLP. One or more cysteines can be positioned within the indicated loop or C-terminal residues for conjugation to a molecular payload.

FIG. 10: Schematic depicting the application of chimeric HEV ORF2 VLPs as nanocarriers for drug delivery. The periodicity of the capsid, the presence of surface-accessible amino acids with reactive moieties, and the tolerance of a single chain version of the capsid protein dimer to diverse peptide insertions enable dense, repetitive display of targeting ligands either by chemical conjugation or genetic insertion, and display of aptamers, glycoproteins, etc., by chemical conjugation. HEV ORF2 VLPs also possess relatively large interior volumes that can be loaded with a variety of materials, including DNA plasmids. In comparison to other virus-like particles, HEV ORF2 VLPs possess strong structural plasticity, with a stability switch sensitive to calcium concentration.

FIG. 11: Cys-VLP conjugation to sulfur protected $Au_{102}$. (A) Depicts two methods for covalent gold conjugation to Cys-VLP. (B) Cys-VLP direct ligand exchange with $Au_{102}(pMBA)_{44}$. (C) Cys-VLP maleimide conjugation with $Au_{102}$—$C_6$-Maleimide. (D) Cryo-EM Cys-VLP with $Au_{102}(pMBA)_{44}$ and the processed 3-D reconstruction.

FIG. 12: Schematic depicting the process used to encapsulate quantum dots in an HEV ORF2 VLP (top). Transmission electron microscope image of ferrite packaged VLPs showing darker intensity compared to package-free VLPs.

DETAILED DESCRIPTION OF THE INVENTION

I. Definitions

As used in this specification and the appended claims, the singular forms "a," "an," and "the" include plural reference unless the context clearly dictates otherwise.

"Hepatitis E virus" or "HEV" refers to a virus, virus type, or virus class, which i) causes water-borne, infectious hepatitis; ii) is distinguished from hepatitis A virus (HAV), hepatitis B virus (HBV), hepatitis C virus (HCV), or hepatitis D virus (HDV) in terms of serological characteristics; and iii) contains a genomic region that is homologous to a 1.33 kb cDNA inserted in pTZKF1(ET1.1), a plasmid embodied in a *E. coli* strain deposited in American Type Culture Collection (ATCC) with accession number 67717.

The terms "capsid protein" and "modified capsid protein," with reference to HEV, refer to a mature or modified (e.g., truncated, recombinantly mutated, or chemically derivatized) HEV open reading from 2 (ORF2) polypeptide. As used herein, reference to such ORF2 polypeptides or proteins is meant to include the full-length polypeptide, and fragments thereof, and also include any substitutions, deletions, or insertions or other modifications made to the ORF2 proteins. The capsid proteins must be capable of forming a virus like particle (VLP). Typically the capsid protein contains at least residues 112-608 of HEV ORF2, although the capsid protein can tolerate various additional substitutions, deletions, or insertions so long as they are tolerated without abrogating VLP formation.

In one embodiment, the term "modified capsid protein" refers to a capsid protein, or portion thereof, in which a surface variable loop of the P-domain of HEV ORF2 is modified to incorporate one or more cysteines that are not otherwise present in the wild-type capsid protein sequence. Alternatively, or additionally, the term "modified capsid protein" refers to a capsid protein, or portion thereof, in which the C-terminus (e.g., position 608) of HEV ORF2 is modified to incorporate one or more cysteines that are not otherwise present in the wild-type capsid protein sequence. Alternatively, or additionally, the term "modified capsid protein" refers to a capsid protein, or portion thereof, in which a cysteine (e.g., a cysteine of a surface variable loop of the P-domain of HEV ORF 2 or a cysteine recombinantly introduced at position 608) is chemically derivatized to covalently conjugate to the protein at least one heterologous atom or molecule. The cysteine can be inserted such that the HEV ORF2 protein length is increased, or the cysteine can replace one or more residues of a P-domain surface variable loop and/or C-terminus.

Generally, modified capsid proteins retain the ability to form HEV VLPs. In some cases, the one or more cysteines are conjugated to a bioactive agent (e.g., a cell-targeting ligand such as the peptide LXY30). P-domain surface variable loops include one or more of e.g., residues 475-493; residues 502-535; residues 539-569; residues 572-579; and residues 581-595 of HEV ORF 2 (SEQ ID NO:1, 2, 3, 4, 5, or 6). P-domain surface variable loops further include the residues of polypeptides comprising an amino acid sequence that is at least about 80%, 85%, 90%, 95%, 99%, or more identical to one or more of SEQ ID NOS:1, 2, 3, 4, 5, or 6 and that correspond to one or more of residues 475-493;

residues 502-535; residues 539-569; residues 572-579; and residues 581-595 of SEQ ID NOS:1, 2, 3, 4, 5, or 6.

As used herein, the term "virus-like particle" (VLP) refers to an icosahedral shell (e.g., T1 or T3) formed by a capsid protein. VLPs are not infectious due to the lack of a viral genome. "VLP" refers to a nonreplicating icosahedral viral shell, derived from hepatitis E virus capsid protein HEV ORF2, a portion thereof. VLPs can form spontaneously upon recombinant expression of the protein in an appropriate expression system. In some embodiments, the VLP is formed from a modified capsid protein, e.g., a capsid protein containing one or more cysteine residues in a surface variable loop of HEV ORF2, or a portion thereof. An HEV VLP can contain a mixture of modified and/or unmodified HEV ORF2 proteins.

The term "acid and proteolytically stable" in the context of an HEV VLP refers to an HEV VLP that is resistant to the acid and proteolytic environments of a mammalian digestive system. Methods of assessing acid and proteolytic stability are described in Jariyapong et al., 2013, and include, but are not limited to subjecting an HEV VLP to an acid (e.g., pH of, or of about, 6, 5.5, 5, 4.5, 4, 3.5, 3, 2.5, or 2) and/or proteolytic environment trypsin and/or pepsin) and examining the contacted HEV VLP by electron microscopy, gel filtration chromatography, or other suitable method to determine whether the quaternary structure (e.g., T=1, T=3, icosahedron, dodecahedron, etc.) of the HEV VLP is retained. A population of HEV VLPs (e.g., modified or unmodified) can be incubated under acid and/or proteolytic conditions for a suitable period of time (e.g., for at least, or for at least about, 1, 2, 3, 4, 5, 10, 15, 20, 30, 45, or 60 minutes) and then tested to determine the extent of quaternary structure retention. In this context, an acid and proteolytically stable modified. HEV VLP refers to a modified HEV VLP that when incubated as a population of VLPs under acid and/or proteolytic conditions and assayed by electron microscopy, at least 10%, 25%, 50%, 75%, 90%, 95%, 99%, or 100% of the VLPs of the population retain their quaternary structure.

Alternatively, the HEV VLP can be delivered to a subject via an oral route and the efficiency of delivery assessed by detecting and/or quantifying: (i) an immune response to an antigen within the HEV VLP; (ii) a detectable label conjugated to, recombinantly introduced into, or encapsulated by the HEV VLP; or (iii) a biological response due to delivery to a cell of a bioactive agent associated with (e.g., recombinantly introduced into, conjugated to, or encapsulated by) the HEV VLP. In this context, an acid and proteolytically stable modified HEV VLP refers to a modified HEV VLP that retains at least 10%, 25%, 50%, 75%, 90%, 95%, 99%, or 100% of the oral delivery efficacy and/or cell entry activity of an unmodified HEV VLP.

The term "heterologous" as used in the context of describing the relative location of two elements, refers to the two elements such as nucleic acids (e.g., promoter or protein encoding sequence) or proteins (e.g., an HEV ORF2 protein, or portion thereof, or modified capsid protein and another protein) that are not naturally found in the same relative positions. Thus, a "heterologous promoter" of a gene refers to a promoter that is not naturally operably linked to that gene.

Hepatitis E virus (HEV) is known to cause severe acute liver failure. HEV belongs to the genus *Hepevirus* in the family Hepeviridae. HEV contains a single-stranded positive-sense RNA molecule of approximately 7.2-kb. The RNA is 3' polyadenylated and includes three open reading frames (ORF). ORF1 encodes viral nonstructural proteins, located in the 5' half of the genome. ORF2 encodes a protein-forming viral capsid, located at the 3' terminus of the genome. ORF3 encodes a 13.5-kDa protein, overlapped with C-terminus of ORF1 and N-terminus of ORF2. ORF3 is associated with the membrane as well as with the cytoskeleton fraction.

The term "encapsulation," or "encapsulated," as used herein refers to the envelopment of a heterologous substance, such as a heterologous nucleic acid or protein, a chemotherapeutic, an imaging agent, a ferrite nanoparticle etc., within the VLPs defined herein.

The term "bioactive agent" refers to any agent, drug, compound, or mixture thereof that targets a specific biological location (targeting agent) and/or provides some local or systemic physiological or pharmacologic effect that can be demonstrated in vivo or in vitro. Non-limiting examples include drugs, hormones, vaccines, antibodies, antibody fragments, vitamins and co factors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, DNA, cDNA, antisense constructs, ribozymes, etc.).

A "pharmaceutically acceptable" or "pharmacologically acceptable" material is one that is not biologically harmful or otherwise undesirable, i.e., the material may be administered to an individual along with the capsid protein or the HEV VLPs or the compositions of the present invention without causing any undesirable biological effects. Neither would the material interact in a deleterious manner with any of the components of the composition in which it is contained.

The term "excipient" refers to any essentially accessory substance that may be present in the finished dosage form of the composition of this invention. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

The term "adjuvant" refers to a compound that, when administered in conjunction with an antigen, augments the immune response to the antigen, but does not generate an immune response to the antigen when administered alone. Adjuvants can augment an immune response by several mechanism including lymphocyte recruitment, stimulation of B and/or T cells, and stimulation of macrophages.

An "immunogenic response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γΔ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

As used herein, the term "host" refers to humans as well as other animals.

The term "mucosal delivery" relates to delivery of a composition to a mucous membrane, such as the mucosa of the gastro-intestinal tract (e.g., the buccal or labial mucosa) or the mucosa of the respiratory tract (e.g., the nasal mucosa).

II. Production and Purification of Modified Capsid Proteins and VLP Formation

One aspect of the invention relates to methods for production and purification of capsid proteins and VLPs derived therefrom (See, Expression and self-assembly of empty virus-like particles of hepatitis E virus. Li T C, Yamakawa Y, Suzuki K, Tatsumi M, Razak M A, Uchida I, Takeda N, Miyamura T., J Virol. 1997 October; 71(10):7207-13. Essential elements of the capsid protein for self-assembly into empty virus-like particles of hepatitis E virus. Li T C, Takeda N, Miyamura T, Matsuura Y, Wang J C, Engvall H, Hammar L, Xing L, Cheng R H. J Virol. 2005 October; 79(20):12999-3006. Niikura M et al, Chimeric recombinant hepatitis E virus-like particles as an oral vaccine vehicle presenting foreign epitopes. Virology 2002; 293: 273-280). In one embodiment, the capsid proteins are modified capsid proteins and the VLPs derived therefrom are cysteine modified HEV VLPs. For example, the modified capsid proteins contain one or more cysteine residues in a surface variable loop of HEV ORF2, or a portion thereof.

Various expression systems can be used to express the capsid proteins of the present invention. Examples of expression systems useful for the production of virus-like particles of the present invention include, but are not limited to, bacterial expression system (e.g., *Escherichia coli*), insect cells, yeast cells and mammalian cells. Preferred expression system of the present invention includes baculovirus expression systems using insect cells. General methods, for example, for handling and preparing baculovirus vectors and baculoviral DNA, as well as insect cell culture procedures, are outlined in A Manual of Methods for Baculovirus Vectors and Insect Cell Culture Procedures.

The capsid proteins of the present invention can be cloned into the baculovirus vector, and used to infect appropriate host cells (see, for example, O'Reilly et al., "Baculovirus Expression Vectors: A Lab Manual," Freeman & Co. 1992.). An insect cell (e.g., Sf9 or Tn5) can be transformed with a transfer vector containing polynucleic acids which encodes the capsid proteins of the invention. The transfer vector includes, for example, linearized baculovirus DNA and a plasmid containing the desired polynucleotides. The host cell line may be co-transfected with the linearized baculovirus DNA and a plasmid order to make a recombinant baculovirus.

Purification of the virus-like particles of the present invention can be carried out according to the standard technique in the art (See, Li T C, et al., J Virol. 1997 October; 71(10):7207-13. Li T C, et al., J. Virol. 2005 October; 79(20):12999-3006. Niikura M et al, Virology 2002; 293: 273-280). The purified VLPs are then resuspended in a suitable buffer.

In some embodiments, the modified capsid proteins or VLPs derived therefrom can be chemically conjugated to one or more bioactive agents. For example, one or more cysteine residues of the capsid proteins can be acylated, alkylated, arylated, succinylated, or oxidized using methods known in the art. In some cases, the one or more cysteine residues can be conjugated using a maleimide functional group to covalently conjugate a bioactive agent to the thiol moiety of the cysteine. In some cases, the bioactive agent can be modified to introduce a maleimide functional group using CLICK chemistry. For example, an alkyne derivative of the bioactive agent can be contacted with a maleimide-azide in the presence of $CuSO_4$ and ascorbic acid to produce a maleimide bioactive agent. The maleimide can then be contacted with the one or more cysteines of the modified capsid protein to covalently link the two molecules. In some cases, the conjugating is performed on capsid protein that is not assembled into a VLP (e.g., in the presence of EDTA, EGTA, and/or a reducing agent such as DTT or betamercaptoethanol). In some cases, the conjugating is performed on capsid protein that is assembled into a VLP.

III. Encapsulation of Bioactive Agents

Another aspect of the invention relates to the encapsulation of one or more bioactive agents in HEV virus-like particles (e.g., cysteine modified HEV VLPs) (See, DNA vaccine-encapsulated virus-like particles derived from an orally transmissible virus stimulate mucosal and systemic immune responses by oral administration, Gene Therapy 2004. 11, 628-635. S Takamura, M Niikura, T-C Li, N Takeda, S Kusagawa, Y Takebe, T Miyamura and Y Yasutomi). Any standard technique in the art can be used to encapsulate a heterologous nucleic acid, protein, polypeptide, chemotherapeutic, imaging agent, nanoparticle, etc. into the VLPs of the present invention. The general procedure involves (1) disassembling the VLPs formed by the capsid protein according to the present invention; and (2) reconstructing the VLPs in the presence of the bioactive agent. A skilled artisan would recognize that it is preferred to have purified VLPs before the encapsulation procedure. It is particularly preferred to have the VLPs depleted of or substantially depleted of, any undesired materials (e.g., nucleic acids) before the encapsulation procedure.

Disassembly of VLPs can be carried out using any standard technique in the art, Reconstituted virus-like particle can be produced under physiological conditions (See, US Patent Publication No.: 20080131928). Often, disassembly of virus-like particles requires an agent to disrupt the assembly of VLPs, such as a reducing agent or a chelating agent (See, US Patent Publication No.: 20040152181). A skilled artisan would recognize that factors and conditions that affect assembly and disassembly include: pH, ionic strength, posttranslational modifications of viral capsid proteins, disulfide bonds, and divalent cation bonding, among others. For example, the importance of cation bonding, specifically calcium, in maintaining virion integrity has been shown for polyomavirus (Brady et al., J. Virol, 23:717-724, 1977), and rotovirus (Gajardo et al., J. Virol, 71:2211-2216, 1997). Also, disulfide bonds appear to be significant for stabilizing polyomavirus (Walter et al., Cold Spring Har Symp. Quant. 39:255-257, 1975; Brady et al., J. Virol, 23:717-724, 1977);

and SV40 viruses (Christansen et al., J. Virol, 21:1079-1084, 1977). Also, it is known that factors such as pH and ionic strength influence polyomavirus capsid stability, presumably by affecting electrostatic interactions (Brady et al., J. Virol, 23:717-724, 1977; Salunke et al., Cell, 46:895-904, 1986; Salunke et al., Biophys. J, 56:887-900, 1980). Also, it is known that post-translational modifications of some viral capsid proteins may affect capsid stability and assembly, e.g., glycosylation, phosphorylation, and acetylation (Garcea et al., Proc. Natl. Acad. Sci. USA, 80:3613-3617, 1983; Xi et al., J. Gen. Virol, 72:2981-2988, 1991). Thus, there are numerous interrelated factors which may affect capsid stability, assembly and disassembly.

Preferably, the VLPs of the present invention is disassembled by the removal of calcium ions (See, Touze A, Coursaget P. In vitro gene transfer using human papillomavirus-like particles. Nucleic Acids Res 1998; 26:1317-1323; Takamura et al., DNA vaccine-encapsulated virus-like particles derived from an orally transmissible virus stimulate mucosal and systemic immune responses by oral administration. Gene Therapy 2004; 11:628-635). According to the present invention, a reducing agent or a chelating agent or both are used to disassemble the VLPs. Various reducing agents can be used. Preferred embodiments of the reducing agents include, but are not limited to, dithiothreitol (DTT). Various chelating agents can be used, e.g., ethylene glycol tetraacetic acid (EGTA) or ethylenediaminetetracetic acid (EDTA). Examples of VLP disassembly conditions include, but are not limited to, the following: purified VLPs were disrupted by incubation of a buffer containing 50 mM Tris-HCl (pH 7.5), 150 mM NaCl, 1 mM EGTA and 20 mM dithiothreitol for 30 minutes.

A skilled artisan would also recognize that complete disassembly of the VLPs is not required, although preferred, to encapsulate a bioactive agent. An artisan would also recognize that, on other occasions, it is preferred to have partial disassembly of the VLPs. According to the present invention, the conditions for the partial disassembly of the VLPs can be controlled to still allow efficient encapsulation of a bioactive agent. Partial disassembly of the VLPs can be achieved by treatment of VLPs with reducing agents alone (e.g., 20 mM DTT) (Sapp et al, J. Gen. Virol., 76:2407-2412, 1995.). According to the present invention, once the VLPs are disassembled completely or partially, encapsulation of a bioactive agent can be carried out by reassembling the VLPs in the presence of the bioactive agent. In some cases, it can be advantageous to utilize a bioactive agent having a net negative charge to enhance encapsulation. For example, nucleic acids have a net negative charge and can be preferentially encapsulated as compared to compounds that have a positive or neutral charge.

In some embodiments of the present invention, reassembly of the VLPs is achieved by re-supplementation of calcium ions to the disrupted VLPs. Alternatively, reassembly of the VLPs is achieved by removal of the reducing agents or the chelating agents. Optionally, factors such as pH and ionic strength, other factors described in the present invention, can be adjusted to achieve efficient reassembly of the VLPs and efficient encapsulation of the bioactive agent.

In some embodiments, encapsulation is performed as follows: Following 30 min of incubation at room temperature, a bioactive agent in 50 mM Tris-HCl buffer (pH 7.5) and 150 mM NaCl is added to the disrupted VLP preparation. The disrupted VLP preparation is then refolded by incubation for 1 h with increasing concentrations of $CaCl_2$ up to a final concentration of 5 mM. VLPs are pelleted by ultracentrifugation and resuspended in 10 mM potassium-MES buffer (pH 6.2). To estimate the amounts of encapsulated agent, refolded and purified VLPs are purified from any unencapsulated bioactive agent and disrupted with EGTA (1 mM). Absorbance of the supernatant, or other suitable methods can be used for detection of the bioactive agent.

In some embodiments, the bioactive agent or imaging agent to be encapsulated is conjugated to an encapsidation signal. For example, an RNA element corresponding to codons 35-59 of HEV open reading frame 1 is a powerful encapsidation signal, allowing specific interaction in vitro with HEV capsid protein, including truncated and/or cysteine modified versions of HEV ORF2 VLP as described herein. To use VLP as a carrier for therapeutic or imaging agents, chemical linkers (e.g., LC-SPDP or aptamer, telodendrimers) that tag the agent (e.g., chemotherapeutic) with an HEV encapsidation signal like the foregoing RNA element can be used prior to the capsid self-assembly.

In some embodiments, a detectable label (imaging agent) is encapsulated. The detectable label can be a moiety renders a molecule to which it is attached to detectable by a variety of mechanisms including chemical, enzymatic, immunological, or radiological means. Some examples of detectable labels include fluorescent molecules (such as fluorescein, rhodamine, Texas Red, and phycoerythrin) and enzyme molecules (such as horseradish peroxidase, alkaline phosphatase, and β galactosidase) that allow detection based on fluorescence emission or a product of a chemical reaction catalyzed by the enzyme. Radioactive labels involving various isotopes, such as 3H, 125I, 35S, 14C, or 32P, can also be attached to appropriate molecules to enable detection by any suitable methods that registers radioactivity, such as autoradiography. See, e.g., Tijssen, "Practice and Theory of Enzyme Immunoassays," Laboratory Techniques in Biochemistry and Molecular Biology, Burdon and van Knippenberg Eds., Elsevier (1985), pp. 9 20. An introduction to labels, labeling procedures, and detection of labels can also be found in Polak and Van Noorden, Introduction Immunocytochemistry, 2d Ed., Springer Verlag, NY (1997); and in Haugland, Handbook of Fluorescent Probes and Research Chemicals, a combined handbook and catalogue published by Molecular Probes, Inc. (1996). Further detectable labels include, but are not limited to, superparamagnetic labels (e.g., ferrite), contrast enhancing reagents e.g., MRI contrast agents), atom-clusters (e.g., gold clusters), and the like.

In some embodiments, a bioactive agent is encapsulated. In some cases, the bioactive agent is a chemotherapeutic. Suitable chemotherapeutics include, but are not limited to, cytotoxic drugs. Examples of cytotoxic drugs which may be used in the present invention include: alkylating drugs, such as cyclophosphamide, ifospfamide, chlorambucil, melphalan, busulfan, lomustine, carmustine, chlormethhine (mustine), estramustine, treosulfan, thiotepa, mitobronitol; cytotoxic antibiotics, such as doxorubicin, epirubicin, aclarubicin, idarubicin, daunorubicin, mitoxantrone (mitozantrone), bleomycin, dactinomycin and mitomycin; antimetabolites, such as methotrexate, capecitabine; cytarabine, fludarabine, ibine, gemcitabine, fluorouracil, raititrexed (tomudex), mercaptopurine, tegafur and tioguaninc; vinca alkaloids, such as vinblastine, vincristine, vindesine, vinorelbine and etoposide; other neoplastic drugs, such as amsacrine, altetarmine, crisantaspase, dacarbazine and temozolomide, hydroxycarbamide (hydroxyurea), pentostatin, platinum compounds including: carboplatin, cisplatin and oxaliplatin, porfimer sodium, procarbazine, razoxane; taxanes including: docetaxel and paclitaxel; topoisomerase I inhibitors including inotecan and topotecan, trastuzumab, and tretinoin. In some cases, one or more of the foregoing imaging agents and/or bioactive agents, or a combination thereof, can additionally or alternatively be conjugated to a cysteine (e.g., recombinantly introduced cysteine) in a P-domain surface variable loop or C-terminus via a thiol linkage. In some cases, one or more of the foregoing imaging agents and/or bioactive agents, or a combination thereof, can additionally or alternatively be conjugated to a second cysteine (e.g., recombinantly introduced cysteine) in a P-domain surface variable loop or C-terminus via a thiol linkage.

The size of the VLPs can vary when different constructs of the capsid protein are used. For example, the N-terminal portion of the capsid protein can be adjusted to increase or decrease the size and encapsulation capacity of the VLPs. In some embodiments of the invention, in constructing the HEV VLP, a portion of HEV ORF 3 protein fused to the N-terminal of a portion of HEV ORF 2 proteins is utilized to adjust the size of the VLPs. Typically, the HEV VLP is formed from a portion of HEV ORF2 having at least residues 112-608 of HEV ORF 2.

IV. Pharmaceutical Compositions, Formulations and Administration

The present invention also provides pharmaceutical compositions or physiological compositions comprising a cysteine modified HEV VLP formed by the capsid protein of the present invention. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery. See Langer, *Science* 249: 1527-1533 (1990).

The compositions of the present invention can be administered to a host with an excipient. Excipients useful for the present invention include, but are not limited to, vehicles, binders, disintegrants, fillers (diluents), lubricants, glidants (flow enhancers), compression aids, colors, sweeteners, preservatives, suspending/dispersing agents, film formers/coatings, flavors and printing inks.

Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette Guerin) and *Corynebacterium parvum*. Such adjuvants are also well known in the art. Further adjuvants that can be administered with the compositions of the invention include, but are not limited to, Monophosphoryl lipid immunomodulator, AdjuVax™ 100a, QS 21, QS 18, CRL1005, Aluminum salts, MF 59, and Virosomal adjuvant technology. The adjuvants can also comprise a mixture of these substances.

One advantage of the compositions and methods of the present invention is that the compositions of the present invention can be administered to stimulate immune response without an adjuvant. Therefore, the compositions of the present invention are in some cases administered to a host without an adjuvant.

Another advantage of the present invention is that the compositions of the present invention are suitable for oral delivery. Because mucosa surfaces are inter-connected, stimulation of one mucosal surface by an antigen can induce mucosal immunity not only on the directly stimulated surface, but also on the distant ones. For example, oral delivery of the compositions of the present invention can protect against respiratory and genital-urinary infections. The compositions of the present invention are also suitable for mucosal delivery, such as delivery to the buccal or labial mucosa or the respiratory tract mucosa, including the nasal mucosa.

The pharmaceutical compositions of the present invention can be administered by various routes, e.g., oral, subcutaneous, transdermal, intradermal, intramuscular, intravenous, or intraperitoneal. The preferred routes of administering the pharmaceutical compositions are oral delivery at daily doses of about 0.01-5000 mg, preferably 5-500 mg. The appropriate dose may be administered in a single daily dose or as divided doses presented at appropriate intervals, for example as two, three, four, or more subdoses per day.

For preparing pharmaceutical compositions of the present invention, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., a chimeric virus-like particles with an encapsulated nucleic acid. In tablets, the active ingredient (a chimeric virus-like particles with an encapsulated nucleic acid) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound with encapsulating material as a carrier providing a capsule in which the active component (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., a chimeric virus-like particles with an encapsulated nucleic acid) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by suspending the active component (e.g., a chimeric virus-like particles with an encapsulated nucleic acid) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 9, more preferably from 5 to 8, and most preferably from 6 to 7.

The pharmaceutical compositions of the present invention can be administered for prophylactic and/or therapeutic treatments. In therapeutic applications, compositions are administered to a patient already suffering from a condition in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of the composition per day for a 70 kg patient, with dosages of from about 5 mg to about 500 mg of the composition per day for a 70 kg patient being more commonly used.

In prophylactic applications, pharmaceutical compositions of the present invention are administered to a patient susceptible to or otherwise at risk of developing a disease or condition, in an amount sufficient to delay or prevent the onset of the symptoms. Such an amount is defined to be a "prophylactically effective dose." In this use, the precise amounts of the composition again depend on the patient's state of health and weight, but generally range from about 0.1 mg to about 2,000 mg of the inhibitor for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should provide a quantity of composition of the present invention sufficient to effectively stimulate immune response in the patient, either therapeutically or prophylactically.

All patents, patent applications, and other publications, including GenBank Accession Numbers, cited in this application are incorporated by reference in the entirety for all purposes.

V. Examples

The following examples are provided by way of illustration only and not by way of limitation. Those of skill in the art will readily recognize a variety of non-critical parameters that could be changed or modified to yield essentially the same or similar results.

Example 1: Chemically Activatable Viral Capsid Functionalized for Cancer Targeting Introduction Virus-like particles (VLPs) have been proposed for use as nanocarriers to display foreign epitopes and/or deliver small molecules, a method for combating many diseases.[1] This application relies mainly on the property of self-assembly as well as the ease of genetic modifications, to fulfill the designed application for the given VLP. Compared to genetic engineering, chemical conjugation of foreign peptides to VLP displays a significant advantage because it allows a great variety of entities, such as peptide or oligosaccharide, to be conjugated to the surface of virus like particles in modulated and flexible manner without alteration of VLP assembly.

Hepatitis E virus (HEV) is composed of a non-enveloped icosahedral capsid, enclosing a single stranded RNA genome of 7.2 kilo bases. The major capsid protein is encoded by the second open reading frame (ORF2) and is essential not only for virus assembly, but also for immunogenicity and host interaction.[6] The recombinant capsid protein (PORF2) is able to self-assemble into VLPs when expressed in insect cells after deletion of 111 amino acids from the N-terminal end and 52 amino acids from the C-terminal end. PORF2 folds into three domains: S (shell; amino acids 118-317), M (middle; amino acids 318-451) and P (protruding; amino acids 452-606).[9-11] Recombinant HEV-VLPs consists of 60 copies of PORF2, in which the S-domain possesses typical eight anti-parallel folding and stabilizes icosahedral shell and the P-domain protrudes as a surface spike that contributes greatly to HEV antigenicity. With three-domain modularity, HEV-VLP can be readily manipulated to, e.g., alter antigenicity, reduce the size from a T3 icosahedral particle to a T1 icosahedral particle, and/or modify the sequence at the P-domain without interfering, with HEV-VLP assembly.

Like the native virus, HEV-VLP can be stable in acidic environment[15] and resistant to proteolytic digestion,[13] thus it poses a great advantage as an oral delivery vehicle. In fact, oral administration of HEV-VLP elicits both systemic and mucosal immunity without eliciting tolerance, and thus can provide protective immunity against HEV challenge in non-human primates[16] Chimeric VLPs carrying a foreign epitope are able to elicit mucosal and systemic antibodies against both HEV and the foreign epitope after oral administration.[14] Importantly, HEV-VLP can orally deliver plasmid DNA to the epithelial cells of the small intestine and induce antibody and cytotoxic T lymphocyte (CTL) responses against the plasmid encoded antigen.[17] All of these studies have established the feasibility of utilizing HEV-VLP for mucosal delivery, in a route resembling virus native transmission.

Cancer theranostics requires direct contact of drug with pathological foci; therefore, a capsule carrying specific ligands is preferential for targeted delivery of anti-cancer reagents. Current delivery system based on liposome and/or organic polymers such as polyethylene glycol gives feasible yet low specificity cancer cell targeting. In this study, we created an HEV-VLP based theranostic capsule whose entry specificity can be defined by the VLP-conjugated targeting ligand. The modified HEV-VLP after conjugation with LXY30, a ligand peptide with a high affinity for human malignant breast tumor cells,[18] showed specific targeting to breast tumor cell both in vitro and in vivo, indicating that delivery route of virus-like particle can be manipulated to facilitate targeted delivery of chemotherapeutic drugs or siRNA to pathologic foci.

Results

Cysteine Replacement at the Surface Loops of the P-Domain

Alkylation and acylation are the two traditional bioconjugation methods that are used to covalently modify virus particles by attaching a ligand at amine group of lysine or thiol group on cysteine, respectively. HEV ORF2 naturally has four lysine residues that are exposed on the surface of the P-domain. An external ligand will randomly couple with one or more of the four lysine residues. In order to avoid this random coupling, it was decided to genetically introduce a cysteine replacement to the surface of the P-domain, which allowed acylation to be used to site-specifically anchor the external ligand, while alkylation was used for conjugation of a fluorescent dye to surface lysine residues.

Figure 2:
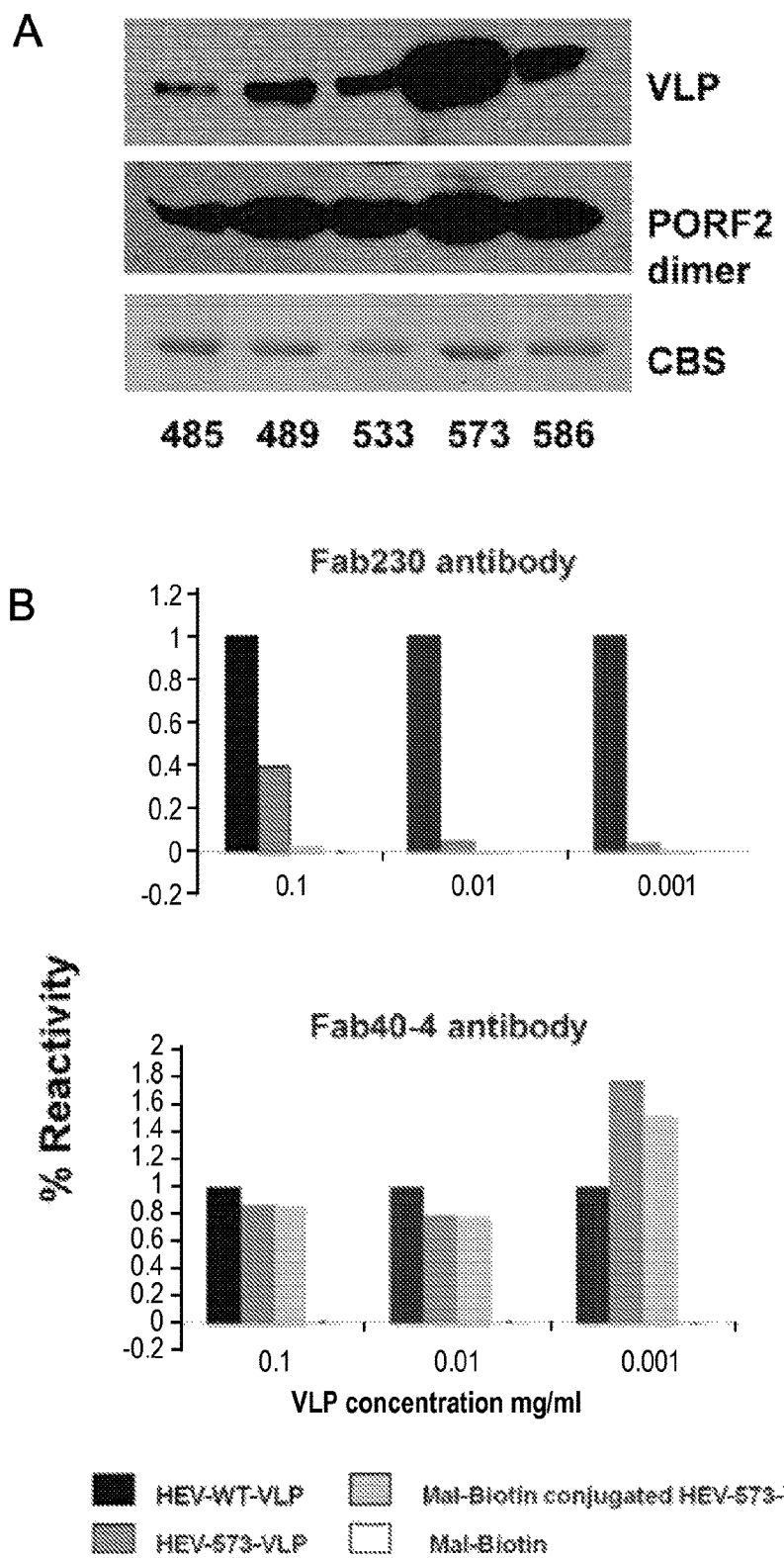

Five sites for cysteine replacement from the surface variable loops of the P-domain were selected based on the known structure of HEV-VLP (FIG. 1A).[10] These sites were selected based on their location as well as the feasibility of sequence mutation to minimize any possible distortion of VLP assembly. As expected, individual cysteine replacement at Y485, T489, S533, N573, or T586 did not alter VLP assembly as the chimeric VLPs appeared as spherical projections of 27 nm in diameter under electron microscopy. To evaluate the availability for cysteine acylation, we first examined the conjugation efficiency of HEV-VLP with maleimide-biotin which upon successful conjugation would induce VLP biotinylation through an irreversible reaction between the maleimide and thiol group of cysteine. Among all five mutant VLPs, the chimeric VLP carrying cysteine replaced at N573 (N573C-VLP) showed significantly higher efficiency in Mal-biotinylation than the other chimeric VLP, when assayed using labeled streptavidin. However, the dissembled N573C-VLP appeared no different in comparison to the others in the level of biotinylation (FIG. 2A). These data suggested that N573C-VLP provides a suitable cysteine arrangement to accommodate biotin conjugation and/or subsequent detection.

Chimeric N573C VLP do not React with HEV Antibody

Because the P-domain carries the antigenic structure of HEV, sequence mutation may alter the immunoreactivity of HEV antibodies against the obtained chimeric VLPs. In order to get an insight into the antigenicity of the chimeric VLPs, the antigenicity of the chimeric N573C VLP to the wild type HEV-VLP in the presence or absence of biotin conjugation was compared. An ELISA plate was coated with N573C VLP without conjugation, maleimide-biotin conjugated N573C VLP, or the wild type HEV-VLP and then incubated with two monoclonal antibodies, HEP230 or HEP40-4. In contrast to REP40-4, HEP230 exhibited strong binding for the wild type HEV-VLP, but failed to exhibit detectable binding to N573C VLP regardless of biotin conjugation (FIG. 29). The ELISA against the mixture of HEP230 and HEP40-4 showed similar trend (data not shown). This data suggested that residue N573 is important to HEP230 binding.

Residue N573 is Involved in FAB230 Binding

Proposed mutation sites lie in the surface variable loops of the P-domain. Residues Y485, T489, and T586 are exposed on the outmost surface of the P-domain plateau while residue S533 and N573 are located on the stem region of the P-domain (FIG. 1B). In order to understand the role of residue N573 in HEP230 binding, we determined the structure of HEV VLP complex with the Fab of HEP230 by cryo-electron microscopy (cryoEM) and image processing.

Figure 3:
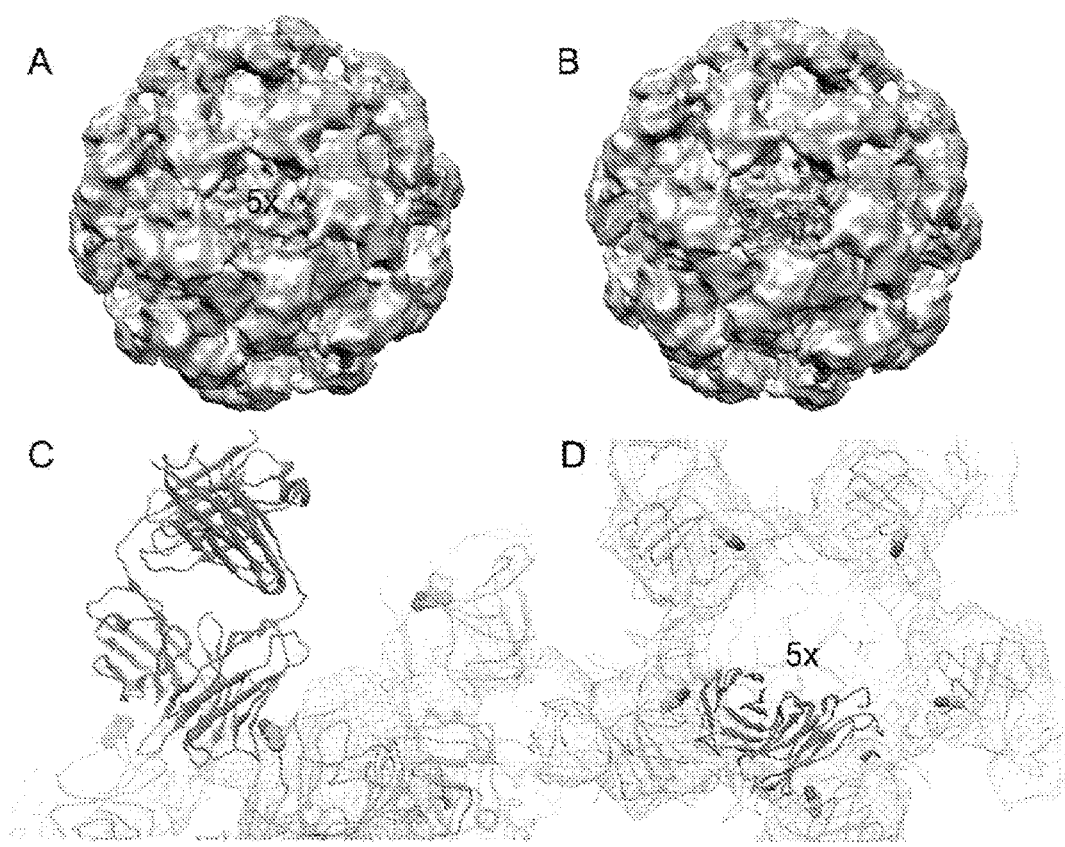

Chimeric VLP in complex with Fab of HEP230 (Fab230) appeared to resemble the morphology of HEV-VLP on cryo-electron micrographs. These complexes showed a homogenous size-distribution. The three dimensional reconstruction was calculated by superimposing icosahedral symmetry although the sixty antibody-binding sites on each VLP that were not fully occupied by Fab230. It revealed that HEV-VLP contains 30 protruding spikes, each of which extends outward along icosahedral two-fold axis (FIG. 3A). In contrast with the native HEV-VLP, these spikes appeared to connect with each other around the icosahedral fivefold axis. The connection density between the spikes was much weaker than the capsid and was not big enough to accommodate the Fab molecule. However, the size of the connection density appeared to be in good agreement with the contacting surface of the Fab molecule (FIG. 3B), indicating that the Fab230 may contact VLP at this position.

We subsequently validated this finding by releasing the five-fold and three-fold symmetries from three-dimensional reconstruction, i.e., using 2-2-2 symmetry instead of 5-3-2 symmetry during image processing. After five iterations of refinement, a single, slender density was observed extending from the same site of the P-domain inwardly towards the 5-fold axis (data not shown). This helped to confirm that Fab230 binds to this region. Model docking with the crystal structure of an Fab fragment (PDB code 3RKD) of HEV antibody 8C11 revealed that the extra density did cover the three contact loops in the Fab (FIG. 3C). Docking the crystal structure of HEV ORF2 (PDB code 1ZZQ) into the density map revealed that residue N573 is in the binding footprint of Fab230 (FIG. 3C, D), and could be in direct contact with the residues from Fab230.

LXY30 Conjugated to N573C VLP Shows Cancer Cell Targeting

Figure 4:
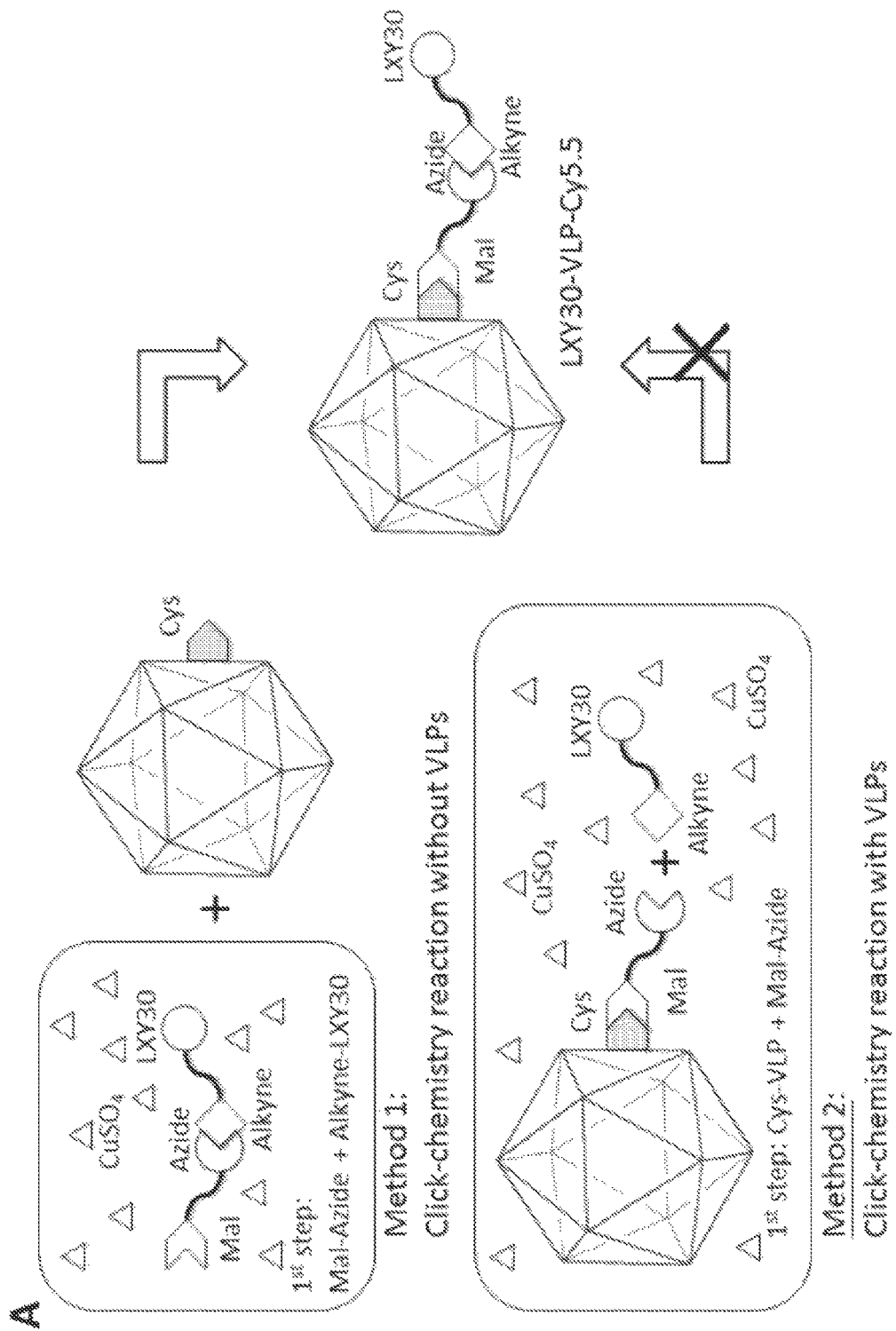
Figure 4:
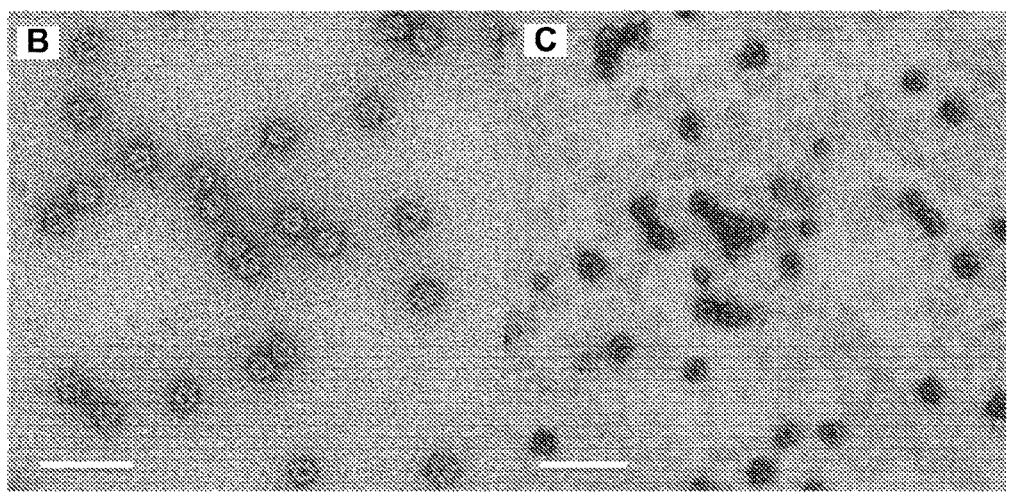

To assess the targeting and diagnostic capability of N573-VLP, a breast cancer cell targeting ligand, LXY30, was chemically added to the surface N573C-VLPs through a cysteine-anchored melamine-alkyne. The LXY30-decorated N573C-VLPs (LXY30-VLPs) remained intact after the chemical conjugation (FIG. 4), Flow cytometry revealed a significantly higher attachment (>5 fold) for LXY30-VLPs to MDA-MB-231 breast cancer cells, compared to that for the wild type VLPs (FIG. 5A), indicating that LXY30-VLP specifically targets breast cancer cells.

Figure 5:
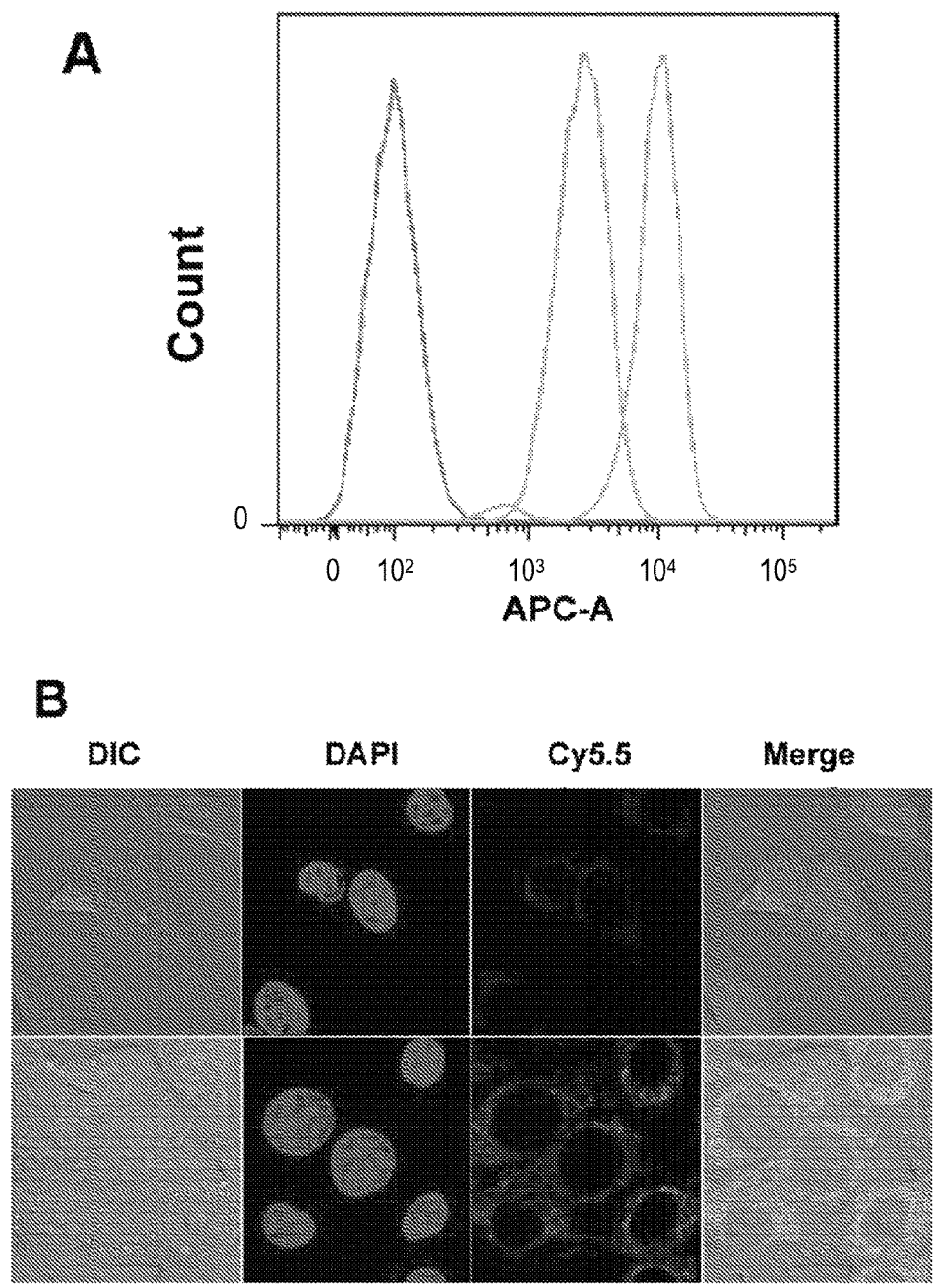

To determine if LXY30-VLPs enter the MDA-MB-231 cells, we examined the distribution of HEV ORF2 after incubation of LXY30-VLPs and MDA-MB-231 cells by the confocal microscopy. For this imaging, the LXY30-VLPs were labeled with the near infrared dye, Cy5.5, and incubated with MDA-MB-231 cells at 37° C. for 1 hour. As shown in FIG. 5B, most Cy5.5-labeled VLP distributed around the perinuclear region of MDA-MB-231 cells, which meant the VLP was internalized into the cytoplasm. Wild type VLPs had minimal cellular uptake, whereas LXY30-VLPs exhibited significantly higher uptake in MDA-MB-231 cells (FIG. 5B). These results demonstrated that the chemical conjugation with target ligand is capable of eliciting the specific uptake of HEV-VLP into breast cancer cells. LXY30 and scrambled LXY30 (S-LXY30) was also tested for uptake by the glioma cell line U-87MG, suggesting its use as a conjugate for HEV-VLP for targeting to glioma cells (FIG. 6).

In Vivo Targeting of LXY30 Conjugated to N573C VLPs to Breast Tumor Cells

Noninvasive in vivo imaging has been shown to be a powerful tool to visually monitor the delivery of therapeutic reagents. In vivo NIR optical imaging was used to investigate the distribution of the VLPs in nude mice bearing MDA-MB-231 breast cancer xenografts as a criterion to evaluate the specificity of tumor targeting. Both Cy5.5 labeled LXY30-VLPs and the Cy5.5 labeled wild type VLPs were intravenously injected via tail vein in nude mice bearing MDA-MB-231 xenografts, respectively. The mice were scanned with the fluorescence imager at various intervals for up to 72 hours, Both Cy5.5-labeled wild type VLPs and LXY30-VLPs distributed throughout the body of the mice immediately after the intravenous injection, and gradually accumulated into the MDA-MB-231 tumor via the enhanced permeability and retention (EPR) effect. However, the uptake rate of LXY30-VLPs in the tumor site was faster than that of wild type VLPs. The fluorescence intensity of Cy5.5-labeled LXY30-VLPs in MDAMB-231 tumor was also significantly higher than that of Cy5.5-labeled wild type VLPs at 1 and 6 hours post-injection (FIG. 7).

HEV, as an enteric transmitted virus, preferentially enters hepatocytes in liver. It is not surprising that Cy5.5 labeled VLPs accumulated within one hour at the abdominal organs including liver. Ex vivo imaging of excised organs were performed at 72 hours post injection. The remaining signal of Cy5.5 was found predominantly at the liver and kidney, however, the signal appeared weak in excised tumor (data not shown). The high uptake in liver and kidney could be explained in part as leaking of the breakdown VLPs from circulating vessels, Overall, these results indicate that Cy5.5/LXY30 linked HEV-VLPs is able to target MDA-MB-231 xenografts in vivo.

Discussion

There have been several attempts to use VLPs as a drug delivery system for diseases that require the delivery of cytotoxic drugs or specific genetic modifications, cell tagging, or drugs that require encapsulation. VLPs provide an opportunity for tissue/cell specific approaches while minimizing the overall damage to healthy cells. Compared to other nano-delivery systems that have a limited half-life due to early degradation; HEV-VLP, like the Hepatitis E virus can maintain its structure through the low pH and proteolytic mucosa/gastro environment and does not require cold-temperature for storage. This implies that HEV-VLPs could have a higher propensity for efficient delivery and reduced accumulation due to particle degradation,[20] both are critical factors for therapeutic nano carriers. The baculovirus expression vector-based production of HEV ORF2 in commercially-available insect High Five cells generates HEV-Cys-VLP capsid protein that is easily purified at high yield and low cost.[21] In contrast many other nano-delivery systems are compromised due to variable expression levels and inefficiency in production.

Cysteine replacement on the surface of the HEV-VLP P-domain was engineered so that accessibility to the ligands to the target cells was retained. Among all of the chimeric VLPs that were generated, N573C VLP construct appeared to show the strongest streptavidin binding on the basis of western blot analysis (FIG. 2A), although the cysteine thiol group is embedded within the surface depression at icosahedral fivefold axis. Structural analysis revealed that the distance between N573C and its five-fold related neighboring N573C is 45 Å, a distance that is in a good agreement with the length of a streptavidin monomer. In fact, streptavidin is a homotetramer in solution. The streptavidin homotetramer can intercalate into the surface depression and form multivalent interaction with N573C anchored biotin molecules, which largely reduces the rate of dissociation. As a result, the avidity of streptavidin to N573C VLP is the highest although the affinity of streptavidin to a single biotin appeared to be the same as it lowed by its binding to the disassembled VLPs. In contrast, the quaternary arrangement of cysteine residues in the other chimeric VLPs does not support multivalent binding of streptavidin.

The N573 residue is located within the binding footprint of Fab (FIG. 3), so that mutation of N573 blocks the interaction of PORF2 and HEP230. However, the volume of a fivefold depression is not sufficient to simultaneously accommodate five Fab molecules, so that the structure of Fab-bound VLP can only capture the contacting region of the Fab molecule after icosahedral-average. The density is about 20% occupancy to that of the capsid, suggesting that only one Fab molecule resided at each five-fold axis. This is consistent with the non-icosahedral symmetry averaged density map. This binding site is different to our previously reported binding site for antibody HEP224, whose binding depends critically on residue Y485 of HEV ORF2.[4] The reconstruction of HEP224 bound VLP revealed density of 60 Fabs at the shoulder of the P-domain with Fab extending away from VLP center.[4] This suggests of two distinctive antigenic domains on the surface of HEV-VLP that are not overlapped with each other; in agreement with the ELISA[13] and mutagenesis[19] results that were previously reported for HEV.

In conclusion, the HEV-573C VLPs were chosen as a platform of modularized theranostic capsule because of its possibility of weakening the immunoresistance against the pre-existing HEV antibodies as well as the possibility of multivalent binding with the ligand. In our experiment, we utilized two different conjugation methods: thiol-selective conjugation between maleimide and cysteine, and amine-selective conjugation between amine group and NHS-ester. We chose thiol-selective conjugation for coupling a cancer cell targeting ligand to VLP, because of the spatial specificity provided by cysteine replacement. To avoid competition, the conjugation of dye was performed by amine-selective conjugation that gave rise to sufficient NIR signal for us to detect VLP distribution in MDA-MB-231 breast cancer cells in vitro and in vivo (in mice). Therefore, the HEV-Cys LVPs can be used as a platform for dual-functional, tagging with cancer adhesion-ligand and a detection marker, a robust candidate for cancer diagnosis.

Besides conjugating the cancer-cell targeting ligand on the surface, the utilization of a modularized theranostic capsule can be expanded by using the interior space of HEV-Cys-VLPs as well. The HEV-Cys-VLP is capable of encapsulation of a variety of bioactive substances. For example, HEV-Cys-VLPs can encapsulate magnetic nanoparticles such as ferrite, for both diagnosis under MRI and thermotherapy. In such cases, the magnetic nanoparticles can be selectively stimulated using ultrasound or radio frequency electromagnetic radiation to heat the ferrite particles encapsulated in the tumor targeted theroanostic capsule.[22] Negatively charged micro-RNA/siRNA could be also encapsulated into the interior of HEV-Cys-VLPs.[17] By binding the cancer cell targeting ligand on its surface, HEV-Cys-VLP could have potential applications in cancer cell targeting gene therapy; consequently, this would improve current treatments used in cancer patients.

Materials and Methods

Site-Directed Mutagenesis of the P Domain of HEV ORF2

Figure 9:
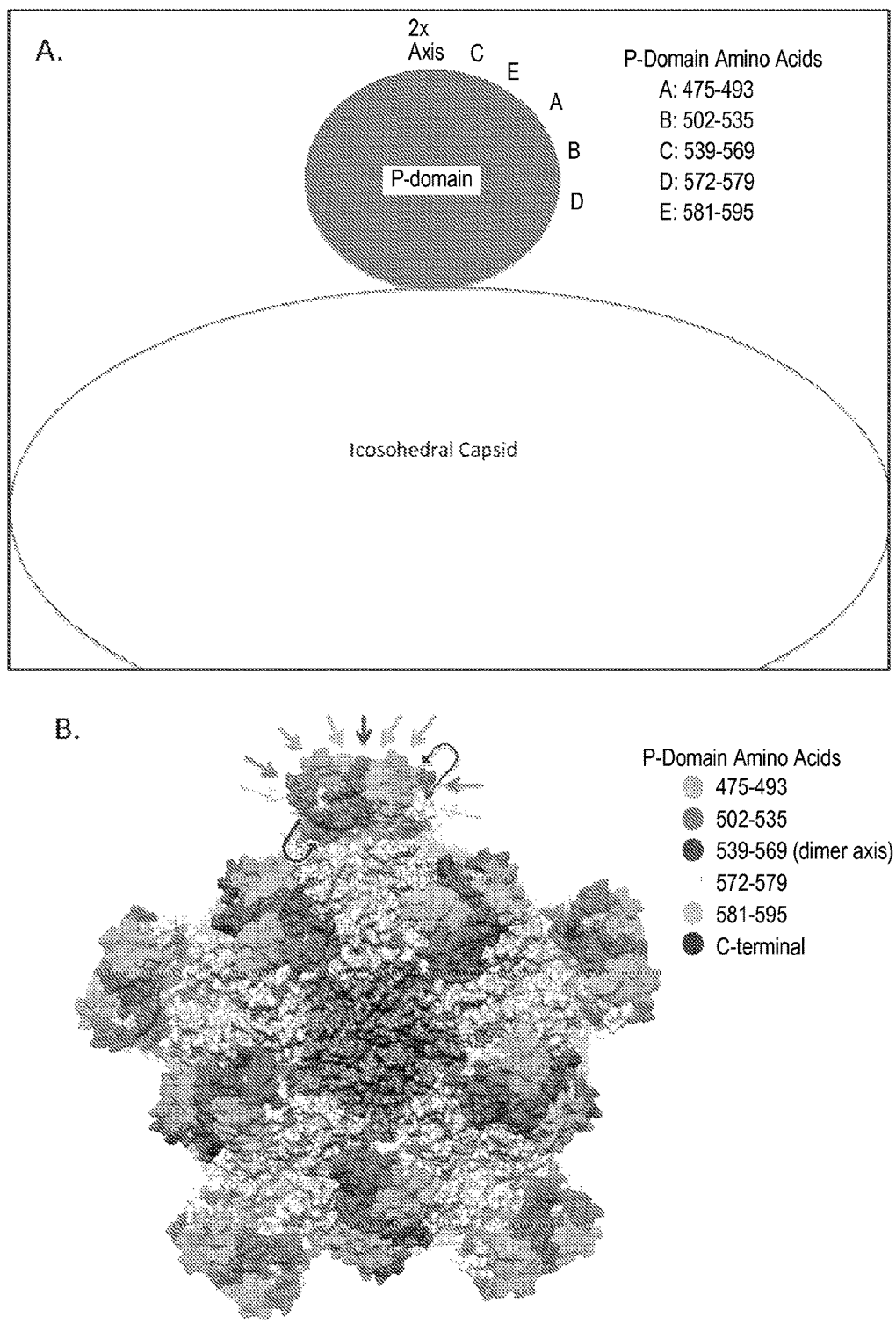

Five amino acid residues (Y485, T489, S533, N573, and T1586) of the P domain of HEV ORF2 (FIG. 9) were individually mutated to a cysteine residue by site-directed mutagenesis using a QuickChange site directed mutagenesis kit (Stratagene) following the manufacturer's protocols with the primers depicted in FIG. 8. The baculovirus transfer vector carrying the HEV ORF2 gene (pFastBac1/dORF2-HEV)[8] was used as template for the site directed mutagenesis. These residues were chosen for mutagenesis on the basis of the dimer model and crucial binding site information of HEV.[23] The mutated pFastBac1/dORF2-HEV plasmids carrying the site mutations Y485, T489, S533, N573, and T586 were named pFastBac1/dORF2-HEV-Y485, -T489, -S522, -N573, and -T586, respectively. The authenticity of each mutation in these plasmids was confirmed by sequencing of both strands.

Production and Purification of HEV-Cys VLPs and In Vitro Disassembly

The mutated HEV ORF2 proteins were expressed in insect High Five cells (Invitrogen, Carlsbad, Calif., USA) using baculovirus-based expression vectors. The recombinant baculoviruses used to express the mutated HEV ORF2 proteins were generated using the Bac-to-Bac® Baculovirus Expression System (Invitrogen) on Sf9 cells (Invitrogen) and each of the pFastBac1/HEV ORF2 plasmids described above according to the protocols supplied by the manufacturer. The Sf9 and High Five cells were maintained on ESF921 medium (Expression Systems, Davis, Calif. USA) and Excell 420 medium (SAFC Biosciences, Lenexa, Kans.) supplemented with 2.5% heat-inactivated FBS, respectively, following standard protocols.[24] The production and purification of HEV-Cys-VLPs from the various mutated POR2 constructs were conducted as described previously.[7] In order to express the mutated POR2 proteins and generate VLPs, the High Five cells were inoculated with each baculovirus construct at a multiplicity of infection of 5 and cultured for 6-7 days. The VLPs were collected and purified through multiple steps of CsCl equilibrium density gradient ultracentrifugation as described previously.[7] The purified VLPs were resuspended in 10 mM potassium-MES buffer, pH 6.2, and stored at 4° C. A Mini dialysis device (Millipore) was used in the disassembly experiments. The purified VLPs were disrupted by dialysis against buffer containing EDTA (10 mM) or/and DTT (20 mM).

Transmission Electron Microscopy

The purified VLPs were loaded onto a glow-discharged, carbon-coated EM grid and stained with 2% uranyl acetate and examined under a JOEL JEM-1230 transmission electron microscope at a magnification of 30,000×. The images were recorded on a CCD camera (TVIPS Gauting, Germany).

Conjugation of Biotin to HEV-Cys VLPs

To chemically conjugate maleimide linked biotin to HEV-Cys VLPs, maleimide linked biotin (20 µM-200 µM) was used to react with HEV-Cys VLPs (4 µM-40 µM) in 0.01M PBS, pH 7.2 at 4° C. overnight. The unbound maleimide-biotin was then removed using a 7,000 MWCO desalting column, (Zeba™ Spin Desalting Columns, Thermo Scientific).

Western Blotting

A total of 2 µg of the biotin conjugated HEV-Cys ORF2 were loaded per lane on a 10% SDS-PAGE running under reducing condition. The proteins were then transferred to a polyvinylidene fluoride (PVDF) membrane (Millipore Co.) for Western immunoblotting. The PVDF membrane was first blocked with 5% skim milk and then incubated for 1 hour at room temperature with HRP conjugated streptavidin at a ratio of 1:10,000. The biotin-streptavidin reaction was then detected by an enhanced chemiluminescence method using an ECL kit (Amersham Biosciences, Piscataway, N.J.).

Enzyme-Linked Immunosorbent Assay (ELISA)

Both recombinant HEV-WT-VLP particles including HEV-WT and HEV-Cys mutants were prepared in 10 mM potassium-MES, pH 6.2 coating buffer. The proteins were diluted to the final concentrations of 1-100 ng/ml and coated overnight at 4° C. onto a clear bottom 96-well plate (Nunc, Pleasant Prairie, Wis.). Control wells were incubated with 0.01 M PBS, pH 7.12. The coated VLPs were incubated with ~50 µl of the HEV antibodies for two hours at 37° C. after blocking with 0.5% Tween-20 Tris buffer containing 20 mM Tris, pH 7.4, and 150 mM NaCl. The associated HEV antibodies were detected using alkaline phosphatase-labeled anti-mouse FAb. The enzymatic reaction was developed using pnitrophenylphosphate (pNPP) solution (Sigma Co). The yellow color product of nitrophenyl was measured at 405 nm using a microplate reader and the average absorbance value of each VLP was calculated.

Preparation of LXY30-VLP-Cy5.5

Maleimide-conjugated LXY30 was prepared by mixing 650 µM maleimide-azide and 650 µM alkyne-LXY30 in the presence of 200 µM CuSO4 and 1 mM ascorbic acid at 4° C. overnight. Then maleimide-conjugated LXY30 was added at molar ratio of 3:1 (ligand vs. binding site) to react with the Cys residues on HEV-Cys mutants though a thiol reaction at 4° C. overnight. The unconjugated molecules were removed by a 7,000 MWCO desalting columns, (Zeba™ Spin Desalting Columns, Thermo Scientific).

To chemically conjugate Cy5.5 NHS ester (Limiprobe) to HEV-Cys VLPs, Cy5.5 NHS ester (200 nm) was used to react with HEV-Cys mutants (20 µM) at molar ratio of 300:1 (dye vs VLP) in buffer containing 0.1 M PHs, pH 7.2 at room temp for 2 hrs, following by incubation at 4° C. overnight. The free Cy5.5 NHS ester was then removed by a 7,000 MWCO desalting column, (Zeba™ Spin Desalting Columns, Thermo Scientific).

Flow Cytometry

MDA-MB-231 breast cancer cells were incubated with Cy5.5-labeled HEV-573C VLPs (VLP-Cy5.5) or Cy5.5/LXY30 conjugated HEV-573C VLPs (LXY3-VLP Cy5.5) for 1 hour at 37° C., respectively. Then the cells were washed with PBS 3 times and re-suspended in PBS for the flow cytometric analysis.[18] A total of 10,000 events were collected for each sample. Unstained cells were used as a control.

Confocal Microscopy

The sample preparation was performed according to previously established protocols.[25] Briefly, MDA-M B-231 breast cancer cells were seeded in the coverglass chamber slides (VWR LabShop, Batavia, Ill.). After reaching 80% confluence, the cells were incubated with Cy5.5-labeled HEV-573C VLPs (VLP-Cy5.5) and Cy5.5-labeled LXY30-conjugated HEV-573C VLPs (LXY3-VLP-Cy5.5), respectively for 1 h at 37° C. The cell nuclei were stained with Hoechst 33342 (invitrogen) for 5 min. The cells were washed twice with PBS and replaced with fresh medium before observation under a Zeiss confocal fluorescence microscope.

In Vivo Optical Imaging

Female SPF BALB/c mice, 10-12 weeks age, were purchased from Charles River (Davis, Calif.)) and kept under pathogen-free conditions according to AAALAC guidelines and were allowed to acclimatize for at least 4 days prior to any experiments. MDA-MB-231 breast cancer cells were injected subcutaneously into nude mice to form subcutaneous nodules. All animal experiments were performed in compliance with institutional guidelines and according to protocol No. 06-12262 approved by the Animal Use and Care Administrative Advisory Committee at the University of California, Davis. MDA-MB-231 tumors bearing mice were intravenously injected through the tail vein with 4 nmol/L Cy5.5 fluorescent-labeled HEV-573C VLPs (VLP-Cy5.5) and LXY30 conjugated HEV-573C VLPs (LXY30-VLP-Cy5.5) respectively.

At different time points (1, 6, 24 and 48 hours post-injection), the mice were scanned with Kodak imaging system IS2000MM according to the procedure described previously.[26] Images were collected with an excitation bandpass filter at 625 nm and an emission at 700 nm, exposure time was 30 s per image. After in vivo imaging, animals were euthanized by $CO_2$ overdose at 72 h after injection. Tumors, organs, and muscle tissue were excised and imaged with the Kodak imaging station.

Preparation of VLP-Fab Complexes for Cryoelectron Microscopy

The VLP-Fab complexes were prepared by incubating VLPs and Fabs at a molar ratio of 1:180 at 4° C. overnight. To ensure optimal purity, maximal occupancy, and ultimately reduced background noise during structural determination, pure VLP-FAB complexes were obtained by passing the sample through a short Sephacryl-300 gel-filtration column. Optical density readings at a wavelength of 280 nm were used to select the fractions that contained VLP-Fab complexes. The purified VLP fraction was then characterized by SDS-PAGE under reducing condition to validate the binding of Fab.

Cryoelectron Microscopy

Procedures regarding cryo-EM and its sample preparation were essentially similar to as those previously described.[27] Briefly, a drop of HEV-VLP aliquot of optimal concentration was applied to a glow-discharged holey carbon-coated copper grid, blotted to remove excess liquid, and immediately plunged into liquid ethane. The frozen-hydrated specimen was then transferred onto a Gatan 626DH cryo holder and examined under a transmission electron microscope (TEM-2100F, JEOL) at liquid nitrogen temperature. Micrographs were acquired under minimal dose system on a TemCam-F415 CCD camera (TVIPS) at a pixel size of 2 Å at the specimen space. The applied defocus varied from 1,000 to 3,000 nm among the micrographs. Particle concentration, optimal ice thickness, and minimal specimen shift were the visual criteria for selecting micrographs.

Imaging Processing

Particles were then manually selected and initially centered via cross-correlating each one against the sum of the image circular average. Astigmatism and defocus values were evaluated by superimposing power spectra from all the particles within a single micrograph. The contrast transfer function was determined and phase correction was applied to the data used for structural determination. The initial model of the wild type HEV-VLP was obtained from previous study.[13] The Polar Fourier transformation (PFT) algorithm[28] was used to iteratively carry out origin and orientation refinements for each particle. Three-dimensional reconstructions were computed by combining a set of particles with orientations that spread evenly in an icosahedral asymmetric unit while superimposing the 5-3-2 icosahedral symmetry. The reliability of the reconstruction was assessed with classical Fourier Shall Correction and the final resolution was determined at 15 Å using 0.5 as cut off.

Fitting the Crystal Structure into Cryo-EM Density Maps

Manual fitting was carried out by translational and rotational movement of the HEV decanter composed of ten units of the HEV ORF2 protein (PDB ID 2ZZQ) into the cryo-EM density maps using program O.[29] The fitting was first manually refined by minimizing the crashes between symmetry related HEV ORF2 molecules and then evaluated based on the cross correlation coefficient (CC value) between the cryo-EM density and the density computed from the fitted HEV ORF2 coordinates. Fitting was halted when the CC value reached 80%. The Fab coordinates were obtained from the crystal structure of Fab8C11 bound HEV P-domain (PDB ID 3RKD) and was docked into the cryoEM map while maintaining the binding interface as the contacting surface to the VLP.

REFERENCES

1. Ludwig, C.; Wagner, R., Virus-like particles-universal molecular toolboxes. *Curr Opin Biotechnol* 2007, 18, 537-545.
2. Purcell, R. H., Hepatitis virus. In *Fields Virology*, 3rd Ed, ed.; Fields, B. N.; Knipe, D. M.; Howley, P. M., Eds. Lippincott—Raven Publishers: Philadelphia, 1996; pp 2831-2843.
3. Tam, A. W.; Smith, M. M.; Guerra, M. E.; Huang, C. C.; Bradley, D. W.; Fry, K. E.; Reyes, G. R., Hepatitis E virus (HEV): molecular cloning and sequencing of the full-length viral genome. *Virology* 1991, 185 (1), 120-31.
4. Xing, L.; Wang, J. C.; Li, T. C.; Yasutomi, Lara, J.; Khudyakov, Y.; Schofield, D.; Emerson, S. U.; Purcell, R. H.; Takeda, N.; Miyamura, T.; Cheng, R. H., Spatial configuration of hepatitis E virus antigenic domain. *J Virol* 2011, 85 (2), 1117-24.
5. Schofield, D. J.; Glamann, J.; Emerson, S. U.; Purcell, R. H., identification by phage display and characterization of two neutralizing chimpanzee monoclonal antibodies to the hepatitis E virus capsid protein. *J Virol* 2000, 74 (12), 5548-5555.
6. Yu, H.; Li, S.; Yang, C. Y.; Wei, M.; Song, C.; Zheng, Z.; Gu, Y.; Du, H.; Zhang, J.; Xia, N. S., Homology model and potential virus-capsid binding site of a putative HEV receptor Grp78. *J Mol Model* 2010, Epub ahead of print.
7. Li, T.-C.; Takeda, Miyamura, T.; Matsuura, Y.; Wang, J. C. Y.; Engvall, H.; Hammar, L.; Xing, L.; Cheng, R. H., Essential elements of the capsid protein for self-assembly into empty virus-like particles of hepatitis E virus, *J. Virol.* 2005, 79 (20), 12999-13006.
8. Li, T. C.; Yamakawa, Y.; Suzuki, K.; Tatsurni, M.; Razak, M. A.: Uchida, T.; Takeda, N.; Miyamura, T., Expression and self-assembly of empty virus-like particles of hepatitis E virus. *J Virol* 1997, 71 (10), 7207-7213.
9. Guu, T.; Liu, Z.; Ye, Q.; Mata, D.; Li, K.; Yin, C.; Zhang, J.; Tao, Y., Structure of the hepatitis E virus-like particle suggests mechanisms for virus assembly and receptor binding. *Proc Natl Acad Sci USA* 2009, 106, 12992-12997.
10. Xing, L.; Li, T. C.; Miyazaki, N.; Simon, M. N.; Wall, J. S.; Moore, M.; Wang, C. Y.; Takeda, N.; Wakita, T.; Miyamura, T.; Cheng, R. H., Structure of hepatitis E virion-sized particle reveals an RNA-dependent viral assembly pathway. *J Biol Chem* 2010, 285, 33175-33183.
11. Yamashita, T.; Mori, Y.; Miyazaki, N.; Cheng, H.; Yoshimura, M.; Unno, H.; Shima, R.; Moriishi, K.; Tsukihara, T.; Li, T. C.; Takeda, N.; Miyamura, T.; Matsuura, Y., Biological and immunological characterics of hepatitis E virus-like particles based on the crystal structure. *Proc Natl Acad Sci USA* 2009, 106, 12986-12991.
12. Xing, L.; Kato, K.; Li, T.; Takeda, N.; Miyamura, T.; Hammar, L.; Cheng, R. H., Recombinant hepatitis E capsid protein self-assembles into a dual-domain T=1 particle presenting native virus epitopes. *Virology* 1999, 265 (1), 35-45.
13. Jariyapong, P.; Xing, L.; van Houten, N. E.; Li, T. C.; Weerachatyanukul, W.; Hsieh, B.; Moscoso, C. G.; Chen, C. C.; Niikura, M.; Cheng, R. H., Chimeric hepatitis E virus-like particle as a carrier for oral-delivery. *Vaccine* 2013, 31 (2), 417-24.
14. Niikura, M.; Takamura, S.; Kim, G.; Kawai, S.; Saijo, M.; Morikawa, S.; Kurane, I.; Li, T. C.; Takeda, N.; Yasutomi, Y., Chimeric recombinant hepatitis E virus-like particles as an oral vaccine vehicle presenting foreign epitopes. *Virology* 2002, 293 (2), 273-280.

15. Zafrullah, M.; Khursheed, Z.; Yadav, S.; Sahgal, D.; Jameel, S.; Ahmad, Acidic pH enhances structure and structural stability of the capsid protein of hepatitis E virus. *Biochem Biophys Res Commun* 2004, 313 (1), 67-73.
16. Li, T.-C.; Suzaki, Y.; Ami, Y.; Dhole, T. N.; Miyamura, T.; Takeda, N., Protection of cynomolgus monkeys against HEV infection by oral administration of recombinant hepatitis E virus-like particles. *Vaccine* 2004, 22, 370-377.
17. Takamura, S.; Niikura, M.; Li, T. C.; Takeda, N.; Kusagawa, S.; Takebe, Y.; Miyamura, T.; Yasutomi, Y., DNA vaccine-encapsulated virus-like particles derived from an orally transmissible virus stimulate mucosal and systemic immune responses by oral administration. *Gene Ther* 2004, 11 (7), 628-635.
18. Yao, N.; Xiao, W.; Wang, X.; Marik, J.; Park, S. H.; Takada, Y.; Lam, K. S., Discovery of targeting ligands for breast cancer cells using the one-head one-compound combinatorial method. *J Med Chem* 2009, 52 (1), 126-33.
19. Calaway, F. A.; Stockley, P. G., MS2 viruslike particles; a robust, semisynthetic targeted drug delivery platform. *Molecular pharmaceutics* 2013, 10 (1), 59-68.
20. Ma, Y.; Nolte, R. J.; Cornelissen, J. J., Virus-based nanocarriers for drug delivery. *Advanced drug delivery reviews* 2012, 64 (9), 811-25.
21. Kawano, M.; Xing, L.; Lam, K. S.; Handa, H.; Miyamura, T.; Barnett, S.; Sreivastava, I. K.; Cheng, R. H. Design platforms of nanocapsules for human therapeutics or vaccine In *Development of Vaccines* Singh; Srivastava, I. K., Eds. Wiley Pub 2011; pp 125-140.
22. Roemer, R. B., Engineering aspects of hyperthermia therapy. *Annu Rev Biomed Eng* 1999, 1, 347-76.
23. Nilsson, J.; Miyazaki, N.; Xing, L.; Wu, B.; Hammar, L.; Li, T. C.; Takeda, N.; Miyamura, T.; Cheng, R. H., Structure and Assembly of a T=1 Virus-Like Particle in BK Polyomavirus. *J. Virol.* 2005, 79 (9), 5337-5345.
24. Merrington, C. L.; King, L. A.; R. D., P., Baculovirus expression systems. In *Protein Expression: A practical Approach*, Higgins, S. J.; Hames, B. D., Eds. Oxford University Press: 1999; pp 101-127.
25. Xiao, K.; Li, Y.; Lee, J. S.; Gonik, A. M.; Dong, T.; Fung, G.; Sanchez, E.; Xing, L.; Cheng, H. R.; Luo, J.; Lam, K. S., "OA02" peptide facilitates the precise targeting of paclitaxel-loaded micellar nanoparticles to ovarian cancer in vivo. *Cancer Res* 2012, 72 (8), 2100-10.
26. Luo, J.; Xiao, K.; Li, Y.; Lee, J. S.; Shi, L.; Tan, Y.; Xing, L.; Cheng, H.; Liu, G.; Lam, K. S., Well defined, size-tunable, multifunctional micelles for efficient paclitaxel delivery for cancer treatment, *Bioconjugate Chem.* 2010, 21, 1216-1224.
27. Kawano, M. A.; Xing, L.; Tsukamoto, H.; Inoue, T.; Handa, H.; Cheng, R. H., Calcium bridge triggers capsid disassembly in the cell entry process of simian virus 40. *J. Biol Chem* 2009, 284 (50), 34703-12.
28. Baker, T.; Cheng, H., A model based approach for determining orientations of biological macromolecules imaged by cryo-electron microscopy. *J. Struct. Biol.* 1996, 116, 120-130.
29. Jones, T. A.; Zou, J. Y.; Cowan, S. W.; Kjeldgaard, M., Improved method for building protein model in electron density maps and the location of errors in these models. *Acta crystallogr. Sect. A* 1991, 47, 110-119.

Example 2: Functionalized Nanocarriers

Introduction

Figure 10:
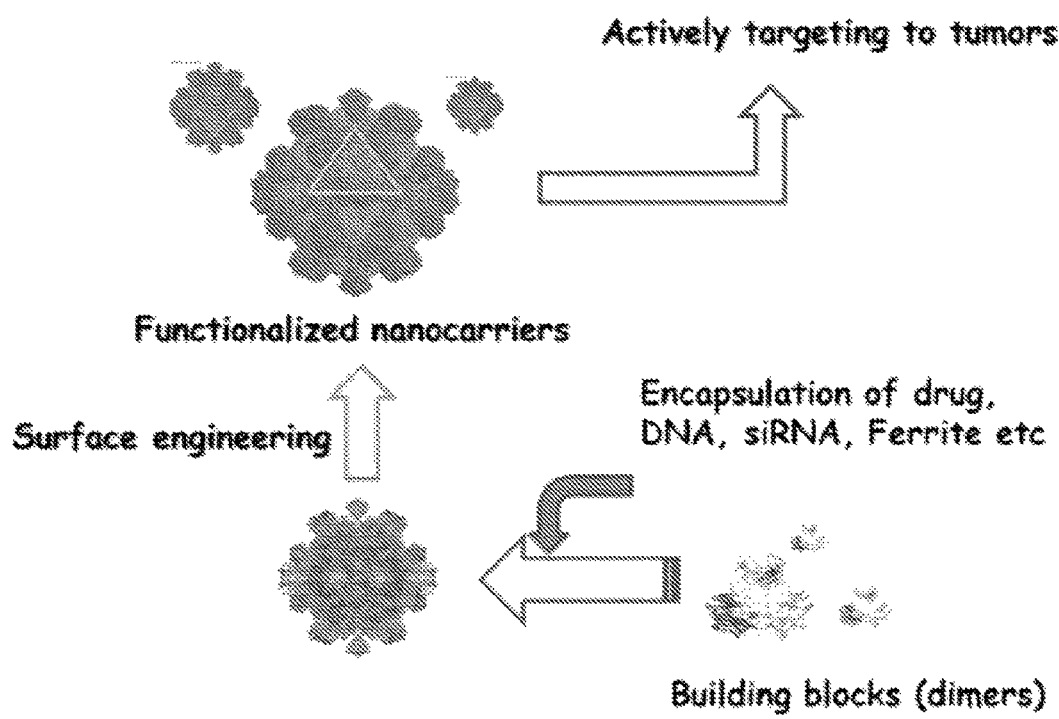

FIG. 10 depicts various routes for modifying the surface of HEV ORF2 VLP nanocarriers and encapsulation of detectable labels, drugs, or nucleic acid payloads. An HEV ORF2 VLP-based nanocarrier can self-assemble in vitro and encapsulate anticancer therapeutics or image reagents. With genetic engineering, cancer targeting ligands can be conveniently ligated to the surface of the carrier for cancer-specific targeted delivery. Overall, the chimeric VLP exhibits excellent biocompatibility, high absorption of near-infrared light, and structure-dependent fluorescence quenching/emission. This nanomedicine platform allows integration of multiple imaging and therapeutic modalities for superior cancer detection and therapy.

Intratumoral delivery is a challenge task for modern medical research and is a process that comprises lots of negotiations between nanocarriers with cells, extracellular matrix, and the vasculature inside the tumor. Described herein is an HEV-VLP based nanocarrier for targeted tumor delivery guided by imaging the in situ distribution of VLP at the whole animal level, to the tumor interior, and ultimately down to subcellular organelles. Engineered HEV-VLPs for tumor targeting are provided by adding adhesion tag(s) to the surface of the P-domain. A genetically inserted a fluorescence marker can also be inserted into the VLP so that it can be used as endogenous reporter. Use of these nanoparticles demonstrate the power of correlative microscopic studies on the role it plays in the development of nanocarriers.

The use of nanoparticles in passive and targeted drug delivery has been dramatically increased over the past decades. Nanocarriers composed of synthetic polymers, Liposomes, and dendrimers, have been well-investigated, however, there are only two FDA-approved antibody-conjugates and four FDA-approved nanoparticle-based drug delivery carriers. Virus like particle (VLP) is natural provided nanocarriers that possess several attractive features. They can be self-assembled into monodisperse, nanosized particles, with defined periodicity that enables dense, repetitive display of tumor targeting agents. In addition, the VLP possesses multiple unique features that make it more attractive as potential nanocarrier.

Figure 11:
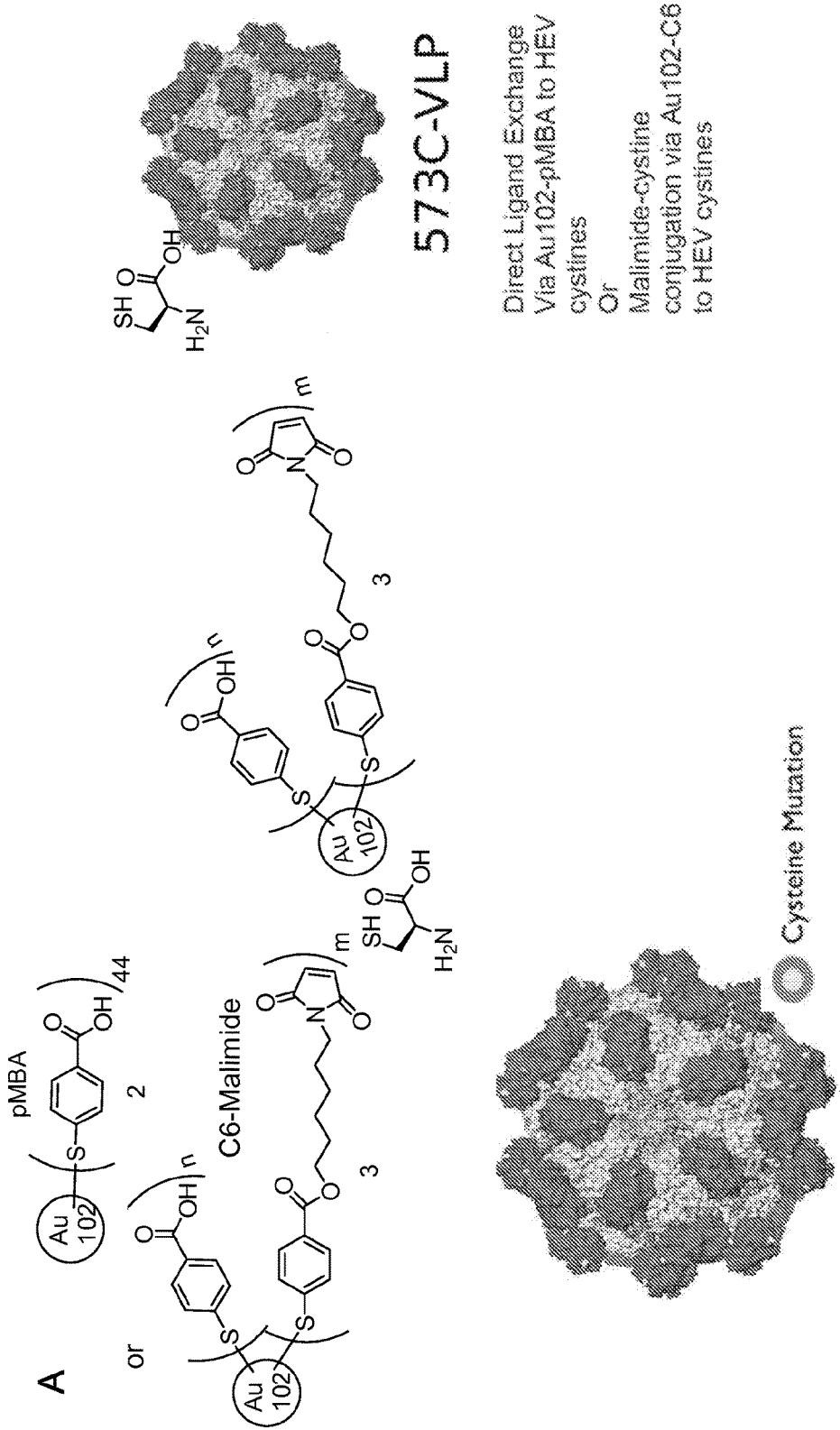
Figure 11:
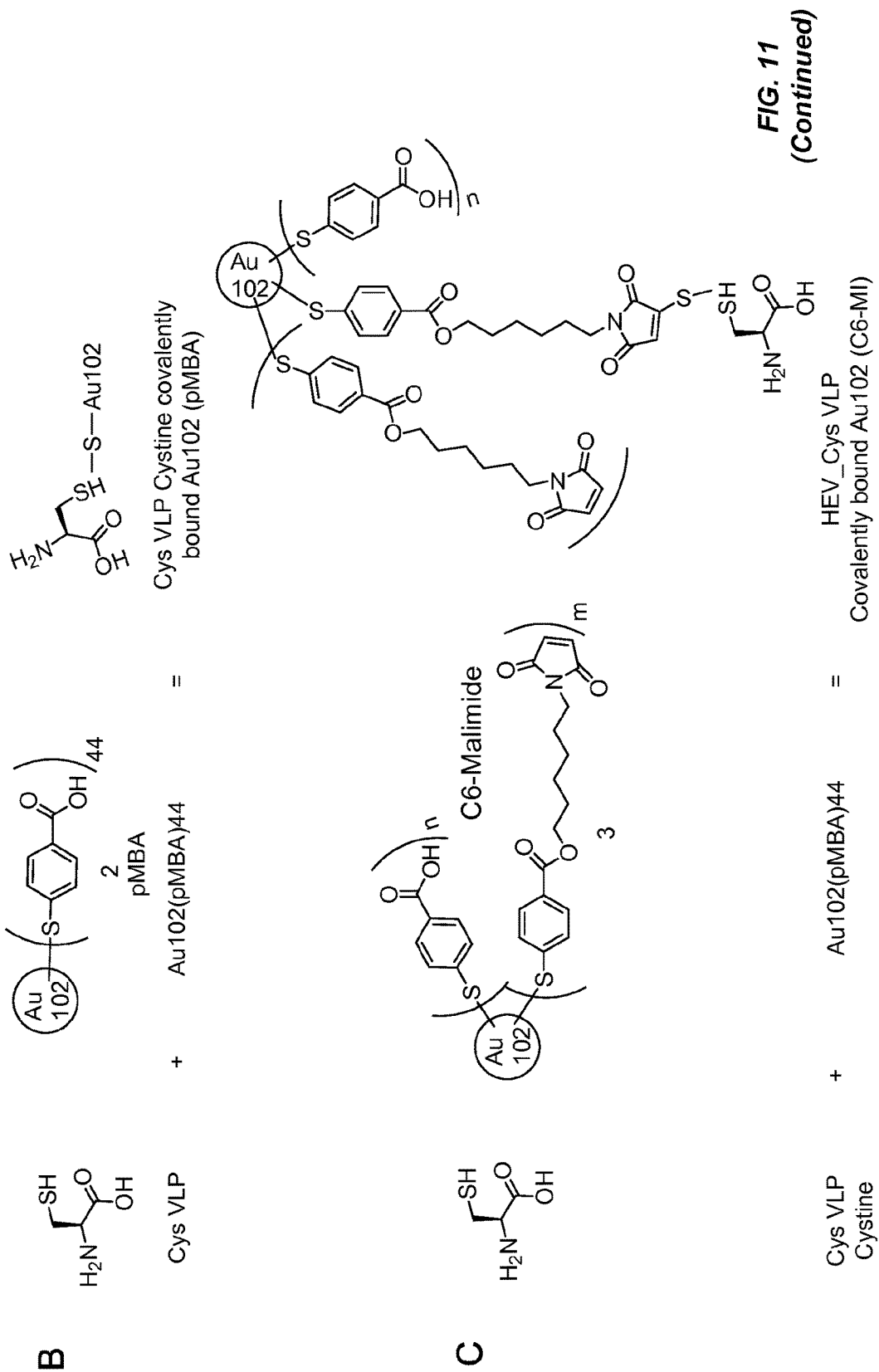
Figure 11:
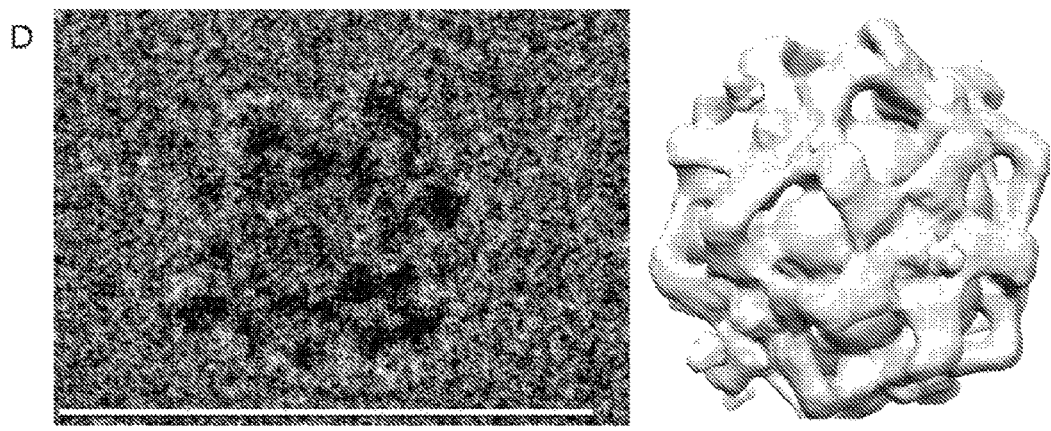

HEV VLP nanoparticles can be characterized with electron microscopy in the presence or absence of contrast enhancing reagents. Microscopic characterization of nanoparticles can be routinely performed to examine the physical properties of the nanocarriers using methods described herein, such as imaging frozen hydrated multifunctional particles, e.g., using contrast enhanced gold atom clusters (FIG. 11A). Methods and compositions for conjugating gold clusters to cysteine thiolates include direct ligand exchange and/or maleimide cysteine conjugation (see, e.g., Ackerson et al., Bioconjug. Chem., 21, 214-218 (2010); Ackerson et al., Methods Enzymol., 481:195-230 (2010); and Marjormäki et al., PNAS, 111(4):1277-81 (2014)). The direct visualization by electron microscopy precisely reveals the size, shape, and domain arrangement of the nanoparticles, as well as the protein/drug absorption on nanoparticles, factors that can influence the overall bioactivity of the nanoparticles and the efficacy of targeted tumor delivery. The nanoparticles can be imaged with either by cryo-electron microscopy on unstained frozen hydrated specimen or by traditional electron microscopy on negatively stained specimen. The cryoEM is well-suited to imagine the biological macromolecular complexes (FIG. 11A-D).

Moreover, correlative microscopic techniques can be based on these newly described conjugates to achieve the utilization of multiple imaging modalities in the examination of the same tumor specimen in order to deliver information above and beyond the capability of either modality alone. For instance, light and electron microscopy can be used to image from the organismal level, to the organ level, to cells, and even subcellular details. In combination with Near-Infrared (NIR) whole animal imaging and/or micro-CT, correlative light and electron microscopy (CLEM) allows in vitro and in vivo imaging of VLP intratumoral distribution. With, e.g., high pressure freezing and freeze substitution, tumor diagnosis can be preserved to maintain the sufficient antigenicity of HEV-VLP for immunofluorescence labeling.

Region identification is one of the critical issues for tumor diagnosis, where both light and electron microscopies indeed image the same object. For instance, with HEV VLPs described herein, the coordinates of 1) photoconversion of DAB (3,3'-diaminobenzidine tetrahydrochlroride); 2) dual functional probe, FluoroNanogold; and 3) EM finder grids can be informative in multiple modalities of tumor identification. The first method uses free oxygen radicals that formed upon illumination of fluorochromes to induce oxidation of DAB in situ. While visualizing specimen under fluorescence microscope in the presence of DAB solution, the oxidized DAB forms networks that will be stained with osmium tetroxide as fine granular, dense precipitates at the sites of the former fluorescent signals. FluoroNanogold conjugated antibody is a commercially available reagent that provides both light and electron microscope contrast by conjugation of 1.4 nm gold clusters either with green or with red fluorophore. Unlike colloidal gold of other sizes, the 1.4 nm nanogold cluster does not quench fluorescence.

HEV VLPs described herein allow detection and visualization by 3D electron tomography to monitoring drug delivery. Electron tomography provides 3D spatial information to describe the biodistribution of drug delivery vehicles inside the tumor. In a three-dimensional entity, the microenvironment of tumor can be much more complex than what found in vitro with cultured monolayer cells. Electron tomography can be used as a complement to CLEM in analyzing the intratumoral accumulation of drug-loaded VLP, so as to elucidate the mechanism for VLP extravasation and passing through the cell layers inside a tumor.

Furthermore, besides the gold clusters, HEV VLPs can be equipped and encapsulated with additional imaging agents, e.g., water-soluble CdSe/ZnS quantum dots or Ferrite, in a disassembly-and-reassembly process (FIG. 12). Quantum dots can provide an dual-functional probe to track VLP tumor uptake with correlative light and electron microscopy. The efficiency of packaging can be optimized to have efficient encapsulation, e.g., by coating the quantum dots with an HEV encapsidation signal through LC-SPDP-mediated crosslinking. An RNA element occupying codons 35-59 of HEV open reading frame 1 is a powerful encapsidation signal, allowing specific interaction in vitro with HEV capsid protein, including truncated and/or cysteine modified versions of HEV ORF2 VLP described herein. To use VLP as drug carrier, chemical linkers (e.g., LC-SPDP aptamer, telodendrimers) that tag the drug (e.g., chemotherapeutic) with an HEV encapsidation signal like the foregoing RNA element can be used prior to the capsid self-assembly.

```
SEQ ID NO: 1 > HEV genotype 1 (NP_056788.1)
   1 mrprpillll lmflpmlpap ppgqpsgrrr grrsggsggg fwgdradsqp faipyihptn 61 pfapdvtaaa gagprvrqpa rplgsawrdq aqrpaaasrr rpttagaapl tavapahdtp 121 pvpdvdsrga iirrqynlst spltssvatg tnlvlyaapl spllplqdgt nthimateas 181 nyaqyrvvra tiryrplvpn avggyaisis fwpqttttpt svdmnsitst dvrilvqpgi 241 asehvipser lhyrnqgwrs vetsgvaeee atsglvmlci hgslvnsytn tpytgalgll 301 dfalelefrn ltpgntntrv srysstarhr lrrgadgtae ltttaatrfm kdlyftstng 361 vgeigrgial tlfnladtll gglpteliss aggqlfysrp vvsangeptv klytsvenaq 421 qdkgiaiphd idlgesrvvi qdydnqheqd rptpspapsr pfsvlrandv lwlsltaaey 481 dqstygsstg pvyvsdsvtl vnvatgaqav arsldwtkvt ldgrplsttq qysktffvlp 541 lrgklsfwea gttkagypyn ynttasdqll venaaghrva istyttslga gpvsisavav 601 laphsalall edtmdypara htfddfcpec rplglqgcaf qstvaelqrl kmkvgktrel SEQ ID NO: 2 > HEV genotype 3 (BAH10873.1)
   1 mrpravlllf fvllpmlpap pagqpsgrrr grraggaggg fwgdrvdsqp falpyihptn 61 pfaadvvsqs gagarprqpp rplgsawrdq sqrpsaaprr rsapagaapl taispapdta 121 pvpdvdsrga ilrrqynlst spltssvapg tnlvlyaapl npllplqdgt nthimeteas 181 nyaqyrvvra tiryrplvpn avggyaisis fwpqttttpt avdmnsitst dvrilvqpgi 241 aselvipser lhyrnqgwrs vettgvaeee atsglvmlci hgspvnsytn tpytgalgll 301 dfalelefrn ltpgntntrv srytstarhr lrrgadgtae ltttaatrfm kdlhftgtng 361 vgevgrgial tlfnladtll gglpteliss aggqlfysrp vvsangeptv klytsvenaq 421 qdkgitiphd idlgsdrvvi qdydnqheqd rptpspapsr pfsvlrandv lwlsltaaey 481 dqttygsstn pmyvsdtvtf vnvatgaqav arsldwskvt ldgrplttiq qysktfyvlp
```

```
541 lrgklsfwea gttkagypyn ynttasdqil ienaaghrva istyttslga gptsisavgv 601 laphsalavl edttdypara htfddfcpec rtlglqgcaf qstiaelqrl kmkvgktres SEQ ID NO: 3 > HEV genotype 4 (ABE27148.1)
  1 mrpravlllf fvllpmlpap pagqpsgrrr grrsggtggg fwgdrvdsqp falpyihptn 61 pfasdiptat gagarprqpa rplgsawrdq sqrpaaparr rsapagaspl tavapapdta 121 pvpdvdsrga ilrrqynlst spltstiatg tnlvlyaapl spllplqdgt nthiiateas 181 nyaqvrvvra tiryrplvpn avggyaisis fwpqttttpt svdmnsitst dvrilvqpgi 241 aselvipser lhyrnqgwrs vetsgvaeee atsglvmlci hgspvnsytn tpytgalgll 301 dfalelefrn ltpgntntrv srysssarhk lcrgpdgtae ltttaatrfm kdlhftgtng 361 vgevgrgial tllnladtll gglpteliss aggqlfysrp vvsangeptv klytsvenaq 421 qdkgiaiphd idlgesrvvi qdydnqheqd rptpspapsr pfsvlrandv lwlsltaaey 481 dqttygsstn pmyvsdtvtf vnvatgtqgv srsldwskvt ldgrplttiq qysktffvlp 541 lrgklsfwea gttkagypyn ynttasdqil ienapghrvc istyttnlgs apvsisavgv 601 laphsalaal edtvdypara htfddfcpec ralglqgcaf qstvaelqrl kmkvgktqey SEQ ID NO: 4 > HEV genotype 2 (M74506.1)
  1 mtprplllf llflpmlpap ptgqpsgrrr grrsggtggg fwgdrvdsqp faipyihptn 61 pfapdvaaas gsgprlrqpa rplgstwrdq aqrpsaaarr rpatagaaal tavapahdts 121 pvpdvdsrga ilrrqynlst spltssvasg tnlvlyaapl npplplqdgt nthimateas 181 nyaqvrvara tiryrplvpn avggyaisis fwpqttttpt svdmnsitst dvrilvqpgi 241 aselvipser lhyrnqgwrs vetsgvaeee atsqlvmlci hqspvnsytn tpytgalqll 301 dfalelefrn lttcntntrv srysstarhs argadgtael tttaatrfmk dlhftglngv 361 gevgrgialt llnladtllg glptelissa ggqlfysrpv vsangeptvk lytsvenaqq 421 dkgvaiphdi dlgdsrvviq dydnqheqdr ptpapaparp fsvlrandvl wlsltaaeyd 481 qstygsstgp vyisdsvtlv nvatgaqava rsldwskvtl dgrplptveg ysktffvlpl 541 rgklsfweag ttkagypyny nttasdqili enaaghrvai styttrlgag pvaisaaavl 601 aprsalalle dtfdypgrah tfddfcpecr alglqgcafq stvaelqrlk vkvgktrel SEQ ID NO: 5 > HEV genotype 5(BAJ77116)
  1 mnnmflcfac gyatmrprai llllvvllpm lpappagqss grrrgrrsgg agsgfwgdrv 61 dsqpfalpyi hptnpfasdt iaatatgars rqsarplgsa wrdqtqrppa asrrrstptg 121 aspltavapa pdtrpvpdvd srgailrrqy nlstspltst iasgtnlvly aaplspllpl 181 qdgtnthima teasnyaqyr vvratiryrp lvpnavggya isisfwpqtt ttptsvdmns 241 itstdvrivv qpglaselvi pserlhyrnq gwtsvetsgv aeeeatsglv mlcihgspvn 301 sytntpytga lglldfalel efrnltpgnt ntrvsrysst arhrlhrgad gtaelttta 361 trfmkdlxft gsngigevgr gialtlfnla dtllgglpte lissaggqlf ysrpvvsang 421 eptvklytsv enaqqdkgia iphdidlgds rvviqdydnq heqdrptpsp apsrpfsvlr 481 vndvlwltmt aaeydqttyg tstdpvyvsd tvtfvnvatg aqgvarsldw skvtldgrpl 541 ttiqrhskny fvlplrgkls fweagttkag ypynynttas dqilienaag hrvcistytt 601 algsgpvsvs SEQ ID NO: 6 > HEV genotype 6(BAJ61827.1)
  1 mrpravlllf lmllpmlpap pagqpsgrrr grrsggsggg fwgdrvdsqp falpyihptn 61 pfasdvststsa gagararqaa rplgsawrdq sqrpsasarr rptpagaspl tavapapdtt 121 pvpdvdsrga ilrrqynlst spltstvasg tnlvlyaapl gpllplqdgt nthimateas 181 nyaqqrvira tiryrplvpn avggyaisis fwpqttttpt svdmnsitst dvrilvqpgl
```

```
241 aseliipser lhyrnqgwrs vetsgvaeee atsglvmlci hgspvnsytn tpytgalgll 301 dfalelefrn ltpgntntrv srytstarhr lrrgpdgtae ltttaatrfm kdlyftgsng 361 lgevgrgial tlfnladtll gglpteliss aggqlfysrp vvsangeptv klytsvenaq 421 qdkgiaiphe idlgdsrvti qdydnqneqd rptpspapsr pfsvlrvndv lwltltaaey 481 dqttygsttn pmyvsdtvtf vnvatgaqgv araldwskvt fdgrplttvq qygksffvlp 541 lrgklsfwea gtvkagypyn ynttasdqil venapghrvc istyttnlgs gpvsisavgv 601 laphaataal SEQ ID NO: 7 > HEV genotype 1 (NP_056788.1), residues 112-608
112 avapahdtp pvpdvdsrga ilrrqynlst spltssvatg tnlvlyaapl spllplqdgt nthimateas  180

181 nyaqyrvvra tiryrplvpn avggyaisis fwpqttttpt svdmnsitst dvrilvqpgi asehvipser  250

251 lhyrnqgwrs vetsgvaeee atsglvmlci hgslvnsytn tpytgalgll dfalelefrn ltpgntntrv  320

321 srysstarhr lrrgadgtae ltttaatrfm kdlyftstng vgeigrgial tlfnladtll gglpteliss  390

391 aggqlfysrp vvsangeptv klytsvenaq qdkgialphd idlgesrvvl qdydnqheqd rptpspapsr  460

461 pfsvlrandv lwlsltaaey dqstygsstg pvyvsdsvtl vnvatgaqav arsldwtkvt ldgrplsttq  530

531 qysktffvlp lrgklsfwea gttkagypyn ynttasdqll venaaghrva istyttslga gpvsisavav  600

601 laphsala                                                                     608

SEQ ID NO: 8 > HEV genotype 3 (BAH10873.1), residues 112-608
112 aispapdta pvpdvdsrga ilrrqynlst spltssvasg tnlvlyaapl npllplqdgt nthimateas  180

181 nyaqyrvvra tiryrplvpn avggyaisis fwpqttttpt svdmnsitst dvrilvqpgi aselvipser  250

251 lhyrnqgwrs vettgvaeee atsglvmlci hgspvnsytn tpytgalgll dfalelefrn ltpgntntrv  320

321 srytstarhr lrrgadgtae ltttaatrfm kdlhftgtng vgevgrgial tlfnladtll gglpteliss  390

391 aggqlfysrp vvsangeptv klytsvenaq qdkgitiphd idlgdsrvvi qdydnqheqd rptpspapsr  460

461 pfsvlrandv lwlsltaaey dqttygsstn pmyvsdtvtf vnvatgaqav arsldwskvt ldgrplttiq  530

531 qysktfyvlp lrgklsfwea gttkagypyn ynttasdqil ienaaghrva istyttslga gptsisavgv  600

601 laphsala                                                                     608

SEQ ID NO: 9 > HEV genotype 4 (ABE271481), residues 112-608
112 avapapdta pvpdvdsrga ilrrqynlst spltstiatg tnlvlyaapl spllplqdgt nthilateas  180

181 nyaqyrvvra tiryrplvpn avggyaisis fwpqttttpt svdmnsitst dvrilvqpgl aselvipser  250

251 lhyrnqgwrs vetsgvaeee atsglvmlci hgspvnsytn tpytgalgll dfalelefrn ltpgntntrv  320

321 srysssarhk lcrgpdgtae ltttaatrfm kdlhftgtng vgevgrgial tllniadtll gglpteliss  390

391 aggqlfysrp vvsangeptv klytsvenaq qdkgiaiphd idlgesrvvi qdydnqheqd rptpspapsr  460

461 pfsvlrandv lwlsltaaey dqttygsstn pmyvsdtvtf vnvatgtqgv srsldwskvt ldgrplttiq  530

541 qysktffvlp lrgklsfwar gttkagypyn ynttasdqil ienapghrvc istyttnlgs gpvsisavgv  600

601 laphsala                                                                     608

SEQ ID NO: 10 > HEV genotype 2 (M745061), residues 112-608
112 avapahdts pvpdvdsrga ilrrgynlst spltssvasg tnlvlyaapl npplplqdgt nthimateas  180

181 nyaqyrvara tiryrplvpn avggyaisis fwpqttttpt svdmnsitst dvrilvqpgi aselvipser  250

251 lhyrnqgwrs vetsgvaeee atsglvmlci hgspvnsytn tpytgalgll dfalelefrn lttcntntrv  320

321 srysstarhs argadgtael tttaatrfmk dlhftglngv gevgrgialt llniadtllg glptelissa  390

391 qqglfysrpv vsangeptvk lytsvenaqq dkgvaiphdi dlgdsrvviq dydnqheqdr ptpspapsrp  460
```

```
461 fsvlrandvl wlsltaaeyd qstygsstgp vyisdsvtlv nvatgaqava rsldwskvtl dgrplptveq 530

531 ysktffvlpl rgklsfweag ttkagypyny nttasdqili enaaghrvai styttrlgag pvaisaaavl 600

601 aprsalal

SEQ ID NO: 11 > HEV genotype 5(BAJ77116), residues 112-608
112 srrrstptg 121 aspltavapa pdtrpvpdvd srgailrrqy nlstspltst iasgtnlvly aaplspllpl 181 qdgtnthima teasnyaqyr vvratiryrp lvpnavggva isisfwpqtt ttptsvdmns 241 itstdvrivv qpglaselvi pserlhyrnq gwrsvetsgv aeeeatsglv mlcihgspvn 301 sytntpytga lglldfalel efrnltpqnt ntrvsrysst arhrlhrgad qtaeltttaa 361 trfmkdlxft gsngigevgr gialtlfnla dtllgglpte lissaggqlf ysrpvvsang 421 eptvklytsv enaqqdkgia iphdidlgds rvviqdydnq heqdrptpsp apsrpfsvlr 481 vndvlwltmt aaeydqttyg tstdpvyvsd tvtfvnvatg aqgvarsldw skvtldgrpl 541 ttiqrhskny fvlplrgkls fweagttkag ypynynttas dqilienaag hrvcistytt 601 slgsgpvs SEQ ID NO: 12 > HEV genotype 6(BAJ61827.1), residues 112-608
112 avapapdtt 121 pvpdvdsrga iirrqynlst spltstvasg thlvlyaapl qpllplqdgt nthimateas 181 nvaqyrvira tiryrplvpn avggyaisis fwpqttttpt svdmnsitst dvrilvqpgl 241 aseliipser lhyrnqgwrs vetsgvaeee atsglvmlci hgspvnsytn tpytgalgll 301 dfalelefrn ltpqntntrv srytstarhr lrrgpdgtae ltttaatrfm kdlyftgsng 361 lgevgrgial tlfnladtll gglpteliss aggqlfysrp vvsangeptv klytsvenaq 421 qdkgiaiphe idlgdsrvti qdydnqheqd rptpspapsr pfsvlrvndv lwltltaaey 481 dqttvasttn pmyvsdtvtf vnvatgaqgv araldwskvt fdgrplttvq qygksffvlp 541 lrgklsfwea gtvkagypyn ynttasdqil venapghrvc istyttnlgs gpvsisavav 601 laphaata
```

What is claimed is:

1. A modified capsid protein comprising a portion of hepatitis E virus (HEV) open Reading Frame 2 (ORF2) protein that is able to form an acid and proteolytically stable HEV virus like particle (VLP), wherein the portion of HEV ORF2 comprises the 452-606 segment of the HEV ORF2 protein of SEQ ID NO:1, 2, 3, 4, 5, or 6, wherein at least one residue Y485, T489, S533, N573, or T586 of the HEV ORF2 protein set forth in SEQ ID NO:1 or one of the corresponding residues of SEQ ID NO:2, 3, 4, 5, or 6 is replaced with a cysteine, which is optionally chemically derivatized.

2. The modified capsid protein of claim 1, wherein the cysteine is chemically derivatized.

3. The modified capsid protein of claim 1, wherein the portion of HEV ORF2 comprises the 112-608 segment of the HEV ORF 2 protein of SEQ ID NO:1, 2, 3, 4, 5, or 6.

4. The modified capsid protein of claim 2, wherein the cysteine is alkylated, acylated, arylated, succinylated, oxidized, or conjugated to a detectable label or a bioactive agent.

5. The modified capsid protein of claim 4, wherein the detectable label comprises a fluorophore, a superparamagnetic label, an MRI contrast agent, a positron emitting isotope, or a cluster of elements of group 3 through 18 having an atomic number greater than 20.

6. A composition comprising the modified capsid protein of claim 1 and a pharmaceutically acceptable excipient.

7. A nucleic acid comprising a polynucleotide sequence encoding the modified capsid protein of claim 1.

8. An expression cassette comprising a promoter operably linked to a polynucleotide sequence encoding the modified capsid protein of claim 1.

9. A cell comprising the nucleic acid of claim 7.

10. A cell comprising the modified capsid protein of claim 1.

11. An HEV VLP comprising the modified capsid protein of claim 1.

12. A method of producing a modified capsid protein comprising cultivating the cell of claim 9 under conditions suitable to permit expression of the modified capsid protein.

13. A method of directing an HEV VLP to a target cell comprising contacting a cell with the HEV-VLP, wherein the HEV VLP comprises the modified capsid protein of claim 1, wherein the HEV VLP further comprises a cell targeting moiety having affinity for the target cell conjugated to the cysteine.

14. The modified capsid protein of claim 5, wherein the cluster of elements of group 3 through 18 having an atomic number greater than 20 is a gold nanocluster.

15. The HEV VLP of claim 11, wherein the cluster of elements of group 3 through 18 having an atomic number greater than 20 is a gold nanocluster.

16. The method of claim 13, wherein the cluster of elements of group 3 through 18 having an atomic number greater than 20 is a gold nanocluster.

17. The method of claim 13, wherein the HEV VLP further comprises an encapsulated bioactive agent and delivers the bioactive agent to the target cell.

* * * * *

SEQUENCE LISTING

<160> NUMBER OF SEQ IDS NOS: 33

<210> SEQ ID NO 1
<211> LENGTH: 660
<212> TYPE: PRT
<213> ORGANISM: Hepatitis E virus

<400> SEQUENCE: 1

```
Met Arg Pro Arg Pro Ile Leu Leu Leu Leu Met Phe Leu Pro Met
1               5                   10                  15

Leu Pro Ala Pro Pro Gly Gln Pro Ser Gly Arg Arg Gly Arg
            20                  25                  30

Arg Ser Gly Gly Ser Gly Gly Gly Phe Trp Gly Asp Arg Ala Asp Ser
            35                  40                  45

Gln Pro Phe Ala Ile Pro Tyr Ile His Pro Thr Asn Pro Phe Ala Pro
        50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Ala
                85                  90                  95
```

-continued

Ala Ser Arg Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
            115                 120                 125

Gly Ala Ile Leu Arg Arg Gln Tyr Asn Leu Ser Thr Ser Pro Leu Thr
130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Thr Pro Thr Ser Val Asp Met
            210                 215                 220

Asn Ser Ile Thr Ser Thr Asp Val Arg Ile Leu Val Gln Pro Gly Ile
225                 230                 235                 240

Ala Ser Glu His Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Leu Val Asn Ser Tyr
            275                 280                 285

Thr Asn Thr Pro Tyr Thr Gly Ala Leu Gly Leu Leu Asp Phe Ala Leu
            290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
            340                 345                 350

Leu Tyr Phe Thr Ser Thr Asn Gly Val Gly Ile Gly Arg Gly Ile
            355                 360                 365

Ala Leu Thr Leu Phe Asn Leu Ala Asp Thr Leu Leu Gly Gly Leu Pro
            370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
            420                 425                 430

Leu Gly Glu Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
            450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
            500                 505                 510

```
Ser Leu Asp Trp Thr Lys Val Thr Leu Asp Gly Arg Pro Leu Ser Thr
            515                 520                 525

Thr Gln Gln Tyr Ser Lys Thr Phe Phe Val Leu Pro Leu Arg Gly Lys
        530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
            580                 585                 590

Val Ser Ile Ser Ala Val Ala Val Leu Ala Pro His Ser Ala Leu Ala
        595                 600                 605

Leu Leu Glu Asp Thr Met Asp Tyr Pro Ala Arg Ala His Thr Phe Asp
610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

<210> SEQ ID NO 2
<211> LENGTH: 660
<212> TYPE: PRT
<213> ORGANISM: Hepatitis E virus

<400> SEQUENCE: 2

Met Arg Pro Arg Ala Val Leu Leu Phe Phe Val Leu Leu Pro Met
1               5                  10                  15

Leu Pro Ala Pro Pro Ala Gly Gln Pro Ser Gly Arg Arg Gly Arg
            20                  25                  30

Arg Ser Gly Gly Ala Gly Gly Gly Phe Trp Gly Asp Arg Val Asp Ser
        35                  40                  45

Gln Pro Phe Ala Leu Pro Tyr Ile His Pro Thr Asn Pro Phe Ala Ala
    50                  55                  60

Asp Val Val Ser Gln Ser Gly Ala Gly Ala Arg Pro Arg Gln Pro Pro
65                  70                  75                  80

Arg Pro Leu Gly Ser Ala Trp Arg Asp Gln Ser Gln Arg Pro Ser Ala
                85                  90                  95

Ala Pro Arg Arg Arg Ser Ala Pro Ala Gly Ala Ala Pro Leu Thr Ala
            100                 105                 110

Ile Ser Pro Ala Pro Asp Thr Ala Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Ser Val Ala Ser Gly Thr Asn Leu Val Leu Tyr Ala Ala Pro Leu
145                 150                 155                 160

Asn Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Thr Pro Thr Ser Val Asp Met
    210                 215                 220
```

```
Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
            245                 250                 255

Gly Trp Arg Ser Val Glu Thr Thr Gly Val Ala Glu Glu Ala Thr
        260                 265                 270

Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
                340                 345                 350

Leu His Phe Thr Gly Thr Asn Gly Val Gly Glu Val Gly Arg Gly Ile
            355                 360                 365

Ala Leu Thr Leu Phe Asn Leu Ala Asp Thr Leu Leu Gly Gly Leu Pro
370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Thr Ile Pro His Asp Ile Asp
                420                 425                 430

Leu Gly Asp Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
450                 455                 460

Leu Arg Ala Asn Asp Val Leu Trp Leu Ser Leu Thr Ala Ala Glu Tyr
465                 470                 475                 480

Asp Gln Thr Thr Tyr Gly Ser Ser Thr Asn Pro Met Tyr Val Ser Asp
                485                 490                 495

Thr Val Thr Phe Val Asn Val Ala Thr Gly Ala Gln Ala Val Ala Arg
            500                 505                 510

Ser Leu Asp Trp Ser Lys Val Thr Leu Asp Gly Arg Pro Leu Thr Thr
            515                 520                 525

Ile Gln Gln Tyr Ser Lys Thr Phe Tyr Val Leu Pro Leu Arg Gly Lys
            530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Ile Leu Ile Glu Asn Ala Ala Gly
            565                 570                 575

His Arg Val Ala Ile Ser Thr Tyr Thr Thr Ser Leu Gly Ala Gly Pro
            580                 585                 590

Thr Ser Ile Ser Ala Val Gly Val Leu Ala Pro His Ser Ala Leu Ala
            595                 600                 605

Val Leu Glu Asp Thr Thr Asp Tyr Pro Ala Arg Ala His Thr Phe Asp
            610                 615                 620

Asp Phe Cys Pro Glu Cys Arg Thr Leu Gly Leu Gln Gly Cys Ala Phe
625                 630                 635                 640
```

-continued

Gln Ser Thr Ile Ala Glu Leu Gln Arg Leu Lys Met Lys Val Gly Lys
                645                 650                 655

Thr Arg Glu Ser
        660

<210> SEQ ID NO 3
<211> LENGTH: 660
<212> TYPE: PRT
<213> ORGANISM: Hepatitis E virus

<400> SEQUENCE: 3

Met Arg Pro Arg Ala Val Leu Leu Phe Val Leu Leu Pro Met
 1               5                  10                  15

Leu Pro Ala Pro Pro Ala Gly Gln Pro Ser Gly Arg Arg Gly Arg
                20                  25                  30

Arg Ser Gly Gly Thr Gly Gly Gly Phe Trp Gly Asp Arg Val Asp Ser
            35                  40                  45

Gln Pro Phe Ala Leu Pro Tyr Ile His Pro Thr Asn Pro Phe Ala Ser
    50                  55                  60

Asp Ile Pro Thr Ala Thr Gly Ala Gly Ala Arg Pro Arg Gln Pro Ala
65                  70                  75                  80

Arg Pro Leu Gly Ser Ala Trp Arg Asp Gln Ser Gln Arg Pro Ala Ala
                85                  90                  95

Pro Ala Arg Arg Arg Ser Ala Pro Ala Gly Ala Ser Pro Leu Thr Ala
            100                 105                 110

Val Ala Pro Ala Pro Asp Thr Ala Pro Val Pro Asp Val Asp Ser Arg
        115                 120                 125

Gly Ala Ile Leu Arg Arg Gln Tyr Asn Leu Ser Thr Ser Pro Leu Thr
130                 135                 140

Ser Thr Ile Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Ile Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Ser Ser Ser Ala Arg His Lys Leu Cys Arg Gly Pro Asp
                325                 330                 335

Gly Thr Ala Glu Leu Thr Thr Thr Ala Ala Thr Arg Phe Met Lys Asp
            340                 345                 350

-continued

Leu His Phe Thr Gly Thr Asn Gly Val Gly Val Gly Arg Gly Ile
        355                 360                 365

Ala Leu Thr Leu Leu Asn Leu Ala Asp Thr Leu Leu Gly Gly Leu Pro
    370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
            420                 425                 430

Leu Gly Glu Ser Arg Val Val Ile Gln Asp Tyr Asp Asn Gln His Glu
        435                 440                 445

Gln Asp Arg Pro Thr Pro Ser Pro Ala Pro Ser Arg Pro Phe Ser Val
    450                 455                 460

Leu Arg Ala Asn Asp Val Leu Trp Leu Ser Leu Thr Ala Ala Glu Tyr
465                 470                 475                 480

Asp Gln Thr Thr Tyr Gly Ser Ser Thr Asn Pro Met Tyr Val Ser Asp
                485                 490                 495

Thr Val Thr Phe Val Asn Val Ala Thr Gly Thr Gln Gly Val Ser Arg
            500                 505                 510

Ser Leu Asp Trp Ser Lys Val Thr Leu Asp Gly Arg Pro Leu Thr Thr
        515                 520                 525

Ile Gln Gln Tyr Ser Lys Thr Phe Phe Val Leu Pro Leu Arg Gly Lys
    530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Ile Leu Ile Glu Asn Ala Pro Gly
                565                 570                 575

His Arg Val Cys Ile Ser Thr Tyr Thr Thr Asn Leu Gly Ser Gly Pro
            580                 585                 590

Val Ser Ile Ser Ala Val Gly Val Leu Ala Pro His Ser Ala Leu Ala
        595                 600                 605

Ala Leu Glu Asp Thr Val Asp Tyr Pro Ala Arg Ala His Thr Phe Asp
    610                 615                 620

Asp Phe Cys Pro Glu Cys Arg Ala Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Gln Glu Tyr
            660

<210> SEQ ID NO 4
<211> LENGTH: 659
<212> TYPE: PRT
<213> ORGANISM: Hepatitis E virus

<400> SEQUENCE: 4

Met Arg Pro Arg Pro Leu Leu Leu Phe Leu Leu Phe Leu Pro Met
1               5                   10                  15

Leu Pro Ala Pro Pro Thr Gly Gln Pro Ser Gly Arg Arg Gly Arg
                20                  25                  30

Arg Ser Gly Gly Thr Gly Gly Gly Phe Trp Gly Asp Arg Val Asp Ser
            35                  40                  45

Gln Pro Phe Ala Ile Pro Tyr Ile His Pro Thr Asn Pro Phe Ala Pro

```
                50                  55                  60
Asp Val Ala Ala Ala Ser Gly Ser Gly Pro Arg Leu Arg Gln Pro Ala
 65                  70                  75                  80

Arg Pro Leu Gly Ser Thr Trp Arg Asp Gln Ala Gln Arg Pro Ser Ala
                 85                  90                  95

Ala Ser Arg Arg Arg Pro Ala Thr Ala Gly Ala Ala Ala Leu Thr Ala
                100                 105                 110

Val Ala Pro Ala His Asp Thr Ser Pro Val Pro Asp Val Asp Ser Arg
                115                 120                 125

Gly Ala Ile Leu Arg Arg Gln Tyr Asn Leu Ser Thr Ser Pro Leu Thr
130                 135                 140

Ser Ser Val Ala Ser Gly Thr Asn Leu Val Leu Tyr Ala Ala Pro Leu
145                 150                 155                 160

Asn Pro Pro Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
                180                 185                 190

Arg Tyr Arg Pro Leu Val Pro Asn Ala Val Gly Gly Tyr Ala Ile Ser
                195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
                260                 265                 270

Ser Gly Leu Val Met Leu Cys Ile His Gly Ser Pro Val Asn Ser Tyr
                275                 280                 285

Thr Asn Thr Pro Tyr Thr Gly Ala Leu Gly Leu Leu Asp Phe Ala Leu
                290                 295                 300

Glu Leu Glu Phe Arg Asn Leu Thr Thr Cys Asn Thr Asn Thr Arg Val
305                 310                 315                 320

Ser Arg Tyr Ser Ser Thr Ala Arg His Ser Ala Arg Gly Ala Asp Gly
                325                 330                 335

Thr Ala Glu Leu Thr Thr Thr Ala Ala Thr Arg Phe Met Lys Asp Leu
                340                 345                 350

His Phe Thr Gly Leu Asn Gly Val Gly Glu Val Gly Arg Gly Ile Ala
                355                 360                 365

Leu Thr Leu Leu Asn Leu Ala Asp Thr Leu Leu Gly Gly Leu Pro Thr
370                 375                 380

Glu Leu Ile Ser Ser Ala Gly Gly Gln Leu Phe Tyr Ser Arg Pro Val
385                 390                 395                 400

Val Ser Ala Asn Gly Glu Pro Thr Val Lys Leu Tyr Thr Ser Val Glu
                405                 410                 415

Asn Ala Gln Gln Asp Lys Gly Val Ala Ile Pro His Asp Ile Asp Leu
                420                 425                 430

Gly Asp Ser Arg Val Val Ile Gln Asp Tyr Asp Asn Gln His Glu Gln
                435                 440                 445

Asp Arg Pro Thr Pro Ser Pro Ala Pro Ser Arg Pro Phe Ser Val Leu
                450                 455                 460

Arg Ala Asn Asp Val Leu Trp Leu Ser Leu Thr Ala Ala Glu Tyr Asp
465                 470                 475                 480
```

```
Gln Ser Thr Tyr Gly Ser Ser Thr Gly Pro Val Tyr Ile Ser Asp Ser
                485                 490                 495

Val Thr Leu Val Asn Val Ala Thr Gly Ala Gln Ala Val Ala Arg Ser
            500                 505                 510

Leu Asp Trp Ser Lys Val Thr Leu Asp Gly Arg Pro Leu Pro Thr Val
        515                 520                 525

Glu Gln Tyr Ser Lys Thr Phe Phe Val Leu Pro Leu Arg Gly Lys Leu
    530                 535                 540

Ser Phe Trp Glu Ala Gly Thr Thr Lys Ala Gly Tyr Pro Tyr Asn Tyr
545                 550                 555                 560

Asn Thr Thr Ala Ser Asp Gln Ile Leu Ile Glu Asn Ala Ala Gly His
                565                 570                 575

Arg Val Ala Ile Ser Thr Tyr Thr Thr Arg Leu Gly Ala Gly Pro Val
            580                 585                 590

Ala Ile Ser Ala Ala Ala Val Leu Ala Pro Arg Ser Ala Leu Ala Leu
        595                 600                 605

Leu Glu Asp Thr Phe Asp Tyr Pro Gly Arg Ala His Thr Phe Asp Asp
    610                 615                 620

Phe Cys Pro Glu Cys Arg Ala Leu Gly Leu Gln Gly Cys Ala Phe Gln
625                 630                 635                 640

Ser Thr Val Ala Glu Leu Gln Arg Leu Lys Val Lys Val Gly Lys Thr
                645                 650                 655

Arg Glu Leu

<210> SEQ ID NO 5
<211> LENGTH: 610
<212> TYPE: PRT
<213> ORGANISM: Hepatitis E virus
<220> FEATURE:
<221> NAME/KEY: misc_feature
<222> LOCATION: (368)..(368)
<223> OTHER INFORMATION: Xaa can be any naturally occurring amino acid

<400> SEQUENCE: 5

Met Asn Asn Met Phe Leu Cys Phe Ala Cys Gly Tyr Ala Thr Met Arg
1               5                   10                  15

Pro Arg Ala Ile Leu Leu Leu Val Val Leu Leu Pro Met Leu Pro
            20                  25                  30

Ala Pro Pro Ala Gly Gln Ser Ser Gly Arg Arg Gly Arg Arg Ser
        35                  40                  45

Gly Gly Ala Gly Ser Gly Phe Trp Gly Asp Arg Val Asp Ser Gln Pro
    50                  55                  60

Phe Ala Leu Pro Tyr Ile His Pro Thr Asn Pro Phe Ala Ser Asp Thr
65                  70                  75                  80

Ile Ala Ala Thr Gly Thr Gly Ala Arg Ser Arg Gln Ser Ala Arg Pro
                85                  90                  95

Leu Gly Ser Ala Trp Arg Asp Gln Thr Gln Arg Pro Ala Ala Ser
            100                 105                 110

Arg Arg Arg Ser Thr Pro Thr Gly Ala Ser Pro Leu Thr Ala Val Ala
        115                 120                 125

Pro Ala Pro Asp Thr Arg Pro Val Pro Asp Val Asp Ser Arg Gly Ala
    130                 135                 140

Ile Leu Arg Arg Gln Tyr Asn Leu Ser Thr Ser Pro Leu Thr Ser Thr
145                 150                 155                 160

Ile Ala Ser Gly Thr Asn Leu Val Leu Tyr Ala Ala Pro Leu Ser Pro
```

```
                165                 170                 175
Leu Leu Pro Leu Gln Asp Gly Thr Asn Thr His Ile Met Ala Thr Glu
            180                 185                 190

Ala Ser Asn Tyr Ala Gln Tyr Arg Val Val Arg Ala Thr Ile Arg Tyr
            195                 200                 205

Arg Pro Leu Val Pro Asn Ala Val Gly Gly Tyr Ala Ile Ser Ile Ser
            210                 215                 220

Phe Trp Pro Gln Thr Thr Thr Pro Thr Ser Val Asp Met Asn Ser
225                 230                 235                 240

Ile Thr Ser Thr Asp Val Arg Ile Val Gln Pro Gly Leu Ala Ser
                245                 250                 255

Glu Leu Val Ile Pro Ser Glu Arg Leu His Tyr Arg Asn Gln Gly Trp
            260                 265                 270

Arg Ser Val Glu Thr Ser Gly Val Ala Glu Glu Ala Thr Ser Gly
            275                 280                 285

Leu Val Met Leu Cys Ile His Gly Ser Pro Val Asn Ser Tyr Thr Asn
            290                 295                 300

Thr Pro Tyr Thr Gly Ala Leu Gly Leu Leu Asp Phe Ala Leu Glu Leu
305                 310                 315                 320

Glu Phe Arg Asn Leu Thr Pro Gly Asn Thr Asn Thr Arg Val Ser Arg
                325                 330                 335

Tyr Ser Ser Thr Ala Arg His Arg Leu His Arg Gly Ala Asp Gly Thr
            340                 345                 350

Ala Glu Leu Thr Thr Thr Ala Ala Thr Arg Phe Met Lys Asp Leu Xaa
            355                 360                 365

Phe Thr Gly Ser Asn Gly Ile Gly Glu Val Gly Arg Gly Ile Ala Leu
            370                 375                 380

Thr Leu Phe Asn Leu Ala Asp Thr Leu Leu Gly Gly Leu Pro Thr Glu
385                 390                 395                 400

Leu Ile Ser Ser Ala Gly Gly Gln Leu Phe Tyr Ser Arg Pro Val Val
                405                 410                 415

Ser Ala Asn Gly Glu Pro Thr Val Lys Leu Tyr Thr Ser Val Glu Asn
            420                 425                 430

Ala Gln Gln Asp Lys Gly Ile Ala Ile Pro His Asp Ile Asp Leu Gly
            435                 440                 445

Asp Ser Arg Val Val Ile Gln Asp Tyr Asp Asn Gln His Glu Gln Asp
            450                 455                 460

Arg Pro Thr Pro Ser Pro Ala Pro Ser Arg Pro Phe Ser Val Leu Arg
465                 470                 475                 480

Val Asn Asp Val Leu Trp Leu Thr Met Thr Ala Ala Glu Tyr Asp Gln
                485                 490                 495

Thr Thr Tyr Gly Thr Ser Thr Asp Pro Val Tyr Val Ser Asp Thr Val
            500                 505                 510

Thr Phe Val Asn Val Ala Thr Gly Ala Gln Gly Val Ala Arg Ser Leu
            515                 520                 525

Asp Trp Ser Lys Val Thr Leu Asp Gly Arg Pro Leu Thr Thr Ile Gln
            530                 535                 540

Arg His Ser Lys Asn Tyr Phe Val Leu Pro Leu Arg Gly Lys Leu Ser
545                 550                 555                 560

Phe Trp Glu Ala Gly Thr Thr Lys Ala Gly Tyr Pro Tyr Asn Tyr Asn
                565                 570                 575

Thr Thr Ala Ser Asp Gln Ile Leu Ile Glu Asn Ala Ala Gly His Arg
            580                 585                 590
```

```
Val Cys Ile Ser Thr Tyr Thr Thr Ser Leu Gly Ser Gly Pro Val Ser
            595                 600                 605
Val Ser
    610

<210> SEQ ID NO 6
<211> LENGTH: 610
<212> TYPE: PRT
<213> ORGANISM: Hepatitis E virus

<400> SEQUENCE: 6

Met Arg Pro Arg Ala Val Leu Leu Phe Leu Met Leu Leu Pro Met
1               5                   10                  15

Leu Pro Ala Pro Pro Ala Gly Gln Pro Ser Gly Arg Arg Gly Arg
                20                  25                  30

Arg Ser Gly Gly Ser Gly Gly Phe Trp Gly Asp Arg Val Asp Ser
            35                  40                  45

Gln Pro Phe Ala Leu Pro Tyr Ile His Pro Thr Asn Pro Phe Ala Ser
50                      55                  60

Asp Val Ser Thr Ser Ala Gly Ala Gly Ala Arg Ala Arg Gln Ala Ala
65                  70                  75                  80

Arg Pro Leu Gly Ser Ala Trp Arg Asp Gln Ser Gln Arg Pro Ser Ala
                85                  90                  95

Ser Ala Arg Arg Arg Pro Thr Pro Ala Gly Ala Ser Pro Leu Thr Ala
                100                 105                 110

Val Ala Pro Ala Pro Asp Thr Thr Pro Val Pro Asp Val Asp Ser Arg
                115                 120                 125

Gly Ala Ile Leu Arg Arg Gln Tyr Asn Leu Ser Thr Ser Pro Leu Thr
            130                 135                 140

Ser Thr Val Ala Ser Gly Thr Asn Leu Val Leu Tyr Ala Ala Pro Leu
145                 150                 155                 160

Gly Pro Leu Leu Pro Leu Gln Asp Gly Thr Asn Thr His Ile Met Ala
                165                 170                 175

Thr Glu Ala Ser Asn Tyr Ala Gln Tyr Arg Val Ile Arg Ala Thr Ile
                180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Leu
225                 230                 235                 240

Ala Ser Glu Leu Ile Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
                275                 280                 285

Thr Asn Thr Pro Tyr Thr Gly Ala Leu Gly Leu Leu Asp Phe Ala Leu
            290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Pro Asp
                325                 330                 335

Gly Thr Ala Glu Leu Thr Thr Thr Ala Ala Thr Arg Phe Met Lys Asp
```

```
                   340                 345                 350
Leu Tyr Phe Thr Gly Ser Asn Gly Leu Gly Glu Val Gly Arg Gly Ile
            355                 360                 365

Ala Leu Thr Leu Phe Asn Leu Ala Asp Thr Leu Leu Gly Gly Leu Pro
        370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Glu Ile Asp
            420                 425                 430

Leu Gly Asp Ser Arg Val Thr Ile Gln Asp Tyr Asp Asn Gln His Glu
        435                 440                 445

Gln Asp Arg Pro Thr Pro Ser Pro Ala Pro Ser Arg Pro Phe Ser Val
    450                 455                 460

Leu Arg Val Asn Asp Val Leu Trp Leu Thr Leu Thr Ala Ala Glu Tyr
465                 470                 475                 480

Asp Gln Thr Thr Tyr Gly Ser Thr Thr Asn Pro Met Tyr Val Ser Asp
                485                 490                 495

Thr Val Thr Phe Val Asn Val Ala Thr Gly Ala Gln Gly Val Ala Arg
            500                 505                 510

Ala Leu Asp Trp Ser Lys Val Thr Phe Asp Gly Arg Pro Leu Thr Thr
        515                 520                 525

Val Gln Gln Tyr Gly Lys Ser Phe Phe Val Leu Pro Leu Arg Gly Lys
    530                 535                 540

Leu Ser Phe Trp Glu Ala Gly Thr Val Lys Ala Gly Tyr Pro Tyr Asn
545                 550                 555                 560

Tyr Asn Thr Thr Ala Ser Asp Gln Ile Leu Val Glu Asn Ala Pro Gly
                565                 570                 575

His Arg Val Cys Ile Ser Thr Tyr Thr Thr Asn Leu Gly Ser Gly Pro
            580                 585                 590

Val Ser Ile Ser Ala Val Gly Val Leu Ala Pro His Ala Ala Thr Ala
        595                 600                 605

Ala Leu
    610

<210> SEQ ID NO 7
<211> LENGTH: 497
<212> TYPE: PRT
<213> ORGANISM: Hepatitis E virus

<400> SEQUENCE: 7

Ala Val Ala Pro Ala His Asp Thr Pro Pro Val Pro Asp Val Asp Ser
1               5                   10                  15

Arg Gly Ala Ile Leu Arg Arg Gln Tyr Asn Leu Ser Thr Ser Pro Leu
            20                  25                  30

Thr Ser Ser Val Ala Thr Gly Thr Asn Leu Val Leu Tyr Ala Ala Pro
        35                  40                  45

Leu Ser Pro Leu Leu Pro Leu Gln Asp Gly Thr Asn Thr His Ile Met
    50                  55                  60

Ala Thr Glu Ala Ser Asn Tyr Ala Gln Tyr Arg Val Val Arg Ala Thr
65                  70                  75                  80

Ile Arg Tyr Arg Pro Leu Val Pro Asn Ala Val Gly Gly Tyr Ala Ile
                85                  90                  95
```

Ser Ile Ser Phe Trp Pro Gln Thr Thr Thr Pro Thr Ser Val Asp
                100                 105                 110

Met Asn Ser Ile Thr Ser Asp Val Arg Ile Leu Val Gln Pro Gly
        115                 120                 125

Ile Ala Ser Glu His Val Ile Pro Ser Glu Arg Leu His Tyr Arg Asn
130                 135                 140

Gln Gly Trp Arg Ser Val Glu Thr Ser Gly Val Ala Glu Glu Ala
145                 150                 155                 160

Thr Ser Gly Leu Val Met Leu Cys Ile His Gly Ser Leu Val Asn Ser
                165                 170                 175

Tyr Thr Asn Thr Pro Tyr Thr Gly Ala Leu Gly Leu Leu Asp Phe Ala
            180                 185                 190

Leu Glu Leu Glu Phe Arg Asn Leu Thr Pro Gly Asn Thr Asn Thr Arg
        195                 200                 205

Val Ser Arg Tyr Ser Ser Thr Ala Arg His Arg Leu Arg Arg Gly Ala
210                 215                 220

Asp Gly Thr Ala Glu Leu Thr Thr Ala Ala Thr Arg Phe Met Lys
225                 230                 235                 240

Asp Leu Tyr Phe Thr Ser Thr Asn Gly Val Gly Glu Ile Gly Arg Gly
                245                 250                 255

Ile Ala Leu Thr Leu Phe Asn Leu Ala Asp Thr Leu Leu Gly Gly Leu
            260                 265                 270

Pro Thr Glu Leu Ile Ser Ser Ala Gly Gly Gln Leu Phe Tyr Ser Arg
        275                 280                 285

Pro Val Val Ser Ala Asn Gly Glu Pro Thr Val Lys Leu Tyr Thr Ser
290                 295                 300

Val Glu Asn Ala Gln Gln Asp Lys Gly Ile Ala Ile Pro His Asp Ile
305                 310                 315                 320

Asp Leu Gly Glu Ser Arg Val Val Ile Gln Asp Tyr Asp Asn Gln His
                325                 330                 335

Glu Gln Asp Arg Pro Thr Pro Ser Pro Ala Pro Ser Arg Pro Phe Ser
            340                 345                 350

Val Leu Arg Ala Asn Asp Val Leu Trp Leu Ser Leu Thr Ala Ala Glu
        355                 360                 365

Tyr Asp Gln Ser Thr Tyr Gly Ser Ser Thr Gly Pro Val Tyr Val Ser
370                 375                 380

Asp Ser Val Thr Leu Val Asn Val Ala Thr Gly Ala Gln Ala Val Ala
385                 390                 395                 400

Arg Ser Leu Asp Trp Thr Lys Val Thr Leu Asp Gly Arg Pro Leu Ser
                405                 410                 415

Thr Thr Gln Gln Tyr Ser Lys Thr Phe Phe Val Leu Pro Leu Arg Gly
            420                 425                 430

Lys Leu Ser Phe Trp Glu Ala Gly Thr Thr Lys Ala Gly Tyr Pro Tyr
        435                 440                 445

Asn Tyr Asn Thr Thr Ala Ser Asp Gln Leu Leu Val Glu Asn Ala Ala
450                 455                 460

Gly His Arg Val Ala Ile Ser Thr Tyr Thr Thr Ser Leu Gly Ala Gly
465                 470                 475                 480

Pro Val Ser Ile Ser Ala Val Ala Val Leu Ala Pro His Ser Ala Leu
                485                 490                 495

Ala

<210> SEQ ID NO 8

```
<211> LENGTH: 497
<212> TYPE: PRT
<213> ORGANISM: Hepatitis E virus

<400> SEQUENCE: 8
```

| | | | |

```
385                 390                 395                 400
Arg Ser Leu Asp Trp Ser Lys Val Thr Leu Asp Gly Arg Pro Leu Thr
                405                 410                 415
Thr Ile Gln Gln Tyr Ser Lys Thr Phe Tyr Val Leu Pro Leu Arg Gly
                420                 425                 430
Lys Leu Ser Phe Trp Glu Ala Gly Thr Thr Lys Ala Gly Tyr Pro Tyr
                435                 440                 445
Asn Tyr Asn Thr Thr Ala Ser Asp Gln Ile Leu Ile Glu Asn Ala Ala
            450                 455                 460
Gly His Arg Val Ala Ile Ser Thr Tyr Thr Thr Ser Leu Gly Ala Gly
465                 470                 475                 480
Pro Thr Ser Ile Ser Ala Val Gly Val Leu Ala Pro His Ser Ala Leu
                485                 490                 495
Ala

<210> SEQ ID NO 9
<211> LENGTH: 497
<212> TYPE: PRT
<213> ORGANISM: Hepatitis E virus

<400> SEQUENCE: 9

Ala Val Ala Pro Ala Pro Asp Thr Ala Pro Val Pro Asp Val Asp Ser
1               5                   10                  15
Arg Gly Ala Ile Leu Arg Arg Gln Tyr Asn Leu Ser Thr Ser Pro Leu
                20                  25                  30
Thr Ser Thr Ile Ala Thr Gly Thr Asn Leu Val Leu Tyr Ala Ala Pro
            35                  40                  45
Leu Ser Pro Leu Leu Pro Leu Gln Asp Gly Thr Asn Thr His Ile Ile
        50                  55                  60
Ala Thr Glu Ala Ser Asn Tyr Ala Gln Tyr Arg Val Val Arg Ala Thr
65                  70                  75                  80
Ile Arg Tyr Arg Pro Leu Val Pro Asn Ala Val Gly Gly Tyr Ala Ile
                85                  90                  95
Ser Ile Ser Phe Trp Pro Gln Thr Thr Thr Thr Pro Thr Ser Val Asp
                100                 105                 110
Met Asn Ser Ile Thr Ser Thr Asp Val Arg Ile Leu Val Gln Pro Gly
            115                 120                 125
Ile Ala Ser Glu Leu Val Ile Pro Ser Glu Arg Leu His Tyr Arg Asn
        130                 135                 140
Gln Gly Trp Arg Ser Val Glu Thr Ser Gly Val Ala Glu Glu Glu Ala
145                 150                 155                 160
Thr Ser Gly Leu Val Met Leu Cys Ile His Gly Ser Pro Val Asn Ser
                165                 170                 175
Tyr Thr Asn Thr Pro Tyr Thr Gly Ala Leu Gly Leu Leu Asp Phe Ala
                180                 185                 190
Leu Glu Leu Glu Phe Arg Asn Leu Thr Pro Gly Asn Thr Asn Thr Arg
            195                 200                 205
Val Ser Arg Tyr Ser Ser Ala Arg His Lys Leu Cys Arg Gly Pro
        210                 215                 220
Asp Gly Thr Ala Glu Leu Thr Thr Thr Ala Ala Thr Arg Phe Met Lys
225                 230                 235                 240
Asp Leu His Phe Thr Gly Thr Asn Gly Val Gly Glu Val Gly Arg Gly
                245                 250                 255
Ile Ala Leu Thr Leu Leu Asn Leu Ala Asp Thr Leu Leu Gly Gly Leu
```

```
                260             265             270
Pro Thr Glu Leu Ile Ser Ser Ala Gly Gly Gln Leu Phe Tyr Ser Arg
            275                 280                 285
Pro Val Val Ser Ala Asn Gly Glu Pro Thr Val Lys Leu Tyr Thr Ser
        290                 295                 300
Val Glu Asn Ala Gln Gln Asp Lys Gly Ile Ala Ile Pro His Asp Ile
305                 310                 315                 320
Asp Leu Gly Glu Ser Arg Val Val Ile Gln Asp Tyr Asp Asn Gln His
                325                 330                 335
Glu Gln Asp Arg Pro Thr Pro Ser Pro Ala Pro Ser Arg Pro Phe Ser
            340                 345                 350
Val Leu Arg Ala Asn Asp Val Leu Trp Leu Ser Leu Thr Ala Ala Glu
        355                 360                 365
Tyr Asp Gln Thr Thr Tyr Gly Ser Ser Thr Asn Pro Met Tyr Val Ser
    370                 375                 380
Asp Thr Val Thr Phe Val Asn Val Ala Thr Gly Thr Gln Gly Val Ser
385                 390                 395                 400
Arg Ser Leu Asp Trp Ser Lys Val Thr Leu Asp Gly Arg Pro Leu Thr
                405                 410                 415
Thr Ile Gln Gln Tyr Ser Lys Thr Phe Phe Val Leu Pro Leu Arg Gly
            420                 425                 430
Lys Leu Ser Phe Trp Glu Ala Gly Thr Thr Lys Ala Gly Tyr Pro Tyr
        435                 440                 445
Asn Tyr Asn Thr Thr Ala Ser Asp Gln Ile Leu Ile Glu Asn Ala Pro
    450                 455                 460
Gly His Arg Val Cys Ile Ser Thr Tyr Thr Thr Asn Leu Gly Ser Gly
465                 470                 475                 480
Pro Val Ser Ile Ser Ala Val Gly Val Leu Ala Pro His Ser Ala Leu
                485                 490                 495
Ala

<210> SEQ ID NO 10
<211> LENGTH: 497
<212> TYPE: PRT
<213> ORGANISM: Hepatitis E virus

<400> SEQUENCE: 10

Ala Val Ala Pro Ala His Asp Thr Ser Pro Val Pro Asp Val Asp Ser
1               5                   10                  15
Arg Gly Ala Ile Leu Arg Arg Gln Tyr Asn Leu Ser Thr Ser Pro Leu
            20                  25                  30
Thr Ser Ser Val Ala Ser Gly Thr Asn Leu Val Leu Tyr Ala Ala Pro
        35                  40                  45
Leu Asn Pro Pro Leu Pro Leu Gln Asp Gly Thr Asn Thr His Ile Met
    50                  55                  60
Ala Thr Glu Ala Ser Asn Tyr Ala Gln Tyr Arg Val Ala Arg Ala Thr
65                  70                  75                  80
Ile Arg Tyr Arg Pro Leu Val Pro Asn Ala Val Gly Gly Tyr Ala Ile
                85                  90                  95
Ser Ile Ser Phe Trp Pro Gln Thr Thr Thr Thr Pro Thr Ser Val Asp
            100                 105                 110
Met Asn Ser Ile Thr Ser Thr Asp Val Arg Ile Leu Val Gln Pro Gly
        115                 120                 125
Ile Ala Ser Glu Leu Val Ile Pro Ser Glu Arg Leu His Tyr Arg Asn
```

```
                130                 135                 140
Gln Gly Trp Arg Ser Val Glu Thr Ser Gly Val Ala Glu Glu Ala
145                 150                 155                 160

Thr Ser Gly Leu Val Met Leu Cys Ile His Gly Ser Pro Val Asn Ser
            165                 170                 175

Tyr Thr Asn Thr Pro Tyr Thr Gly Ala Leu Gly Leu Leu Asp Phe Ala
        180                 185                 190

Leu Glu Leu Glu Phe Arg Asn Leu Thr Thr Cys Asn Thr Asn Thr Arg
    195                 200                 205

Val Ser Arg Tyr Ser Ser Thr Ala Arg His Ser Ala Arg Gly Ala Asp
210                 215                 220

Gly Thr Ala Glu Leu Thr Thr Ala Ala Thr Arg Phe Met Lys Asp
225                 230                 235                 240

Leu His Phe Thr Gly Leu Asn Gly Val Gly Glu Val Gly Arg Gly Ile
            245                 250                 255

Ala Leu Thr Leu Leu Asn Leu Ala Asp Thr Leu Leu Gly Gly Leu Pro
        260                 265                 270

Thr Glu Leu Ile Ser Ser Ala Gly Gly Gln Leu Phe Tyr Ser Arg Pro
    275                 280                 285

Val Val Ser Ala Asn Gly Glu Pro Thr Val Lys Leu Tyr Thr Ser Val
290                 295                 300

Glu Asn Ala Gln Gln Asp Lys Gly Val Ala Ile Pro His Asp Ile Asp
305                 310                 315                 320

Leu Gly Asp Ser Arg Val Val Ile Gln Asp Tyr Asp Asn Gln His Glu
            325                 330                 335

Gln Asp Arg Pro Thr Pro Ser Pro Ala Pro Ser Arg Pro Phe Ser Val
        340                 345                 350

Leu Arg Ala Asn Asp Val Leu Trp Leu Ser Leu Thr Ala Ala Glu Tyr
    355                 360                 365

Asp Gln Ser Thr Tyr Gly Ser Ser Thr Gly Pro Val Tyr Ile Ser Asp
370                 375                 380

Ser Val Thr Leu Val Asn Val Ala Thr Gly Ala Gln Ala Val Ala Arg
385                 390                 395                 400

Ser Leu Asp Trp Ser Lys Val Thr Leu Asp Gly Arg Pro Leu Pro Thr
            405                 410                 415

Val Glu Gln Tyr Ser Lys Thr Phe Phe Val Leu Pro Leu Arg Gly Lys
        420                 425                 430

Leu Ser Phe Trp Glu Ala Gly Thr Thr Lys Ala Gly Tyr Pro Tyr Asn
    435                 440                 445

Tyr Asn Thr Thr Ala Ser Asp Gln Ile Leu Ile Glu Asn Ala Ala Gly
450                 455                 460

His Arg Val Ala Ile Ser Thr Tyr Thr Thr Arg Leu Gly Ala Gly Pro
465                 470                 475                 480

Val Ala Ile Ser Ala Ala Val Leu Ala Pro Arg Ser Ala Leu Ala
            485                 490                 495

Leu

<210> SEQ ID NO 11
<211> LENGTH: 497
<212> TYPE: PRT
<213> ORGANISM: Hepatitis E virus
<220> FEATURE:
<221> NAME/KEY: misc_feature
<222> LOCATION: (257)..(257)
<223> OTHER INFORMATION: Xaa can be any naturally occurring amino acid
```

<400> SEQUENCE: 11

```
Ser Arg Arg Arg Ser Thr Pro Thr Gly Ala Ser Pro Leu Thr Ala Val
1               5                   10                  15

Ala Pro Ala Pro Asp Thr Arg Pro Val Pro Asp Val Asp Ser Arg Gly
            20                  25                  30

Ala Ile Leu Arg Arg Gln Tyr Asn Leu Ser Thr Ser Pro Leu Thr Ser
        35                  40                  45

Thr Ile Ala Ser Gly Thr Asn Leu Val Leu Tyr Ala Ala Pro Leu Ser
    50                  55                  60

Pro Leu Leu Pro Leu Gln Asp Gly Thr Asn Thr His Ile Met Ala Thr
65                  70                  75                  80

Glu Ala Ser Asn Tyr Ala Gln Tyr Arg Val Val Arg Ala Thr Ile Arg
                85                  90                  95

Tyr Arg Pro Leu Val Pro Asn Ala Val Gly Gly Tyr Ala Ile Ser Ile
            100                 105                 110

Ser Phe Trp Pro Gln Thr Thr Thr Pro Thr Ser Val Asp Met Asn
        115                 120                 125

Ser Ile Thr Ser Thr Asp Val Arg Ile Val Val Gln Pro Gly Leu Ala
    130                 135                 140

Ser Glu Leu Val Ile Pro Ser Glu Arg Leu His Tyr Arg Asn Gln Gly
145                 150                 155                 160

Trp Arg Ser Val Glu Thr Ser Gly Val Ala Glu Glu Ala Thr Ser
                165                 170                 175

Gly Leu Val Met Leu Cys Ile His Gly Ser Pro Val Asn Ser Tyr Thr
            180                 185                 190

Asn Thr Pro Tyr Thr Gly Ala Leu Gly Leu Leu Asp Phe Ala Leu Glu
        195                 200                 205

Leu Glu Phe Arg Asn Leu Thr Pro Gly Asn Thr Asn Thr Arg Val Ser
    210                 215                 220

Arg Tyr Ser Ser Thr Ala Arg His Arg Leu His Arg Gly Ala Asp Gly
225                 230                 235                 240

Thr Ala Glu Leu Thr Thr Thr Ala Ala Thr Arg Phe Met Lys Asp Leu
                245                 250                 255

Xaa Phe Thr Gly Ser Asn Gly Ile Gly Glu Val Gly Arg Gly Ile Ala
            260                 265                 270

Leu Thr Leu Phe Asn Leu Ala Asp Thr Leu Leu Gly Leu Pro Thr
        275                 280                 285

Glu Leu Ile Ser Ser Ala Gly Gly Gln Leu Phe Tyr Ser Arg Pro Val
290                 295                 300

Val Ser Ala Asn Gly Glu Pro Thr Val Lys Leu Tyr Thr Ser Val Glu
305                 310                 315                 320

Asn Ala Gln Gln Asp Lys Gly Ile Ala Ile Pro His Asp Ile Asp Leu
                325                 330                 335

Gly Asp Ser Arg Val Val Ile Gln Asp Tyr Asp Asn Gln His Glu Gln
            340                 345                 350

Asp Arg Pro Thr Pro Ser Pro Ala Pro Ser Arg Pro Phe Ser Val Leu
        355                 360                 365

Arg Val Asn Asp Val Leu Trp Leu Thr Met Thr Ala Ala Glu Tyr Asp
    370                 375                 380

Gln Thr Thr Tyr Gly Thr Ser Thr Asp Pro Val Tyr Val Ser Asp Thr
385                 390                 395                 400

Val Thr Phe Val Asn Val Ala Thr Gly Ala Gln Gly Val Ala Arg Ser
```

```
            405                 410                 415
Leu Asp Trp Ser Lys Val Thr Leu Asp Gly Arg Pro Leu Thr Thr Ile
        420                 425                 430

Gln Arg His Ser Lys Asn Tyr Phe Val Leu Pro Leu Arg Gly Lys Leu
        435                 440                 445

Ser Phe Trp Glu Ala Gly Thr Thr Lys Ala Gly Tyr Pro Tyr Asn Tyr
        450                 455                 460

Asn Thr Thr Ala Ser Asp Gln Ile Leu Ile Glu Asn Ala Ala Gly His
465                 470                 475                 480

Arg Val Cys Ile Ser Thr Tyr Thr Thr Ser Leu Gly Ser Gly Pro Val
                485                 490                 495

Ser

<210> SEQ ID NO 12
<211> LENGTH: 497
<212> TYPE: PRT
<213> ORGANISM: Hepatitis E virus

<400> SEQUENCE: 12

Ala Val Ala Pro Ala Pro Asp Thr Thr Pro Val Pro Asp Val Asp Ser
1               5

```
                275                 280                 285
Pro Val Val Ser Ala Asn Gly Glu Pro Thr Val Lys Leu Tyr Thr Ser
            290                 295                 300

Val Glu Asn Ala Gln Gln Asp Lys Gly Ile Ala Ile Pro His Glu Ile
305                 310                 315                 320

Asp Leu Gly Asp Ser Arg Val Thr Ile Gln Asp Tyr Asp Asn Gln His
                325                 330                 335

Glu Gln Asp Arg Pro Thr Pro Ser Pro Ala Pro Ser Arg Pro Phe Ser
            340                 345                 350

Val Leu Arg Val Asn Asp Val Leu Trp Leu Thr Leu Thr Ala Ala Glu
            355                 360                 365

Tyr Asp Gln Thr Thr Tyr Gly Ser Thr Thr Asn Pro Met Tyr Val Ser
            370                 375                 380

Asp Thr Val Thr Phe Val Asn Val Ala Thr Gly Ala Gln Gly Val Ala
385                 390                 395                 400

Arg Ala Leu Asp Trp Ser Lys Val Thr Phe Asp Gly Arg Pro Leu Thr
                405                 410                 415

Thr Val Gln Gln Tyr Gly Lys Ser Phe Phe Val Leu Pro Leu Arg Gly
            420                 425                 430

Lys Leu Ser Phe Trp Glu Ala Gly Thr Val Lys Ala Gly Tyr Pro Tyr
            435                 440                 445

Asn Tyr Asn Thr Thr Ala Ser Asp Gln Ile Leu Val Glu Asn Ala Pro
450                 455                 460

Gly His Arg Val Cys Ile Ser Thr Tyr Thr Thr Asn Leu Gly Ser Gly
465                 470                 475                 480

Pro Val Ser Ile Ser Ala Val Gly Val Leu Ala Pro His Ala Ala Thr
                485                 490                 495

Ala

<210> SEQ ID NO 13
<211> LENGTH: 178
<212> TYPE: PRT
<213> ORGANISM: Hepatitis E virus

<400> SEQUENCE: 13

Ile Asp Leu Gly Glu Ser Arg Val Val Ile Gln Asp Tyr Asp Asn Gln
1               5                   10                  15

His Glu Gln Asp Arg Pro Thr Pro Ser Pro Ala Pro Ser Arg Pro Phe
            20                  25                  30

Ser Val Leu Arg Ala Asn Asp Val Leu Trp Leu Ser Leu Thr Ala Ala
        35                  40                  45

Glu Tyr Asp Gln Ser Thr Tyr Gly Ser Ser Thr Gly Pro Val Tyr Val
    50                  55                  60

Ser Asp Ser Val Thr Leu Val Asn Val Ala Thr Gly Ala Gln Ala Val
65                  70                  75                  80

Ala Arg Ser Leu Asp Trp Thr Lys Val Thr Leu Asp Gly Arg Pro Leu
                85                  90                  95

Ser Thr Ile Gln Gln Tyr Ser Lys Thr Phe Phe Val Leu Pro Leu Arg
            100                 105                 110

Gly Lys Leu Ser Phe Trp Glu Ala Gly Thr Thr Lys Ala Gly Tyr Pro
        115                 120                 125

Tyr Asn Tyr Asn Thr Thr Ala Ser Asp Gln Leu Leu Val Glu Asn Ala
    130                 135                 140

Ala Gly His Arg Val Ala Ile Ser Thr Tyr Thr Thr Ser Leu Gly Ala
```

```
145                 150                 155                 160
Gly Pro Val Ser Ile Ser Ala Val Ala Val Leu Ala Pro His Ser Ala
                165                 170                 175
Leu Ala

<210> SEQ ID NO 14
<211> LENGTH: 30
<212> TYPE: DNA
<213> ORGANISM: Artificial Sequence
<220> FEATURE:
<223> OTHER INFORMATION: synthetic forward primer sequence a - parental

<400> SEQUENCE: 14
gaccagtcca cttatggctc ttcgactggc                                          30

<210> SEQ ID NO 15
<211> LENGTH: 30
<212> TYPE: DNA
<213> ORGANISM: Artificial Sequence
<220> FEATURE:
<223> OTHER INFORMATION: synthetic reverse primer sequence a - parental

<400> SEQUENCE: 15
gccagtcgaa gagccataag tggactggtc                                          30

<210> SEQ ID NO 16
<211> LENGTH: 30
<212> TYPE: DNA
<213> ORGANISM: Artificial Sequence
<220> FEATURE:
<223> OTHER INFORMATION: synthetic forward primer sequence a - cysteine
      mutation

<400> SEQUENCE: 16
gaccagtcca cttgcggctc ttcgactggc                                          30

<210> SEQ ID NO 17
<211> LENGTH: 30
<212> TYPE: DNA
<213> ORGANISM: Artificial Sequence
<220> FEATURE:
<223> OTHER INFORMATION: synthetic reverse primer sequence a - cysteine
      mutation

<400> SEQUENCE: 17
gccagtcgaa gagccgcaag tggactgctg                                          30

<210> SEQ ID NO 18
<211> LENGTH: 30
<212> TYPE: DNA
<213> ORGANISM: Artificial Sequence
<220> FEATURE:
<223> OTHER INFORMATION: synthetic forward primer sequence b - parental

<400> SEQUENCE: 18
cttatggctc ttcgactggc ccagtttatg                                          30

<210> SEQ ID NO 19
<211> LENGTH: 30
<212> TYPE: DNA
<213> ORGANISM: Artificial Sequence
<220> FEATURE:
<223> OTHER INFORMATION: synthetic reverse primer sequence b - parental

<400> SEQUENCE: 19
```
cataaactgg gccagtcgaa gagccataag                                       30

<210> SEQ ID NO 20
<211> LENGTH: 30
<212> TYPE: DNA
<213> ORGANISM: Artificial Sequence
<220> FEATURE:
<223> OTHER INFORMATION: synthetic forward primer sequence b - cysteine
      mutation

<400> SEQUENCE: 20
cttatggctc ttcgtgcggc ccagtttatg                                       30

<210> SEQ ID NO 21
<211> LENGTH: 30
<212> TYPE: DNA
<213> ORGANISM: Artificial Sequence
<220> FEATURE:
<223> OTHER INFORMATION: synthetic reverse primer sequence b - cysteine
      mutation

<400> SEQUENCE: 21
cataaactgg gccgcacgaa gagccataag                                       30

<210> SEQ ID NO 22
<211> LENGTH: 29
<212> TYPE: DNA
<213> ORGANISM: Artificial Sequence
<220> FEATURE:
<223> OTHER INFORMATION: synthetic forward primer sequence c - parental

<400> SEQUENCE: 22
ccatccagca gtactcgaag accttcttt                                        29

<210> SEQ ID NO 23
<211> LENGTH: 29
<212> TYPE: DNA
<213> ORGANISM: Artificial Sequence
<220> FEATURE:
<223> OTHER INFORMATION: synthetic reverse primer sequence c - parental

<400> SEQUENCE: 23
aaagaaggtc ttcgagtact gctggatgg                                        29

<210> SEQ ID NO 24
<211> LENGTH: 29
<212> TYPE: DNA
<213> ORGANISM: Artificial Sequence
<220> FEATURE:
<223> OTHER INFORMATION: synthetic forward primer sequence c - cysteine
      mutation

<400> SEQUENCE: 24
ccatccagca gtactgcaag accttcttt                                        29

<210> SEQ ID NO 25
<211> LENGTH: 29
<212> TYPE: DNA
<213> ORGANISM: Artificial Sequence
<220> FEATURE:
<223> OTHER INFORMATION: synthetic reverse primer sequence c - cysteine
      mutation

<400> SEQUENCE: 25
aaagaaggtc ttgcagtact gctggatgg                                        29

<210> SEQ ID NO 26
<211> LENGTH: 33
<212> TYPE: DNA
<213> ORGANISM: Artificial Sequence
<220> FEATURE:
<223> OTHER INFORMATION: synthetic forward primer sequence d - parental

<400> SEQUENCE: 26
caactgcttg tcgagaatgc cgggcaccgg gtc                          33

<210> SEQ ID NO 27
<211> LENGTH: 33
<212> TYPE: DNA
<213> ORGANISM: Artificial Sequence
<220> FEATURE:
<223> OTHER INFORMATION: synthetic reverse primer sequence d - parental

<400> SEQUENCE: 27
gacccggtgc ccggcattct cgacaagcag ttg                          33

<210> SEQ ID NO 28
<211> LENGTH: 33
<212> TYPE: DNA
<213> ORGANISM: Artificial Sequence
<220> FEATURE:
<223> OTHER INFORMATION: synthetic forward primer sequence d - cysteine
      mutation

<400> SEQUENCE: 28
caactgcttg tcgagtgcgc cgggcaccgg gtc                          33

<210> SEQ ID NO 29
<211> LENGTH: 33
<212> TYPE: DNA
<213> ORGANISM: Artificial Sequence
<220> FEATURE:
<223> OTHER INFORMATION: synthetic reverse primer sequence d - cysteine
      mutation

<400> SEQUENCE: 29
gacccggtgc ccggcgcact cgacaagcag ttg                          33

<210> SEQ ID NO 30
<211> LENGTH: 29
<212> TYPE: DNA
<213> ORGANISM: Artificial Sequence
<220> FEATURE:
<223> OTHER INFORMATION: synthetic forward primer sequence e - parental

<400> SEQUENCE: 30
tccacttaca ccactagcct gggtgctgg                               29

<210> SEQ ID NO 31
<211> LENGTH: 29
<212> TYPE: DNA
<213> ORGANISM: Artificial Sequence
<220> FEATURE:
<223> OTHER INFORMATION: synthetic reverse primer sequence e - parental

<400> SEQUENCE: 31
ccagcaccca ggctagtggt gtaagtgga                               29

<210> SEQ ID NO 32
<211> LENGTH: 29
<212> TYPE: DNA
<213> ORGANISM: Artificial Sequence
<220> FEATURE:

```
<223> OTHER INFORMATION: synthetic forward primer sequence e - cysteine
      mutation

<400> SEQUENCE: 32
tccacttaca cctgcagcct gggtgctgg                                           29

<210> SEQ ID NO 33
<211> LENGTH: 29
<212> TYPE: DNA
<213> ORGANISM: Artificial Sequence
<220> FEATURE:
<223> OTHER INFORMATION: synthetic reverse primer sequence e - cysteine
      mutation

<400> SEQUENCE: 33
ccagcaccca ggctacgggt gtaagtgga                                           29
```